(12) United States Patent
Schwoebel et al.

(10) Patent No.: US 8,067,184 B2
(45) Date of Patent: Nov. 29, 2011

(54) OPTOELECTRONIC DETECTION SYSTEM

(75) Inventors: Eric D. Schwoebel, Woburn, MA (US); James D. Harper, Boston, MA (US); Martha S. Petrovick, Barre, MA (US); Frances E. Nargi, Littleton, MA (US); Todd H. Rider, Littleton, MA (US); Kristine E. Hogan, Danvers, MA (US); Richard H. Mathews, Chelmsford, MA (US); Joseph Lacirignola, Beverly, MA (US); Mark Hennessy, Cambridge, MA (US); Trina R. Vian, Groton, MA (US); Rose M. Joseph, Westford, MA (US); Raymond S. Uttaro, Lexington, MA (US); Shaun Berry, Chelmsford, MA (US); Bernadette Johnson, Hollis, NH (US); Mark A. Hollis, Concord, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 164 days.

(21) Appl. No.: 12/217,471

(22) Filed: Jul. 3, 2008

(65) Prior Publication Data

US 2010/0041031 A1 Feb. 18, 2010

Related U.S. Application Data

(60) Division of application No. 11/001,583, filed on Dec. 1, 2004, now Pat. No. 7,422,860, which is a continuation-in-part of application No. 10/467,242, filed as application No. PCT/US02/03606 on Feb. 6, 2002, now Pat. No. 7,214,346.

(60) Provisional application No. 60/266,977, filed on Feb. 7, 2001.

(51) Int. Cl.
*G01N 33/53* (2006.01)
*C12Q 1/00* (2006.01)

(52) U.S. Cl. .................. 435/7.1; 435/4; 435/29
(58) Field of Classification Search .................. None
See application file for complete search history.

(56) References Cited

U.S. PATENT DOCUMENTS

| | | | |
|---|---|---|---|
| 3,880,592 A | 4/1975 | Kelley et al. | |
| 4,493,895 A | 1/1985 | Colaruotolo et al. | |
| 4,499,052 A | 2/1985 | Fulwyler | |
| 4,632,761 A | 12/1986 | Bowers et al. | |
| 4,675,287 A | 6/1987 | Reisfeld et al. | |
| 4,946,778 A | 8/1990 | Ladner et al. | |
| 5,055,408 A | 10/1991 | Higo et al. | |
| 5,126,276 A | 6/1992 | Fish et al. | |
| 5,139,937 A | 8/1992 | Inouye et al. | |
| 5,162,227 A | 11/1992 | Cormier | |
| 5,223,409 A | 6/1993 | Ladner et al. | |
| 5,292,658 A | 3/1994 | Cormier et al. | |
| 5,360,728 A | 11/1994 | Prasher | |
| 5,418,155 A | 5/1995 | Cormier et al. | |
| 5,422,266 A | 6/1995 | Cormier et al. | |
| 5,541,309 A | 7/1996 | Prasher | |
| 5,552,064 A | 9/1996 | Chachowski et al. | |
| 5,578,269 A | 11/1996 | Yaremko et al. | |
| 5,698,450 A | 12/1997 | Ringrose et al. | |
| 5,701,012 A | 12/1997 | Ho | |
| 5,702,884 A | 12/1997 | Ekeze et al. | |
| 5,714,666 A | 2/1998 | Pritchett et al. | |
| 5,744,320 A | 4/1998 | Sherf et al. | |
| 5,744,579 A | 4/1998 | Cormier et al. | |
| 5,766,941 A | 6/1998 | Cormier et al. | |
| 5,798,441 A | 8/1998 | Cormier et al. | |
| 5,846,708 A | 12/1998 | Hollis et al. | |
| 5,932,795 A | 8/1999 | Koutrakis et al. | |
| 5,985,214 A | 11/1999 | Stylli et al. | |
| 6,007,778 A | 12/1999 | Cholewa | |
| 6,087,114 A | 7/2000 | Rider | |
| 6,103,479 A | 8/2000 | Taylor | |
| 6,228,610 B1 | 5/2001 | Flor et al. | |
| 6,239,453 B1 | 5/2001 | Yamada et al. | |
| 6,248,542 B1 | 6/2001 | Rider et al. | |
| 6,331,415 B1 | 12/2001 | Cabilly et al. | |
| 6,672,947 B2 | 1/2004 | Tsao et al. | |
| 6,800,448 B2 | 10/2004 | Rider et al. | |
| 6,872,538 B1 | 3/2005 | Dupriez et al. | |
| 7,090,988 B2 | 8/2006 | Rider et al. | |
| 7,214,346 B2 | 5/2007 | Harper et al. | |
| 7,422,860 B2 | 9/2008 | Schwoebel et al. | |

(Continued)

FOREIGN PATENT DOCUMENTS

EP      0 301 583 A2      2/1989

(Continued)

OTHER PUBLICATIONS

Restriction Requirement, U.S. Appl. No. 08/987,410, Dated: Oct. 1, 1998.
Office Action, U.S. Appl. No. 08/987,410, Dated: Feb. 4, 1999.
Notice of Allowance and Issue Fee Due, U.S. Appl. No. 08/987,410, Dated: Sep. 21, 1999.
Restriction Requirement, U.S. Appl. No. 09/169,196, Dated: Mar. 27, 2000.
Office Action, U.S. Appl. No. 09/169,196, Dated: Aug. 22, 2000.
Notice of Allowance and Issue Fee Due, U.S. Appl. No. 09/169,196, Dated: Feb. 12, 2001.

(Continued)

*Primary Examiner* — James Martinell
(74) *Attorney, Agent, or Firm* — Hamilton, Brook, Smith & Reynolds, P.C.

(57) ABSTRACT

The invention described herein provides methods for the detection of soluble antigens. In particular, the methods provide for the detection of soluble proteins and chemicals. In addition, the invention provides methods of detecting a nucleic acid sequence in a sample. Also described is an emittor cell comprising an Fc receptor and an emittor molecule for the detection of a target particle in a sample wherein the target particle to be detected is bound by one or more antibodies. Also provided is an optoelectronic sensor device for detecting a target particle in a plurality of samples.

24 Claims, 53 Drawing Sheets
(29 of 53 Drawing Sheet(s) Filed in Color)

U.S. PATENT DOCUMENTS

| | | | |
|---|---|---|---|
| 7,517,660 | B2 | 4/2009 | Rider et al. |
| 7,947,509 | B2 | 5/2011 | Harper et al. |
| 2001/0016328 | A1 | 8/2001 | Rider et al. |
| 2002/0045189 | A1 | 4/2002 | Imajo et al. |
| 2002/0106786 | A1 | 8/2002 | Carvalho et al. |
| 2003/0104390 | A1 | 6/2003 | Etienne et al. |
| 2007/0087391 | A1 | 4/2007 | Rider et al. |
| 2008/0009017 | A1 | 1/2008 | Harper et al. |
| 2010/0003700 | A1 | 1/2010 | Rider et al. |
| 2010/0062415 | A1 | 3/2010 | Schwoebel et al. |

FOREIGN PATENT DOCUMENTS

| | | |
|---|---|---|
| EP | 0 372 352 B1 | 6/1995 |
| EP | 0 823 633 A1 | 2/1998 |
| EP | 1 364 070 B1 | 11/2006 |
| EP | 1 145 002 B2 | 12/2008 |
| FR | 2 790 093 A1 | 8/2000 |
| JP | 64-035374 | 2/1989 |
| JP | 2253162 | 10/1990 |
| JP | 3153700 | 7/1991 |
| JP | 63-35641 | 12/1994 |
| JP | 9-509494 T | 9/1997 |
| JP | 2004-527736 A | 9/2004 |
| WO | WO 86/07463 A1 | 12/1986 |
| WO | WO 95/23348 A1 | 8/1995 |
| WO | WO 99/30156 A1 | 6/1999 |
| WO | WO 99/58975 A1 | 11/1999 |
| WO | WO 00/02045 A2 | 1/2000 |
| WO | WO 00/02045 A3 | 1/2000 |
| WO | WO 01/36965 A2 | 5/2001 |
| WO | WO 01/36965 A3 | 5/2001 |
| WO | WO 02/066683 | 8/2002 |
| WO | WO 2007/046825 A2 | 4/2007 |
| WO | WO 2008/048300 A2 | 4/2008 |

OTHER PUBLICATIONS

Notification of Transmittal of the International Search Report or the Declaration, International Application No. PCT/US98/25539, Dated Mar. 23, 1999.

Notification of Transmittal of International Preliminary Examination Report, International Application No. PCT/US98/25539, Dated: Sep. 2, 1999.

Office Action, U.S. Appl. No. 09/848,811, Dated: Aug. 26, 2003.

Notice of Allowance and Fees Due, U.S. Appl. No. 09/848,811, Dated: May 4, 2004.

Office Action, U.S. Appl. No. 10/910,554, Dated: Sep. 29, 2005.

Notice of Allowance and Fees Due, U.S. Appl. No. 10/910,554, Dated: Apr. 12, 2006.

Office Action, U.S. Appl. No. 11/471,275, Dated: Jun. 27, 2008.

Notice of Allowance and Fees Due, U.S. Appl. No. 11/471,275, Dated: Dec. 3, 2008.

Notification of Transmittal of the International Search Report or the Declaration, International Application No. PCT/US02/03606, Dated: Aug. 9, 2002.

Notification of Transmittal of International Preliminary Examination Report, International Application No. PCT/US02/03606, Dated: Nov. 12, 2002.

Office Action, Australian Application No. 2002256992, Dated: Jun. 5, 2006.

Chinese First Office Action and English Translation, Chinese Application No. 02807911.6, Dated: Mar. 4, 2005.

Chinese Second Office Action and English Translation, Chinese Application No. 02807911.6, Dated: May 12, 2006.

Chinese Grounds of Rejection and English Translation, Chinese Application No. 02807911.6, Dated: Apr. 6, 2007.

English Translation of Chinese Decision of Granting Patent Right for Invention, Chinese Application No. 02807911.6, Dated: Feb. 20, 2009.

European Search Report, European Application No. 02726568.5, Dated: Jan. 30, 2004.

Office Action, European Application No. 02726568.5, Dated: May 14, 2004.

Office Action, European Application No. 02726568.5, Dated: Dec. 1, 2004.

Office Action, European Application No. 02726568.5, Dated: May 30, 2005.

Summons to Attend Oral Proceedings, European Application No. 02726568.5, Dated: Nov. 21, 2005.

Decision to Grant a European Patent, European Application No. 02726568.5, Dated: Oct. 19, 2006.

English Translation of Notice of Reasons for Rejection, Japanese Application No. 2002-566387, Dated: Feb. 8, 2008.

English Translation of Notice of Reasons for Rejection, Japanese Application No. 2002-566387, Dated: Dec. 8, 2008.

English Translation of Mexican Office Action, Mexican Application No. PA/a/2003/007070, Dated: Dec. 12, 2006.

English Translation of Mexican Office Action, Mexican Application No. PA/a/2003/007070, Dated: Aug. 5, 2009.

Restriction Requirement, U.S. Appl. No. 10/467,242, Dated: Apr. 28, 2005.

Office Action, U.S. Appl. No. 10/467,242, Dated: Jul. 5, 2005.

Office Action, U.S. Appl. No. 10/467,242, Dated: Apr. 10, 2006.

Notice of Allowance and Fees Due, U.S. Appl. No. 10/467,242, Dated: Jan. 4, 2007.

Response to Rule 312 Communication, U.S. Appl. No. 10/467,242, Dated: Feb. 21, 2007.

Restriction Requirement, U.S. Appl. No. 11/001,583, Dated: Mar. 9, 2007.

Office Action, U.S. Appl. No. 11/001,583, Dated: Oct. 3, 2007.

Office Communication, U.S. Appl. No. 11/001,583, Dated: Mar. 21, 2008.

Notice of Allowance and Fees Due, U.S. Appl. No. 11/001,583, Dated: Apr. 10, 2008.

Notification of Transmittal of the International Search Report and the Written Opinion of the International Searching Authority, or the Declaration, International Application No. PCT/US2005/043343, Dated: May 7, 2007.

Notification Concerning Transmittal of International Preliminary Report on Patentability, International Application No. PCT/US2005/043343, Dated: Jun. 14, 2007.

Extended European Search Report, European Application No. 06022907.7, Dated: Jun. 19, 2007.

Office Communication, European Application No. 06022907.7, Dated: Apr. 8, 2008.

Office Communication, European Application No. 06022907.7, Dated: May 30, 2008.

Office Action, European Application No. 06022907.7, Dated: Feb. 12, 2009.

Restriction Requirement, U.S. Appl. No. 11/800,607, Dated: Apr. 29, 2009.

Office Action, U.S. Appl. No. 11/800,607, Dated: Nov. 30, 2009.

Office Action, European Application No. 05 858 641.3, Dated: Nov. 15, 2007.

Office Action, European Application No. 05 858 641.3, Dated: Sep. 22, 2008.

Office Communication, European Application No. 05 858 641.3, Dated: Apr. 20, 2009.

Notice of Intent to Grant, European Application No. 05 858 641.3, Dated: Oct. 7, 2009.

Office Action, Australian Application No. 2005337484, Dated: Mar. 24, 2009.

English Translation of Chinese Office Action, Chinese Application No. 2005800473625, Dated: Aug. 7, 2009.

Notification of Transmittal of the International Search Report and the Written Opinion of the International Searching Authority, or the Declaration, International Application No. PCT/US2006/045691, Dated: Aug. 19, 2008.

Notification Concerning Transmittal of International Preliminary Report on Patentability, International Application No. PCT/US2006/045691, Dated: Sep. 12, 2008.

Office Action, Australian Application No. 2006350038, Dated Feb. 5, 2010.

Office Action, European Application No. 06 851 774.7, Dated: Jun. 29, 2009.

Boie, Y., et al., "Molecular Cloning and Characterization of the Four Rat Prostaglandin $E_2$ Prostanoid Receptor Subtypes," *European Journal of Pharmacology*, 340:227-241 (1997).

Brini, M., et al., "Transfected Aequorin in the Measurement of Cytosolic $Ca^{2+}$ Concentration ($[Ca^{2+}]_c$)," *Journal of Biological Chemistry*, 270(*17*):9896-9903 (1995).

Murgia, M., et al., "Cytosolic Free Calcium Concentration in the Mitogenic Stimulation of T Lymphocytes by Anti-CD3 Monoclonal Antibodies," *Cell Calcium*, 16:167-180 (1994).

Rizzuto, R., et al., "Microdomains with High $Ca^{2+}$ Close to $IP_3$-Sensitive Channels That Are Sensed by Neighboring Mitochondria," *Science*, 262:744-747 (1993).

Rizzuto, R., et al., "Rapid Changes of Mitochondrial $Ca^{2+}$ Revealed by Specifically Targeted Recombinant Aequorin," *Nature*, 358:325-327 (1992).

Sedlik, C., et al., "Recombinant Parvovirus-like Particles as an Antigen Carrier: A Novel Nonreplicative Exogenous Antigen to Elicit Protective Antiviral Cytotoxic T Cells," *Proc. Natl. Acad. Sci. USA*, 94:7503-7508 (1997).

Stables, J., et al., "A Bioluminescent Assay for Agonist Activity at Potentially Any G-Protein-Coupled Receptor," *Analytical Biochemistry*, 252:115-126 (1997).

Office Action, Canadian Patent Application No. 2,437,033, dated Feb. 19, 2010.

Office Action, U.S. Appl. No. 11/800,607, dated Jun. 4, 2010.

Kostov, Y., et al., "All Solid-State GFP Sensor," Biotechnology and Bioengineering, Including: Symposium Biotechnology in Energy Production and Conservation, John Wiley & Sons. NY, vol. 70(4): 473-477 (2000).

Button, D., et al., "Aequorin-expressing Mammalian Cell Lines Used to Report $Ca^{2+}$ Mobilization," *Cell Calcium*,14:663-671 (1993).

Chalfie, M., "Green Fluorescent Protein," *Photochemistry and Photobiology*, 62(4):651-656 (1995).

Mosier, D.E. "Primary In Vitro Antibody Responses by Purified Murine B Lymphocytes in Serum-Free Defined Medium," *The Journal of Immunology* , 127(4):1490-1493 (1981).

Paddle, B.M. "Biosensors for Chemical and Biological Agents of Defence Interest," *Biosensors & Bioelectronics*, 11(11):1079-1113 (1996).

Page, D.L., et al., "A Cell-based Immunobiosensor with Engineered Molecular Recognition-Part II: Enzyme Amplification Systems," *Biosensors & Bioelectronics*, 12(6):457-466 (1997).

Pizziconi, V.B., et al., "A Cell-based Immunobiosensor with Engineered Molecular Recognition-Part I: Design Feasibility," *Biosensors & Bioelectronics*, 12(4):287-299 (1997).

Shimomura, O., et al., "Calcium Binding, Quantum Yield, and Emitting Molecule in Aequorin Bioluminescence," *Nature*, 227:1356-1357 (1970).

Shimomura, O., et al., "Light-emitting Properties of Recombinant Semi-Synthetic Aequorins and Recombinant Fluorescein-conjugated Aequorin for Measuring Cellular Calcium," *Cell Calcium*, 14:373-378 (1993).

Wilson, H.A., et al., "Crosslinkage of B Lymphocyte Surface Immunoglobulin by Anti-Ig or Antigen Induces Prolonged Oscillation of Intracellular Ionized Calcium," *Journal of Experimental Medicine*, 166:601-606 (1987).

Wilson, H.A., et al., "The B Lymphocyte Calcium Response to Anti-Ig Is Diminished by Membrane Immunoglobulin Cross-Linkage to the Fcγ Receptor," *The Journal of Immunology*, 138(6):1712-1718 (1987).

Baylor, D.A., "Photoreceptor Signals and Vision," *Investigative Ophthalmology*, 28(1):34-49 (1987).

Kombrink, E. and Somssich, I.E., "Defense Responses of Plants to Pathogens," *Advances in Botanical Research*, 21:1-34 (1995).

Davis, L.S., et al., "The Induction of T Cell Unresponsiveness by Rapidly Modulating CD3," *J Immunol.* 142:1084-1094 (1989).

Parikh, V.S., et al., "COOH Terminus of Membrane IgM is Essential for an Antigen-Specific Induction of Some But Not All Early Activation Events in Mature B Cells," *J. Exp. Med.*, 174:1103-1109 (1991).

Rider, T.H., et al., "A B Cell-Based Sensor for Rapid Identification of Pathogens," *Science*, 301(5630):213-215 (2003).

Pancrazio, J.J., et al., "Development and Application of Cell-Based Biosensors," *Annals of Biomedical Engineering*, 27(6):697-711 (1999).

"Introducing BioFlash™, a Rapid Diagnostic System for the Ultra-Sensitive Detection of Pathogens." Innovative Biosensors, Inc. [online] (2006). [retrieved on Apr. 10, 2007]. Retrieved from the Internet URL: http://www.innovativebiosensors.com/technology_pathogen_detection.html.

Office Action, Canadian Application 2,437,033, Dated: Sep. 16, 2010.

English Translation of Chinese Office Action, Chinese Application No. 200910137895.2, Dated: Sep. 30, 2010.

Office Action, European Application No. 06851774.7; Dated: Jan. 13, 2011.

U.S. Office Action dated Mar. 2, 2011, U.S. Appl. No. 12/380,603*.

Scott et al., "Isolation of Dengue Viruses from Peripheral Blood Leukocytes of Patients with Hemorrhagic Fever," *Journal of Infectious Diseases*, 141(1):1-6 (1980).

U.S. Office Action, U.S. Appl. No. 12/380,603, Dated Jun. 7, 2011.

English translation of JP Office Action, JP Application No. 2008-543423, Dated Apr. 27, 2011.

U.S. Office Action, U.S. Appl. No. 12/085,495, Dated: Jun. 8, 2011.

Australian Office Action for Application No. 2006350038; Dated Mar. 18, 2011.

U.S. Restriction Requirement for U.S. Appl. No. 12/085,495; Dated Apr. 26, 2011*.

English Translation of Chinese Office Action, Chinese Application No. 200680050691.X, Dated: Jun. 9, 2011.

B-Cell Response to Foot-and-Mouth Disease Virus

- Tests done at Plum Island USDA BL-3 Facility

FIG. 5

Automated Cell-Delivery Concept

- Sensor cells compatible with delivery using syringe pumps, automatic pipettors, etc.
- Different sensor-cell types in individual pre-loaded syringes
- Environmental control to maintain B-cell performance
- One B-cell droplet per test, added after aerosol collection Labels on figure: syringe pump, syringes, tube carriers

Automated Centrifuge-Module Concept

- Cells forced into particles with a 5-second spin
- Indexed motor aligns samples with optics modules for signal collection
- Linear arrangement amenable to automation and scale-up

Direct-Impaction Agent-Delivery System for Sensor Cell Identification Sensor

- Direct-air impaction deposits agents into multiple-well tapes or plates
- High sample concentration via air-to-air concentrator and small fluid volumes (µl)
- Rapid identification with low consumables usage

FIG. 16

Integrated Dry-Impactor/Sensor Concept

Dry Aerosol Collection

Concept

Dry Collector Prototype

- Momentum of particles forces contact with tube surface, where they are retained
- Elimination of collection fluid simplifies system and improves reliability
- Designed for microcentrifuge tubes with operation cost in mind

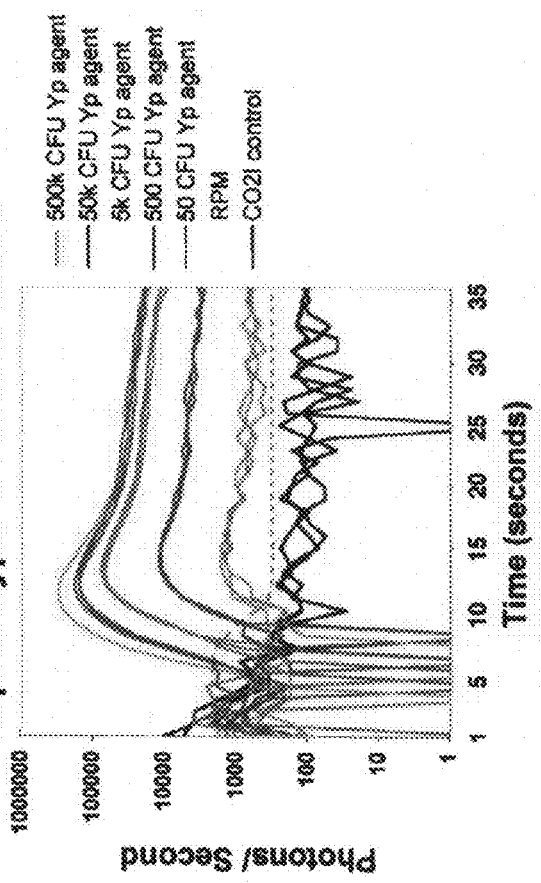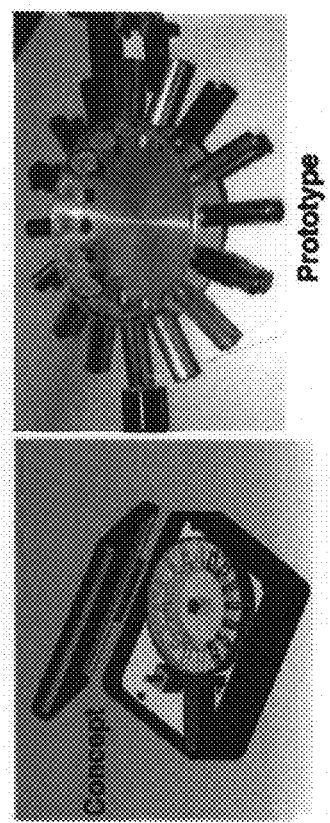
FIG. 45

CANARY Detection of Toxin Simulants

- Modification of CANARY assay to detect soluble, monomeric proteins
  - Speed: Currently ≥ 15 min
  - Sensitivity: 6 ng so far (0.01xLD50)
- Assay modifications under development to optimize speed and sensitivity

FIG. 46

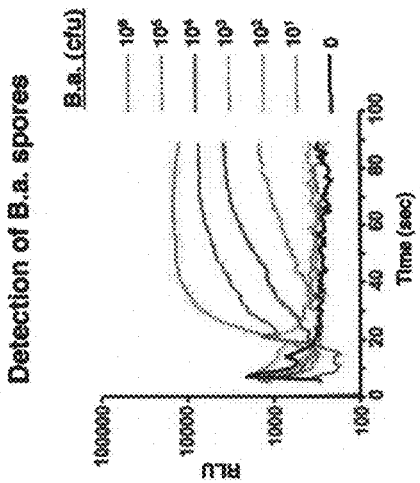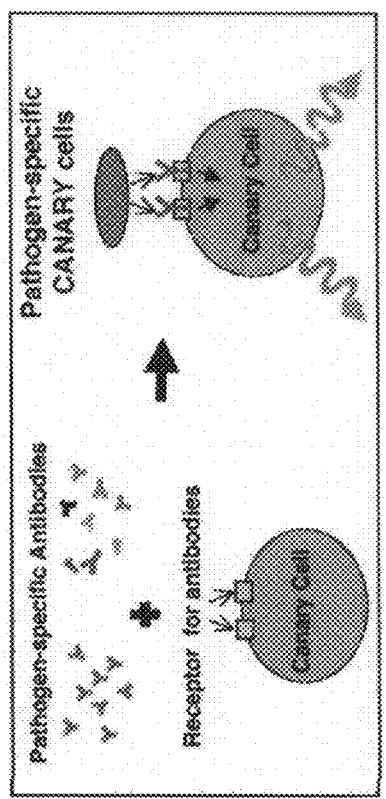
FIG. 47

OPTOELECTRONIC DETECTION SYSTEM

RELATED APPLICATIONS

This application is a divisional of U.S. application Ser. No. 11/001,583, filed Dec. 1, 2004, now U.S. Pat. No. 7,422,860 which is a continuation-in-part of U.S. application Ser. No. 10/467,242, filed Jan. 16, 2004, now U.S. Pat. No. 7,214,346 which is the U.S. National stage of International Application No. PCT/US02/03606, filed Feb. 6, 2002, published in English, which claims the benefit of U.S. Provisional Application No. 60/266,977, filed Feb. 7, 2001.

The entire teachings of the above applications are incorporated herein by reference.

GOVERNMENT SUPPORT

This invention was made with Government funds from U.S. Air Force contract no. F19628-00-C-0002. The Government has certain rights in the invention.

BACKGROUND OF THE INVENTION

The need for small, fast, and sensitive detectors of biological agents which are able to monitor an environment for extended periods of time is underscored by the proliferation of biological and chemical weapons, the poor man's nuclear weapon. Under battlefield conditions, a useful detector would rapidly alert a soldier when a specific biological or chemical agent is detected so that countermeasures can quickly be implemented.

Such detectors would be useful in non-military applications as well. Rapid detection of antibiotic-resistant bacteria in a patient would help clinicians select a more effective therapeutic regimen. Continuous monitoring of a city's drinking water supply would provide early warning of potential pathogens, giving public works officials more time to manage the potential health risks to the public. In addition, the use of these detectors in meat and poultry inspections would be a significant improvement over the current "poke-and-smell" procedure. In general, such detectors are sorely needed analytical and diagnostic applications within the fields of medicine (e.g., veterinary medicine), agriculture, environmental protection (e.g., to diagnose sick building syndrome), and food processing or regulation.

All vertebrates acquire a specific immune response to a foreign agent (antigen) in part by generating an immense diversity of antibody molecules. Antibody molecules bind to antigen with high specificity, e.g., they can differentially bind to two closely related strains of bacteria, viruses, protein, nucleic acid, fungus, protozoa, multicellular parasite, or prion, as well as products produced or induced by those particles.

Antibodies are produced by B cells, a crucial component of the immune system. An antigen can activate a B cell by binding to antibodies on its surface, leading to a cascade of intracellular biochemical reactions which causes a calcium ion influx into the cytosol of the B cell.

For a review of antibody structure and function and B cell activation, see Paul, editor, Fundamental Immunology, 3rd ed., Raven Press, New York (1993).

Devices that exploit antibody diversity for detection of multiple and rare target particles or antigens have been described in U.S. Pat. No. 6,087,114 and U.S. Pat. No. 6,248,542.

These devices generally include a liquid medium containing sensor cells (e.g., a B cell, macrophage or fibroblast), also referred to herein as "CANARY" cells or emittor cells, an optical detector, and the liquid medium receiving target particles to be detected. Each of the cells has receptors (e.g., chimeric or single chain antibodies) which are expressed on its surface and are specific for the antigen to be detected. Binding of the antigen to the receptor results in a signaling pathway involving chemical or biochemical changes (e.g., an increase in calcium concentration). The cells also contain emitter molecules (e.g., aequorin or indo-1) in their cytosol which can emit photons in response to the signaling pathway (e.g., increased calcium concentration in the cytosol). The detector can be separated from the medium containing the cells by a covering (e.g., glass) that is transparent to the photons. Such a covering can serve to support the medium, protect a fragile surface of the detector, or be used as a lens. The optical detector, e.g., a charge-coupled device (CCD) is able to detect the photons emitted from the cells in response to the receptor-mediated signaling pathway and indicate to the user that the antigen to be detected is present. Other optical detectors which can be used in the device include photomultiplier tubes, photodiodes, complimentary metal oxide semiconductor (CMOS) imagers, avalanche photodiodes, and image-intensified charge-coupled devices (ICCD) (see for example, those available from Photek Ltd., East Sussex, UK). In some embodiments, the optical detector is able to distinguish individual cells.

SUMMARY OF THE INVENTION

The invention described herein modifies and advances the devices described in U.S. Pat. No. 6,087,114 and U.S. Pat. No. 6,248,542 to provide methods for the detection of soluble antigens. In particular, the methods provide for the detection of soluble proteins and chemicals. In addition, the invention described herein provides methods of detecting a nucleic acid sequence in a sample. Furthermore, also provided herein is an emittor cell comprising an Fc receptor and an emittor molecule for the detection of a target particle in a sample wherein the target particle to be detected is bound by one or more antibodies. Also provided is an optoelectronic sensor device for detecting a target particle in a plurality of samples using a photon detector.

Detection of a target particle (such as a soluble antigen or a nucleic acid) is mediated in part by binding of the target particle to a receptor, either directly or indirectly, expressed on the cell surface of an emittor cell. Direct binding can be via a receptor, such as an antibody, which binds directly and specifically to the target particle. Indirect binding of the target particle can be through an Fc receptor that binds to an antibody that has been attached (bound) to the target particle.

In one embodiment of the invention, provided herein is a method of detecting a nucleic acid sequence in a sample comprising the steps of a) combining the sample with at least one antigen-conjugated oligonucleotide under conditions suitable for hybridization of the antigen-conjugated oligonucleotide to the nucleic acid sequence; b) adding an emittor cell, wherein said emittor cell comprises one or more receptors which bind to the antigen of the antigen-conjugated oligonucleotides, wherein binding of the one or more receptors to the antigen results in an increase in intracellular calcium, and an emittor molecule that emits a photon in response to the increase in intracellular calcium; and c) measuring photon emission from the emittor cell, thereby detecting a nucleic acid sequence in a sample.

In another embodiment of the invention, provided herein is a method of detecting a nucleic acid sequence in a sample comprising the steps of a) combining the sample with a plurality of antigen-conjugated oligonucleotides under conditions suitable for hybridization of the antigen-conjugated oligonucleotides to the nucleic acid sequence; b) adding an emittor cell, wherein said emittor cell comprises one or more receptors which binds to the antigen of the antigen-conjugated oligonucleotides, wherein binding of the one or more receptors to the antigen results in an increase in intracellular calcium, and an emittor molecule that emits a photon in response to the increase in intracellular calcium; and c) measuring photon emission from the emittor cell, thereby detecting a nucleic acid sequence in a sample.

In a further embodiment of the invention, provided herein is a method of detecting a nucleic acid sequence in a sample comprising the steps of a) combining i) the sample being tested; ii) at least one antigen-conjugated oligonucleotide that is complementary to the nucleic acid sequence; and iii) a solid substrate comprising at least one oligonucleotide complementary to the nucleic acid sequence bound to the solid substrate; under conditions suitable for hybridization of the antigen-conjugated oligonucleotide and the oligonucleotide bound to the solid substrate for hybridizing to the nucleic acid sequence, thereby producing a solid substrate comprising the nucleic acid sequence having at least one hybridized antigen-conjugated oligonucleotide; b) adding to the solid substrate comprising the nucleic acid sequence having at least one hybridized antigen-conjugated oligonucleotide an emittor cell comprising one or more receptors which binds to the antigen of the antigen-conjugated oligonucleotide, wherein binding of the one or more receptors to the antigen results in an increase in intracellular calcium, and wherein said emittor cell further comprises an emittor molecule that emits a photon in response to the increase in intracellular calcium; and c) measuring photon emission from the emittor cell, thereby detecting a nucleic acid sequence in a sample.

In another embodiment of the invention, provided herein is a method of detecting a nucleic acid sequence in a sample comprising the steps of a) combining the sample with at least one antigen-conjugated oligonucleotide under conditions suitable for hybridization of the antigen-conjugated oligonucleotide to the nucleic acid sequence thereby producing an antigen-conjugated hybridization complex; b) adding one or more antibodies specific for the antigen of the antigen-conjugated hybridization complex; c) adding an emittor cell comprising an Fc receptor, wherein binding of the Fc receptor to the one or more antibodies results in an increase in intracellular calcium, and wherein said emittor cell further comprises an emittor molecule that emits a photon in response to the increase in intracellular calcium; and d) measuring photon emission from the emittor cell, thereby detecting a target particle in a sample.

In another embodiment of the invention, provided herein is a method of detecting a target particle in a sample comprising the steps of a) combining the sample with i) an antibody specific for the target particle; and ii) an emittor cell comprising an Fc receptor, wherein binding of the Fc receptor to the antibody results in an increase in intracellular calcium, and wherein said emittor cell further comprises an emittor molecule that emits a photon in response to the increase in intracellular calcium; and b) measuring photon emission from the emittor cell, thereby detecting a target particle in a sample In a further embodiment, provided herein is a method of detecting a soluble antigen in a sample comprising the steps of a) combining the sample with i) one or more antibodies that bind to two different epitopes on the soluble antigen; and ii) an emittor cell comprising an Fc receptor, wherein binding of the Fc receptor to the one or more antibodies results in an increase in intracellular calcium, and wherein said emittor cell further comprises an emittor molecule that emits a photon in response to the increase in intracellular calcium; and b) measuring photon emission from the emittor cell, thereby detecting a target particle in a sample.

Also provided herein is an optoelectronic sensor device for detecting a target particle in a plurality of samples using a photon detector comprising a) a rotor comprising a plurality of positions to hold a plurality of samples; b) one or more samples comprising a mixture of i) a sample to be tested for the target particle; and ii) a cell comprising a receptor for the target particle, wherein binding of the receptor to the target particle results in an increase in intracellular calcium, and wherein said cell further comprises an emittor molecule that emits a photon in response to the increase in intracellular calcium; and c) a photon detector located at a position to detect photons emitted from one or more samples upon rotation of the rotor.

In a further embodiment of the invention, provided herein is an optoelectronic sensor device for detecting a target particle in one or more samples using a photon detector comprising a) a rotor comprising a plurality of positions to hold a plurality of samples; b) one or more samples comprising a mixture of i) a sample to be tested for the target particle; ii) an antibody specific for the target particle; and ii) an emittor cell, wherein said emittor cell comprises an Fc receptor, wherein binding of the Fc receptor to the antibody results in an increase in intracellular calcium, and wherein said emittor cell further comprises an emittor molecule that emits a photon in response to the increase in intracellular calcium; and c) a photon detector located at a position to detect photons emitted from one or more samples upon rotation of the rotor.

In another embodiment of the invention, provided herein is an optoelectronic sensor device for detecting a nucleic acid sequence in one or more samples using a photon detector comprising a) a rotor comprising a plurality of positions to hold a plurality of samples; b) one or more samples comprising a mixture of i) a sample to be tested for the nucleic acid sequence; ii) at least one antigen-conjugated oligonucleotide hybridized to the nucleic acid sequence; and iii) an emittor cell comprising one or more receptors which binds to the antigen of the antigen-conjugated oligonucleotides hybridized to the nucleic acid sequence, wherein binding of the one or more receptors to the antigen results in an increase in intracellular calcium, and wherein said emittor cell further comprises an emittor molecule that emits a photon in response to the increase in intracellular calcium; and c) a photon detector located at a position to detect photons emitted from one or more samples upon rotation of the rotor.

In one embodiment, the rotor comprises sixteen positions to hold sixteen samples.

Furthermore, in another embodiment of the invention, provided herein is a method of detecting a soluble antigen in a sample comprising a) combining the sample with an emittor cell comprising one or more antibodies that bind to two different epitopes on the soluble antigen, wherein binding of the one or more antibodies to the soluble antigen results in an increase in intracellular calcium, and wherein said emittor cell further comprises an emittor molecule that emits a photon in response to the increase in intracellular calcium; and b) measuring photon emission from the emittor cell, thereby detecting a soluble antigen in a sample.

In another embodiment of the invention, provided herein is a method of detecting a soluble antigen in a sample comprising the steps of a) crosslinking the soluble antigen, thereby producing a crosslinked antigen; b) combining with the crosslinked antigen with an emittor cell comprising an antibody that binds to the crosslinked antigen, wherein binding of the antibody to the crosslinked antigen results in an increase in intracellular calcium, and wherein said emittor cell further comprises an emittor molecule that emits a photon in response to the increase in intracellular calcium; and c) measuring photon emission from the emittor cell, thereby detecting a soluble antigen in a sample.

In a further embodiment of the invention, provided herein is a method of detecting a soluble antigen in a sample comprising the steps of a) crosslinking the soluble antigen to a solid substrate, thereby producing a crosslinked soluble antigen bound to a solid substrate; b) adding an emittor cell to the crosslinked soluble antigen bound to the solid substrate, wherein said emittor cell comprises an antibody that binds an epitope on the soluble antigen, wherein binding of the antibody to the crosslinked soluble antigen bound to the solid support results in an increase in intracellular calcium, and wherein said emittor cell further comprises an emittor molecule that emits a photon in response to the increase in intracellular calcium; and c) measuring photon emission from the emittor cell, thereby detecting a soluble antigen in a sample.

In still another embodiment of the invention, provided herein is a method of detecting a soluble antigen in a sample comprising the steps of a) combining the sample with a solid substrate comprising a first antibody that binds a first epitope on the soluble antigen, thereby producing a crosslinked soluble antigen bound to a solid substrate; b) adding an emittor cell to the crosslinked soluble antigen bound to the solid substrate, wherein said emittor cell comprises a second antibody that binds a second epitope on the soluble antigen, wherein binding of the second antibody to the crosslinked soluble antigen bound to the solid support results in an increase in intracellular calcium, and wherein said emittor cell further comprises an emittor molecule that emits a photon in response to the increase in intracellular calcium; and c) measuring photon emission from the emittor cell, thereby detecting a soluble antigen in a sample.

In another embodiment of the invention, provided herein is a method of detecting a chemical in a sample comprising the steps of a) combining the chemical with a peptide, thereby producing a chemical-peptide complex; b) adding an emittor cell comprising one or more antibodies that bind to two different epitopes on the chemical-peptide complex, wherein binding of the one or more antibodies to the chemical-peptide complex results in an increase in intracellular calcium, and wherein said emittor cell further comprises an emittor molecule that emits a photon in response to the increase in intracellular calcium; and c) measuring photon emission from the emittor cell, thereby detecting a chemical in a sample.

In further embodiment of the invention, provided herein is a method of detecting a chemical in a sample comprising the steps of a) combining the chemical with a peptide, thereby producing a chemical-peptide complex; b) crosslinking the chemical-peptide complex, thereby producing a crosslinked chemical-peptide complex; c) combining with the crosslinked chemical-peptide complex with an emittor cell comprising an antibody that binds to the crosslinked chemical-peptide complex, wherein binding of the antibody to the crosslinked chemical-peptide complex results in an increase in intracellular calcium, and wherein said emittor cell further comprises an emittor molecule that emits a photon in response to the increase in intracellular calcium; and d) measuring photon emission from the emittor cell, thereby detecting a soluble antigen in a sample.

In an additional embodiment of the invention, provided herein is a method of detecting a chemical in a sample comprising the steps of a) combining the chemical with an antigen-conjugated peptide, thereby producing a chemical-antigen-conjugated peptide complex; b) adding an emittor cell comprising one or more antibodies that bind to two different epitopes on the chemical-antigen-conjugated peptide complex, wherein binding of the one or more antibodies to the chemical-antigen-conjugated peptide complex results in an increase in intracellular calcium, and wherein said emittor cell further comprises an emittor molecule that emits a photon in response to the increase in intracellular calcium; and c) measuring photon emission from the emittor cell, thereby detecting a chemical in a sample.

In a further embodiment of the invention, provided herein is a method of detecting a chemical in a sample comprising the steps of a) combining the chemical with an antigen-conjugated peptide, thereby producing a chemical-antigen-conjugated peptide complex; b) crosslinking the chemical-antigen-conjugated peptide complex, thereby producing a crosslinked chemical-antigen-conjugated peptide complex; c) adding an emittor cell comprising an antibody that binds to the crosslinked chemical-antigen-conjugated peptide complex, wherein binding of the antibody to the chemical-antigen-conjugated peptide complex results in an increase in intracellular calcium, and wherein said emittor cell further comprises an emittor molecule that emits a photon in response to the increase in intracellular calcium; and d) measuring photon emission from the emittor cell, thereby detecting a soluble antigen in a sample.

The systems of the invention are useful in analytical and diagnostic applications within the fields of medicine (e.g., veterinary medicine), agriculture, environmental protection (e.g., to diagnose sick building syndrome), and food processing or regulation.

The foregoing and other objects, features and advantages of the invention will be apparent from the following more particular description of preferred embodiments of the invention, as illustrated in the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5 illustrates the B cell response to foot-and-mouth disease virus in the optoelectronic sensor.

FIG. 9 illustrates an automated cell-delivery module for the optoelectronic sensor.

FIG. 10 illustrates a dose response relationship for a sample of tularemia cells using the optoelectronic sensor.

FIG. 16 is a schematic illustrating an air impactor/optoelectronic sensor.

FIG. 23 illustrates an impactor config

FIG. 36A U937 cells exhibit an increase in Fcγ RI expression when treated with IFNγ. The relative expression of FcγRI on U937 cells treated with IFNγ (200 ng/ml, open green peak) or untreated (solid purple peak) was measured by immunofluorescence. FIG. 36B U937 cells express functional aequorin protein. U937 cells transfected with the calcium-sensitive luminescent protein aequorin emit light when treated with ionomycin (50 M). FIG. 36C Light is detected following the crosslinking of the Fc receptors on U937 cells with stable aequorin expression. U937 cells were preincubated with 10 μg/ml human IgG, then washed and treated with goat anti-human IgG (Fab2').

FIG. 37A mouse anti-*B. anthracis* spore, FIG. 37B rabbit polyclonal anti-*B. anthracis* spore, FIG. 37C mouse anti-*F. tularensis*, or FIG. 37D mouse anti-*B. subtilis* hybridoma supernatant. Cells were then used in the standard CANARY assay where they detected as few as 1000 cfu *B. anthracis* spores with the monoclonal antibody and 10,000 cfu spores with the rabbit polyclonal, as well as 10,000 cfu *F. tularensis* and 1,000 cfu *B. subtilis* spores.

FIG. 38A U937 cells incubated with mouse anti-*F. tularensis* antibodies did not respond to $10^5$ cfu of *B. anthracis* spores, but did to 106 cfu of *F. tularensis*. FIG. 38B Cells loaded with mouse anti-*B. anthracis* spore antibodies did not respond to *F. tularensis* but did to $10^6$ cfu of *B. anthracis* spores. FIG. 38C The cells did not show any response to the $10^6$ cfu of *F. tularensis* in the absence of anti-*F. tularensis* antibody [$10^6$ cfu F.t. (No ab)].

FIG. 39 is an illustration of a 16-channel sensor. A sensor was designed which allowed the simultaneous measurement of 16 samples using a single light-gathering channel. The sensor consists of a rotor holding sixteen 1.5-ml tubes horizontally, equally distributed about its circumference, and driven by a variable speed motor about a vertical axis. A single fixed photon-detecting element (e.g., a PMT) is positioned in the plane of the rotor just beyond the path of the tubes during rotation. In this way, each of the tubes is sequentially and repetitively brought into close proximity to the PMT, allowing its light output to be sampled on each pass. Finally, an optical switch consisting of an optical source (an infrared LED) and a detector (a phototransistor) is used to control the counting of detected photons and the reorganization of the data into 16 fields, each associated with a specific sample.

FIG. 40 is a graph. Data from the 16-channel sensor demonstrates an LOD identical to that obtained in a single-channel instrument, except that 16 samples are measured simultaneously. A single measurement consists of the following steps: preparing 16 samples (and/or controls) in individual 1.5-ml tubes, introducing an aliquot of emittor cells into each of the tubes, installing the tubes into the rotor situated in a dark box, localizing the emittor cells to the bottom of the tubes using a brief (5 sec) centrifugal spin at high RCF (~2000 g), reducing the rotor speed to 60 rpm for the duration of the measurement (each tube being sampled once every second), and generating a time-series of photon counts for each sample for display and/or input to a computer algorithm for evaluation.

FIG. 41 is an illustration of a portable 16-channel-sensor design.

FIG. 42 is an illustration of a CANARY Disc (CD) integrated aerosol collection and emittor cell delivery.

FIG. 43 is an illustration of an aerosol collection module cutaway with impaction nozzle and transparent tube.

FIG. 44 is an illustration of an emittor cell delivery module with valve delivery system.

FIG. 45 is an overview of a 16 channel sensor and results from using same.

FIG. 46 is an overview of the detection of toxins.

FIG. 47 is an overview of a sensor cell that expresses aequorin and a generalized antibody receptor.

FIG. 48 is a schematic for the detection of soluble, monomeric antigens: strategy 1. A single emittor cell is engineered to express two different antibodies against two different epitopes on the same, monomeric antigen. The presence of antigen crosslinks the antibodies, stimulating the emittor cell to emit light.

FIG. 49 is a graph depicting the results of a cell line expressing antibodies against both *B. anthracis* and *Y. pestis* which was challenged with each *B. anthracis* and *Y. pestis*. This clonal cell line can detect as few as 50 cfu of either *B. anthracis* and *Y. pestis*, indicating that both antigen-binding sites from both antibodies are expressed and functional.

FIG. 50 is schematic of the strategy for detection of soluble proteins. An antigen composed of two or more epitopes is detected using two antibodies, one bound to beads (or any support that binds to multiple antibodies) and the second antibody is expressed by the emittor cell. The antigen is incubated with the antibody-coated bead, decorating its surface with multiple antigens. The bead is them presented to the emittor cell. Because the antigen is crosslinked by the bead, the emittor cell antibodies are crosslinked and light emission stimulated.

FIG. 51 is a graph depicting the results of antibody 6E10-10, crosslinked to Protein G magnetic beads, which was incubated with varying amounts of BoNT/A Hc for 3 hours at 4° C. Beads were washed with CO2I medium three times. Emittor cells expressing 6B2-2 antibody were added, the reaction was spun for 5 seconds, and the light output was monitored in a luminometer.

FIG. 52 is a schematic of the detection of a chemical. A peptide is isolated that binds specifically to the chemical of interest, and an antibody generated that binds specifically to the peptide-chemical complex. If the peptide-chemical only forms a single functional epitope, an additional epitope can be incorporated into the peptide. As shown, this epitope is a digoxigenin molecule, but any specific epitope would suffice. In the presence of chemical, the chemical-peptide complex would comprise two antibody-binding sites, and could be detected in a similar manner as protein toxins.

FIG. 53 is a schematic depicting an alternative method for detecting a chemical. Two peptides are isolated that bind in tandem to the chemical of interest. The binding of these peptides could be detected by generating antibodies against each peptide-chemical complex, or by tagging the peptides with antibody binding sites as shown.

Figure 54:
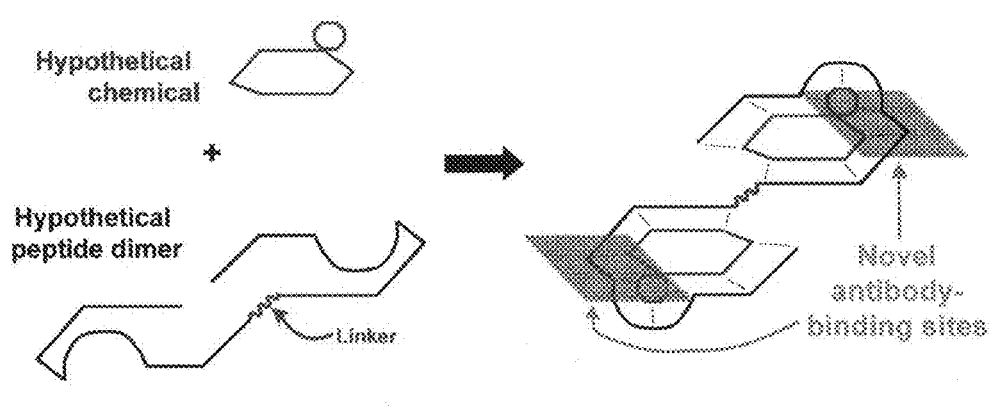

FIG. 54 is a schematic of another alternative method for detecting a chemical. A peptide that binds to two chemicals of interest is prepared which forms a chemical-peptide dimer complex. An antibody is prepared that binds specifically to the chemical-peptide dimer complex. The chemical-peptide dimer complex can contain two antibody binding sites sufficient to stimulate emittor cells to increase intracellular calcium, thereby resulting in photon emission by the emittor molecule.

DETAILED DESCRIPTION OF THE INVENTION

The invention described herein provides methods for detecting soluble antigens. For example, the soluble antigen can be a soluble protein or a chemical. In one embodiment, the soluble antigens comprise only one or two antigenic epitopes. Detection of soluble antigens using an antibody expressed on the surface of a cell, whereby binding of the antibody to the antigen triggers an increase in calcium concentration which in turn stimulates an emittor molecule to emit a photon in response to the increase in intracellular calcium depends on the ability of the antigen to crosslink (or aggregate, thereby immobilizing the antibody on the cell surface) the antibodies on the cell surface, thereby stimulating an increase in intracellular calcium. A soluble antigen can be inefficient at crosslinking antibodies expressed on the surface of a cell, and therefore is inefficient at stimulating an increase in intracellular calcium. Described herein are methods for detecting a soluble antigen wherein crosslinking of antibodies is achieved by the methods described, which stimulate an increase in intracellular calcium and cause emission of a photon from an emittor molecule that responds to the increase in calcium concentration.

The soluble antigens and chemicals of interest to be detected include a wide variety of agents. For example, and without limitation, the methods of the invention described herein can be used to detect protein toxins such as Botulinum toxins, serotypes A, B, C, D, E, F, G, Staphylococcal enterotoxin-B (SEB) and other superantigens, ricin, pertussis toxin, Shiga toxin, conotoxins, *Clostridium perfringens* epsilon toxins, Shiga-like ribosome inactivating proteins, other soluble bacterial products, such as F1 antigen from *Y. pestis*, protective antigen, Lethal factor, edema factor from *B. anthracis*. Other molecules of interest in detecting include bacterial quorum sensing molecules, e.g., homoserine lactones. Examples of chemical warfare agents, or their breakdown products after hydrolysis that can be detected using the methods described herein include, without limitation, cyanide (Hydrocyanic acid), Phosgene (Carbonic dichloride), CK (Cyanogen chloride), CL (Chlorine), CX (Carbonimidic dichloride, hydroxy), DP (Carbonochloridic acid, trichloromethyl ester), GA, Tabun (Dimethylphosphoramidocyanidic acid, ethyl ester), GB, sarin 9Methylphosphonofluoridic acid, (1-methylethyl)ester), GD, Soman (Methylphosphonofluoridic acid, 1,2,2-trimethylpropyl ester), GF (Methylphosphonofluoridic acid, cyclohexyl ester), Mustard (1,1'-Thiobis[2-chloroethane]), HN-1, Nitrogen Mustard (2-Chloro-N-(2-chloroethyl)-N-ethylethanamine), HN-2, Nitrogen mustard (2-Chloro-N-(2-chloroethyl)-N-methylethanamine), Lewsite ((2-Chloroethenyl) arsonous dichloride), PFIB (1,1,3,3,3-pentafluoro-2-trifluoromethyl-1-propene), Triphosgene (Carbonic acid, trichloromethyl ester), V-gas (Methylphosphonothioic acid, S-[2-(diethylamino)ethyl]O-2-methylpropyl ester), VX (Methylphosphonothioic acid, S-[2-[bis(1-methylethyl)amino] ethyl]O-ethyl ester), binary components of VX (O-Ethyl O-2diisopropylaminoethyl methylphosphonite and Sulfur), binary components of GD (Methylphosphonyl difluoride (DF) and a mixture of pinacolyl alcohol and an amine, binary components of GB (Methylphosphonyl difluoride (DF) and a mixture (OPA) of isopropyl alcohol and isopropyl amine. Additionally, other biologically-derived chemicals can also be detected by the methods of the present invention, including Mycotoxins, particularly trichothecene (T2) mycotoxins, Diacetoxyscirpenol Diverse group, Saxitoxin, or other dinoflagellage products, Microcystins (various types), Palytoxin, Satratoxin H, Aflatoxins, and Tetrodotoxin.

Additional proteins of interest to detect include, APP (Amyloid Precursor Protein), prion proteins associated with CJD, BSE, Scrapie, Kuru, and PSA (prostate specific antigen). Furthermore, the detection of appropriate soluble antigens or chemicals is useful in a variety of applications, such as clinical applications, for example, thyroid function, adrenal function, bone metabolism, fertility, infertility, IVF, pregnancy, growth and growth hormone deficiency, diabetes, hematology, cardiac function, cancer, allergy, autoimmune diseases, therapeutic drug monitoring, drugs of abuse, research immunoassay applications, genetically engineered proteins, milk drug residue, liver function, antibiotics and antibiotic synthesis pathways. Suitable soluble antigens for analysis in these applications are known by those of skill in the art (see, for example, The Immumoassay Handbook" (second edition), David Wild, ed. Nature Publishing Group 2001. NY N.Y.).

The present invention also provides for the detection and identification of specific nucleic acid (NA) sequences. In one embodiment, antigens are attached to the target NA using oligonucleotide probes. These probes decorate specific NA sequences with antigen(s). This antigen-decorated (also referred to herein as antigen-conjugated) oligonucleotide is capable of stimulating emittor cells expressing antibody against that antigen. Free probe, if present, is monomeric, and therefore does not stimulate emittor cells. Likewise, background binding of labeled oligonucleotide to nonspecific sites on NA will not significantly stimulate the emittor cells, because the antigens resulting from these rare background binding events will be too disperse to effectively crosslink antibodies.

The choice of antigen depends on many factors, including the availability and characteristics of corresponding antibodies, the absence of crossreactive antigens in the samples to be tested, and the solubility, stability, and cost of the antigen-oligonucleotide conjugate, as will be understood by one of skill in the art. As used herein, an oligonucleotide can be DNA, RNA, peptide nucleic acid (PNA), locked nucleic acids, or any variety of modified nucleic acid surrogates that have specialized and unique characteristics as is known in the art. Additionally, the addition of cationic amino acids (in peptide or protein form) to such probes can increase hybridization rates. If desired, those cationic peptides/proteins could serve double-duty as the antigen detected by the emittor cell. Therefore, in one embodiment of the invention, a detection system based on emittor cells having one or more antibodies on their surface and comprising a compound (an emittor molecule) that emits a photon upon stimulation by antigens that are multimeric due to the presence of target NA, in particular, photon emission is stimulated by an increase in intracellular calcium concentration.

Also provided in the invention described herein is a sensor cell that detects a target particle that is bound by one or more antibodies. Specifically, the sensor cells comprise an emittor molecule and an Fc receptor that binds to an antibody which is bound to the target agent or particle. In one embodiment, the sensor cell comprising an Fc receptor is a macrophage cell, such as the human macrophage cell line U937. Other suitable cells or cell lines will be known to those of skill in the art. The Fc receptors are a family of membrane-expressed proteins that bind to antibodies or immune complexes. They are expressed on several hematopoietic cells including monocytes and macrophages. Several subclasses of Fc receptors exist including Fc gamma Receptor I (FcγRI), a high-affinity binder of soluble antibody. FcγRI binds to the constant region (Fc portion) of Immunoglobulin G (IgG) leaving the antigen-binding region of the antibody free. Crosslinking of the antibody-bound Fc receptor by specific antigen initiates a signaling pathway that stimulates calcium release. Therefore, crosslinking of the Fc receptor on the sensor cell results in an increase in intracellular calcium concentration and the emittor molecule thereby emits a photon in response to the increase in calcium concentration.

Also provided in the invention described herein is a 16-Channel Sensor. In its simplest form, an emitter cell assay consists of preparing a sample in a transparent tube, introducing an aliquot of specially prepared emitter cells into the tube, driving the emitter cells to the bottom of the tube using a quick centrifugal spin, and measuring the light output from the tube with a photon-counting sensor. In the laboratory, most emitter cell assays are made sequentially, one sample at a time; in the automated BAWS/CANARY instrument, four samples are measured simultaneously, each sample having its own light-gathering channel. The former system requires more time, while the latter requires more-complex (and expensive) hardware.

Figure 39:
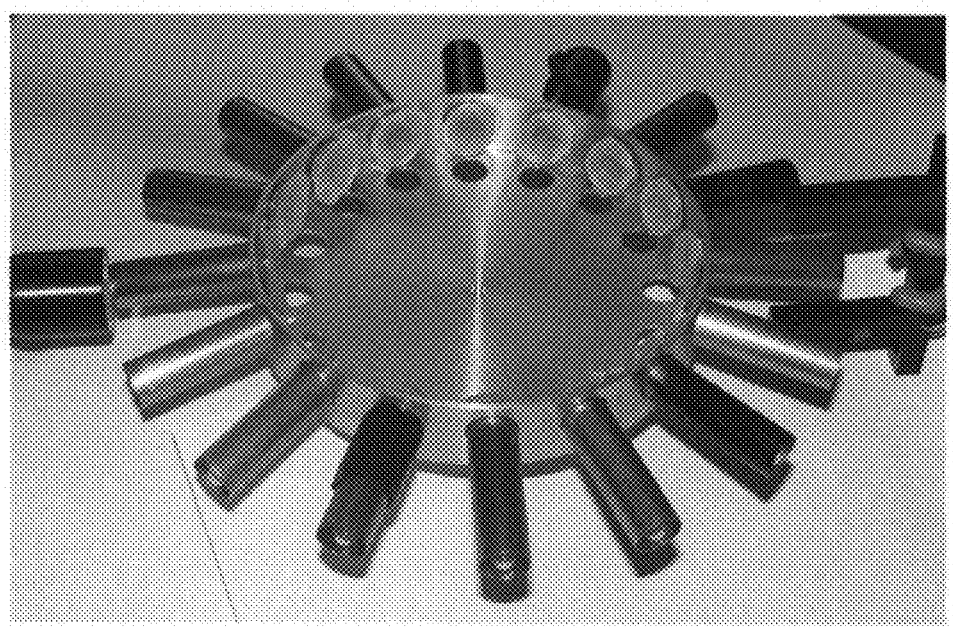

A different approach that reduces the time to measure multiple samples (while keeping the hardware requirements minimal) is described herein. A sensor has been designed that allows the simultaneous measurement of a plurality of samples using a single light-gathering channel. The sensor consists of a rotor holding sixteen 1.5-ml tubes horizontally, equally distributed about its circumference, and driven by a variable speed motor about a vertical axis (FIG. 39). A single fixed photon-detecting element (for example, a PMT) is positioned in the plane of the rotor just beyond the path of the tubes during rotation. In this design, each of the tubes is sequentially and repetitively brought into close proximity to the photon-detecting element, allowing its light output to be sampled on each pass. Finally, an optical switch consisting of an optical source (an infrared LED) and a detector (a phototransistor) is used to control the counting of detected photons and the reorganization of the data into the 16 fields, each associated with a specific sample.

Figure 42:
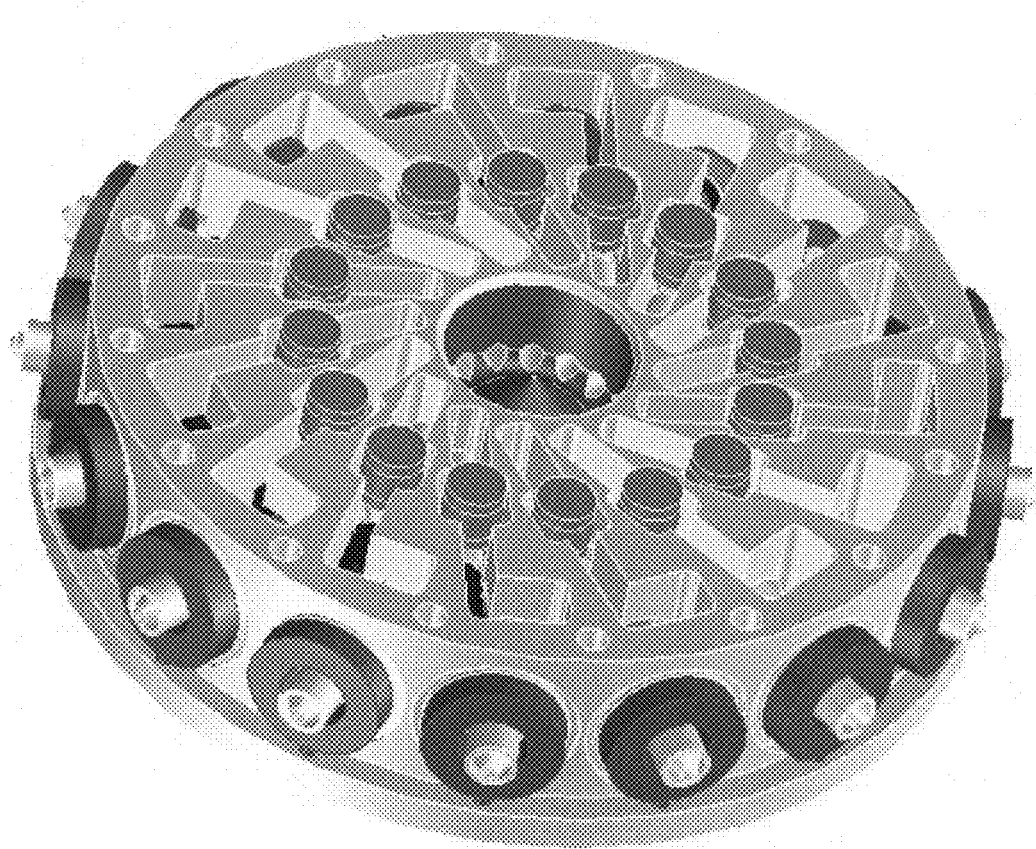
Figure 43:
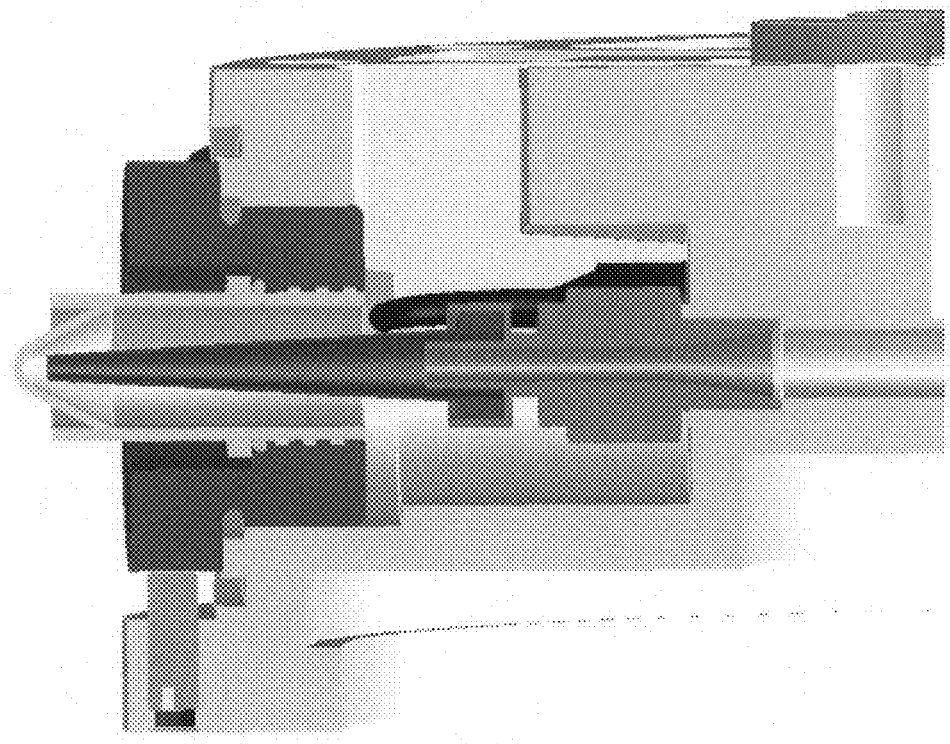

A further implementation of this 16-channel design is referred to as a TCAN sensor. The TCAN (Triggered-CANARY) biosensor is an automated biosensor which combines both aerosol collection and emitter cell liquid delivery into an integrated radial disc format. The TCAN CANARY disc (CD) (FIG. 42) interfaces with a manifold assembly which splits an air flow into separate channels. The aerosol collection assembly (FIG. 43) uses dry impaction techniques to then localize particles from the air flow into the bottom of clear plastic tubes.

After impaction of aerosol particles, the CD interfaces with the manifold assembly to actuate valves located in the disc. The disc is rapidly spun, which in turn causes the emittor cell liquid to deliver to individual tubes using centrifugal force (FIG. 44). An optical detector is then used to identify potential bioagents based on the photon output of emittor cells interacting with the aerosol particles. This process of aerosol collection and emittor cell delivery can be repeated several times in one disc. This feature allows multiple emittor cell assays to be performed after several trigger events without changing the CD.

The materials and procedures suitable for use in the invention are described in further detail below.

Emittor Cells

The emittor cell (also referred to herein as a sensor cell or a CANARY cell) can be any prokaryotic or eukaryotic cell that has a suitable receptor, signaling pathway, and signal output method, either naturally, through genetic engineering, or through chemical addition. The cell can be an artificial or nonliving unit provided that it has a functional receptor, signaling pathway, and signal output method. Upon binding of antigen receptor, such as to the antibodies, the cell mobilizes calcium ions into the cytosol. An example of a cell useful in the device and methods of the invention is a B cell (i.e., a B cell from a cold or warm-blooded vertebrate having a bony jaw) which can be genetically engineered to express one or more surface-bound monoclonal antibodies. Another example of a cell useful in the device is a macrophage cell, such as the human cell line U937, which expresses an Fc receptor on the cell surface. An antigen can be bound to an antibody by addition of the antibody to the target and this antigen-antibody complex will bind to the Fc receptor on the cell and stimulate signaling which results in an increase in intracellular calcium.

A monoclonal antibody can be produced by, for example, immunizing an animal with the antigen to be detected and harvesting the B cell from the immunized animal. DNA encoding the monoclonal antibody can then be isolated and transferred into an immortalized cell line and the cells screened for production of a surface monoclonal antibody specific for the antigen to be detected. B cells are useful for both qualitative and quantitative analyses, particularly because the emission signal from them typically does not significantly diminish as additional target specimen is exposed to it and also because such emission signal is linear.

Alternatively, the cell can be a fibroblast. However, fibroblasts do not contain the signal transduction machinery necessary to transfer a signal from the cytoplasmic portion of a surface antibody to calcium stores in the cell. To overcome this problem, a chimeric surface antibody can be expressed in the fibroblast. This chimeric antibody contains a cytoplasmic amino acid sequence derived from a polypeptide (e.g., a fibroblast growth factor receptor) that can transduce a signal from the inner surface of the plasma membrane of the fibroblast to intracellular calcium stores. Thus, when an antigen binds to the extracellular portion of the chimeric antibody to cause antibody aggregation on the surface, calcium mobilization is induced. A similar strategy using chimeric antibodies can be employed for any other cell type which is not a B cell, so that the cell is suitable for use in the devices and methods of the invention.

Cells useful in the devices and methods herein are those designed to recognize a specific substance, including those having receptors on their surface that specifically bind to that substance. A preferred receptor is an antibody or single-chain antibody, although other suitable receptors include a mitogen receptor (such as a lipopolysaccharide (LPS) receptor), a macrophage scavenger receptor, a T cell receptor, a cell adhesion molecule, a DNA binding protein such as part of a sequence-specific restriction enzyme or transcription factor, single-stranded-RNA- or double-stranded-RNA-binding protein, an oligonucleotide complementary to a DNA or RNA sequence to be recognized, or other ligand-binding receptor (e.g., Fas; cytokine, interleukin, or hormone receptors; neurotransmitter receptors; odorant receptors; chemoattractant receptors, etc.) that will specifically bind the substance to be recognized. The receptor can be attached to the cell surface via a transmembrane domain, a membrane-bound molecule that specifically binds to the receptor (such as Fc receptors bind to antibodies), or a covalent or noncovalent attachment (e.g., biotin-streptavidin, disulfide bonds, etc.) to a membrane-bound molecule. The receptor can also be a chimeric molecule; for instance, it can have an extracellular domain such as an antibody, single-chain antibody, lectin or other substance-specific binding domain or peptide, and an intracellular domain such as that from the insulin receptor, fibroblast growth factor, other protein that triggers a second messenger cascade, etc. Instead of directly binding to the substance to be recognized, the receptor might specifically bind to another molecule or object that in turn specifically binds to the substance to be recognized, such as a secondary antibody, labelled bead, antigen-conjugated oligonucleotide, etc.

Alternatively, only one of these binding steps may need to be specific. For instance, DNA or RNA containing specific sequences may be pulled out of solution using oligonucleotide probes conjugated to one antigen (or directly to a bead, or on a matrix), and a second set of nonspecific antigen-conjugated oligonucleotide probes annealed to the target DNA/RNA would be used to stimulate cells specific for that second antigen. Also, non-specific nucleic acid binding proteins (histones, protamines, RNA-binding proteins) expressed as chimeras on the cell surface, or antibodies against those binding proteins, could also be used to detect the presence of nucleic acids after a sequence specific selection step.

Antibodies

Whatever original cell type, the antigen-binding variable regions of monoclonal antibodies can obtained either as DNA sequence from a public source, or cloned by RT-PCR from a hybridoma cell line. RT-PCR is accomplished using sets of primers designed to anneal, at the 5-prime end, to either the leader or framework regions of the variable region, and at the 3-prime end to the constant region.

The antibody variable regions are then cloned into expression vectors that already contain the constant regions for light and heavy chain. The light chain expression vector described in Persic et al., Gene 187:9-18, 1997 is especially suitable for this purpose. VKExpress, described in Persic et al., contains the EF-1α promoter, a leader sequence, multiple cloning sites, and the human Ig kappa constant region and polyadenylation signal. The heavy chain expression vector is derived from Invitrogen's pDisplay. This vector contains a CMV promoter, a leader sequence, an HA tag, multiple cloning site, and myc tag, followed by the PDGFR transmembrane domain and bovine growth hormone polyadenylation signal.

pDisplay can be modified for heavy chain expression as follows. The PDGFR transmembrane domain of pDisplay is replaced with the murine IgM constant region without the exon that allows for secretion. This ensures that the protein will remain membrane-bound. The neomycin-resistance gene can be replaced by any of a number of antibiotic-resistance genes including, but not limited to, hygromycin, bleomycin, puromycin, kanamycin, and blasticidin genes. The heavy chain (or alternatively light chain) variable region can be inserted in a two-step process, using overlap-extension PCR, to remove the HA and myc tags present on either side of the multiple cloning site of pDisplay. A vector can also be developed to allow insertion of an overlap extension product containing the variable region fused to approximately 300 base pairs of the IgM constant region, so that cloning can be done in a single step.

The examples below were implemented using the antibody vector construction procedure described immediately above.

An antibody which specifically binds to the antigen to be detected is a molecule which binds to the antigen or an epitope of the antigen, but does not substantially bind other antigens or epitopes in the sample. Such antibodies can be chimeric (i.e., contain non-antibody amino acid sequences) or single chain (i.e., the complementarity determining region of the antibody is formed by one continuous polypeptide sequence).

Alternatively, surface antibody-producing cells can be obtained from the animal and used to prepare a monoclonal population of cells producing surface antibodies by standard techniques, such as the hybridoma technique originally described by Kohler et al., Nature 256:495-497 (1975); Kozbor et al., Immunol Today 4:72 (1983); or Cole et al., Monoclonal Antibodies and Cancer Therapy, Alan R. Liss Inc., pp. 77-96 (1985). The technology for producing cells expressing monoclonal antibodies is well known (see, e.g., Current Protocols in Immunology (1994) Coligan et al. (eds.) John Wiley & Sons, Inc., New York, N.Y.), with modifications necessary to select for surface antibodies rather than secreted antibodies.

Any of the many well known protocols used for fusing lymphocytes and immortalized cell lines can be applied for the purpose of generating a cell producing a surface monoclonal antibody (see, e.g., Current Protocols in Immunology, supra; Galfre et al., Nature 266:55052, 1977; Kenneth, In Monoclonal Antibodies: A New Dimension In Biological Analyses, Plenum Publishing Corp., New York, N.Y., 1980; and Lemer, Yale J Biol Med 54:387-402 (1981). Moreover, the ordinarily skilled worker will appreciate that there are many variations of such methods which also would be useful.

Polyclonal cells expressing antibodies can be prepared by immunizing a suitable animal with the antigen to be detected. The cells producing antibody molecules directed against the antigen can be isolated from the animal (e.g., from the blood) and further purified by well-known techniques, such as panning against an antigen-coated petri dish. As an alternative to preparing monoclonal cells, a nucleic acid encoding a monoclonal antibody can be identified and isolated by screening a recombinant combinatorial immunoglobulin library (e.g., an antibody phage display library) with the antigen to thereby isolate immunoglobulin library members that bind the antigen. Kits for generating and screening phage display libraries are commercially available (e.g., the Pharmacia Recombinant Phage Antibody System, Catalog No. 27-9400-01; and the Stratagene SurfZAP® Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al., Bio/Technology 9:1370-1372 (1991); Hay et al., Human Antibod Hybridomas 3:81-85 (1992); Huse et al., Science 246:1275-1281 (1989); Griffiths et al., EMBO J. 12:725-734 (1993).

After the desired member of the library is identified, the specific sequence can be cloned into any suitable nucleic acid expressor (e.g., a vector) and transfected into a cell such as a fibroblast. The expressor can also encode amino acids operably linked to the antibody sequence as appropriate for the cell which is to express the antibody. As discussed above, the cytoplasmic transmembrane sequence of a fibroblast growth factor receptor can be linked to a single-chain antibody specific for the antigen to be detected, so that the cell immobilizes calcium when contacted with the antigen. Although separate recombinant heavy chains and light chains can be expressed in the fibroblasts to form the chimeric antibody, single chain antibodies also are suitable (see, e.g., Bird et al., Trends Biotechnol 9:132-137, 1991; and Huston et al., Int Rev Immunol 10:195-217, 1993).

Photon Emitter Molecules

Binding of the desired substance to the cell-surface receptor should trigger a signaling pathway inside the cell. A preferred signaling pathway is the second-messenger cascade found in B cells, T cells, mast cells, macrophages, and other immune cells, wherein crosslinking of the cell surface receptors activates a tyrosine kinase, which then phosphorylates phospholipase C, which then cleaves phosphatidylinositol 4,5-bisphosphate (PIP2) into inositol 1,4,5-trisphosphate (IP3) and diacylglycerol; IP3 then opens calcium channels to release calcium from intracellular stores such as the endoplasmic reticulum or to let in extracellular calcium, thereby elevating the calcium concentration in the cell's cytosol. Depending on the receptor type, cell type, and desired signaling method, alternative second-messenger cascades could be employed, such as a G-protein-adenylyl cyclic-cAMP-protein kinase A cascade.

A method should be provided for monitoring the internal signaling of the cell in response to substances to be identified. If the internal signaling involves an increase in cytoplasmic calcium, a preferred detection method is a calcium-sensitive luminescent or fluorescent molecule, such as aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA, cameleons (A. Miyawaki et al., (1999) Proc. Natl. Acad. Sci. 96, 213540), or similar molecules. It is anticipated that the relative intensities of light and the sensor cell storage characteristics enabled by using calcium-sensitive molecules may vary depending on the efficiency of light production for the specific emitter molecule and the half-life of the activated emitter molecule—in some cases providing significant benefits (e.g., improved sensitivity, quantitative or qualitative detection). Additional performance enhancements may arise from the use of structural analogs of the natural cofactors of photoprotein emitter molecules. Various calcium-sensitive fluorescent dyes which can be taken up by live cells are available from commercial sources, including Molecular Probes, Inc., Eugene, Oreg. Proteins such as aequorin, obelin, thalassicolin, mitrocomin (halistaurin), clytin (phialidin), mnemopsin, berovin or cameleons could be added genetically, injected into the cells, or delivered by a protein uptake tag from HIV TAT (approximately amino acids 47-57; A. Ho et al. (2001) Cancer Research 61, 474-477) or by other means. If desired, such reporter molecules can include targeting signals to target them to the cytoplasmic face of the endoplasmic reticulum or the plasma membrane, the interior of the mitochondria, or other locations where the change in local calcium concentration might be particularly large. Optical methods of detecting activity from other points in the signaling pathway could also be used, such as fluorescence resonance energy transfer (FRET) of fluorescent groups attached to components of the signaling pathway (S. R. Adams et al. (1991) Nature 349, 694-697). Where the internal signaling involves an increase in reactive oxygen species (e.g. superoxide anion radicals, hydroxyl radicals, compound I or II of horseradish peroxidaase, etc.), a preferred detection method is a reactive-oxygen-sensitive luminescent or fluorescent molecule, such as the photoprotein pholasin (a 34-kDa glycoprotein from the bioluminescent mollusc, Pholas dactylus) or similar molecules. Alternatively, a reporter gene for any luciferase could be linked to a promoter induced by the signaling pathway. In some cells such as T cells and mast cells, the signaling pathway triggers exocytosis of granules containing proteases such as granzymes, tryptases, or chyrnases. Exocytosis of these proteases could be detected by calorimetric or fluorometric methods (e.g., p-nitroanaline or 7-amino-4-trifluoromethyl coumarin (AFC) linked to peptides cleaved by the proteases [S. E. Lavens et al. (1993) J. Immunol. Methods 166, 93; D. Masson et al. (1986) FEBS Letters 208, 84; R&D Systems]). Also, microelectrodes or other methods to detect the electrical activity associated with the calcium flux or other signaling ion fluxes are suitable to monitor signaling response in the cell.

A suitable emitter molecule is any molecule that will emit a photon in response to elevated cytosolic calcium concentrations, including bioluminescent and fluorescent molecules. One emitter molecule, the bioluminescent aequorin protein, is described in Button et al., Cell Calcium 14:663-671 (1993); Shimomura et al., Cell Calcium 14:373-378 (1993); and Shimomura, Nature 227:1356-1357 (1970). Aequorin generates photons by oxidizing coelenterazine, a small chemical molecule. Coelenterazine diffuses through cellular membranes, so coelenterazine or an analog thereof can be added to the culture medium surrounding the cells. Alternatively, genes encoding enzymes that make coelenterazine can be introduced into the cells. In another embodiment, bioluminescent green fluorescent protein (GFP) (see Chalfie, Photochem Photobiol 62:651-656 [1995]) or yellow fluorescent protein (YFP) can be used. In this embodiment, the cell cytosol contains both GFP and aequorin. In response to elevated calcium in the cytosol, aequorin donates energy to GFP in an emissionless energy transfer process. GFP then emits the photon. Alternatively, the emitter molecule can be a calcium-sensitive fluorescent molecule (e.g., indo-1) which is illuminated by a wavelength of light suitable to induce fluorescence.

Aequorin, or any other emitter molecule, can be introduced into the cell by methods well known in the art. If the emitter molecule is a protein (as is the case with aequorin), the cell can contain an expression vector encoding the protein (i.e., a nucleic acid or virus which will produce the emitter molecule when introduced into a cell). An expression vector can exist extrachromosomally or be integrated into the cell genome.

Conjugated Antigens/Tags

One or more antigens or tags can be added (also referred to herein as conjugated) to molecules to provide a known antigenic epitope. For example, one or more antigens can be conjugated to an oligonucleotide to produce an antigen-conjugated oligonucleotide with a known antigenic epitope. An antigen-conjugated molecule can comprise one antigen or multiple antigens that are either the same of different. For example and without limitation, an antigen or tag to be conjugated to a molecule for detection includes small antigens such as digoxigenin, digoxin, phosphocholine, fluoroscein or other fluorophores, and biotin, and peptides such as HIS, VSV-G, FLAG, and C(AAKK) multimer (as described in Corey, J. Am. Chem. Soc., (1995) 117: 9373-4).

Oligonucleotides

In addition to conventional DNA and RNA probes, a variety of modified nucleic acids have been shown to hybridize in a sequence-specific manner to target nucleic acid sequences. These include peptide nucleic acids (PNA) (Nielsen et al., (1991) Science 254: 1497-1500), Bis-PNAs (Griffith et al., (1995) J. Am. Chem. Soc 117: 831-832), Tail-clamp PNA (Bentin (2003) Biochemistry 42: 13987-13995), PD loops (Bukanov et al., (1998) PNAS 95: 5516-5520), PNAs incorporating pseudocomplementary bases (Lohse et al., (1999)

PNAS 96 (21) 11804-11808), or locked nucleic acids (Braasch and Corey (2001) Chem. Biol. 8: 1-7). A variety of these modified nucleic acids have been shown to have differ in hybridization characteristics, stability, affinity, and specificity, and could be used in place of conventional DNA oligonucleotides (reviewed by Beck and Nielsen, pp. 91-114, in Artificial DNA: Methods and Applications. CRC Press, Y. E. Khudyakov and H. A. Fields eds.). Attachment of cationic proteins, peptides, or DNA binding proteins has been shown to improve hybridization kinetics (Corey (1995) J. Am. Chem. Soc 117: 9373-9374; Zhang et al., (2000) Nuc. Ac. Res. 27 (17) 3332-3338).

The binding of oligonucleotides has been shown to improve with the addition of helper oligonucleotides (O'Meara et al., (1998) Anal. Biochem. 225: 195-203; Barken et al, Biotechniques (2004) 36: 124-132). Specificity can be improved by addition of unlabeled hairpin competitor probes (Huang et al., (2002) Nucleic Ac. Res. 30: (12) e55).

Removal of unbound oligonucleotides after hybridization to target is not necessary for nucleic acid sequence detection, but may be desirable. The unbound labeled oligonucleotide could be removed using a variety of conventional chromatography techniques, including size exclusion, hydrophobic interaction, or ion exchange, depending on the chemistry of the particular probe used.

Other Nucleic Acid-Binding Molecules

Oligonucleotides are not the only molecules that are able to identify specific nucleic acid sequences. Proteins are also capable of such discrimination, and can be expressed on the surface of the emitter cell, recombinantly attached to a cytoplasmic domain that would, upon binding, initiate a calcium response. This would include nucleic acid binding proteins attached to the Fc portion of antibodies, for example. Expression of nucleic acid binding proteins on the surface of the emitter cell would eliminate having to denature double-stranded nucleic acid prior oligonucleotide hybridization, and additionally, the system produces all the necessary components: no exogenously synthesized oligonucleotides would be required. Possible sequence specific DNA binding proteins include: (1) DNA restriction enzymes (preferably with the DNA-cutting catalytic site removed or inactivated, e.g. L. F. Dorner & I. Schildkraut (1994) Nucl. Acids Res. 22, 1068-1074); (2) Transcription factors or other specific DNA- or RNA-binding proteins, especially those that recognize unique DNA or RNA sequences in pathogens or organisms of interest (e.g., HIV TAT transcription factor: C. Brigati et al. (2003) FEMS Microbiology Letters 220, 57-65; poxvirus transcription factors: S. S. Broyles (2003) Journal of General Virology 84, 2293-2303). Emitter cells with such receptors could be designed to crosslink on target DNA/RNA with either a specific repeated sequence or alternatively two or more unique sequences.

Capture Oligonucleotides

Although not necessary for detection, capture of the target nucleic acid sequence on sedimentable or solid support can improve assay sensitivity. Single-stranded DNA target can be captured using, for example, biotin-labeled capture oligonucleotides bound to streptavidin-coated polystyrene or paramagnetic beads. The captured material can be separated from unbound material by centrifugation or exposure to a magnetic field, as appropriate. The use of an intermediate binding reaction (avidin-biotin) in attaching the oligonucleotide to the bead may not be necessary as any interaction that would attach the oligonucleotide to a solid support can be used, including direct conjugation. In addition, any solid support to which the capture oligonucleotide can be attached would suffice. This can be in the form of a two-dimensional array, in which specific capture oligonucleotides are placed in specific positions on the array. Alternatively, target nucleic acid sequences can be captured in a non-specific manner (e.g. ion exchange resin, precipitation, histone or protamine binding). Target capture will also concentrate the target nucleic acid sequence and/or remove assay interferents.

Polyvalence

Emitter cell stimulation is dependent on the antigen appearing multivalent to the emitter cell. In general, this can be accomplished in at least two ways. First, multiple copies of antigen can be attached to a target molecule, for example, hybridizing multiple antigen-conjugated oligonucleotides to the target nucleic acid sequence. Second, several copies of the target nucleic acid sequence, each with a single antigen attached, can be bound to each other or bound in close proximity to each other (e.g., attached to a bead). In this example, the individual target nucleic acid sequence would not be polyvalent, but the bead with multiple copies of the target nucleic acid sequence attached would present a polyvalent antigen.

Reaction Chambers.

The reaction chambers suitable for use in the invention can be any substrate or vessel to which emitter cells and candidate particles can be mixed and contacted to each other. In one embodiment, the reaction vessel is a centrifuge tube (e.g., a microcentrifuge or Eppendorf tube). As described herein, centrifugation is a particularly well-suited means to pellet candidate particles or emitter cells first, before the other is driven into the first pellet. To further increase the pelleting of both particles and cells, the side walls of the tube can be coated with a non-sticky carrier protein such as bovine serum albumin to prevent the sticking of emitter cells to the side walls, and the bottom of the tube can be coated with poly-L-lysine to help ensure that the target particles stay adhered to the bottom of the tube. Other proteins or molecules that either prevent or promote cell adhesion are known in the art of cell biology and are suitable for use in the invention.

Centrifuge tubes with customized sample well geometries can provide an additional embodiment that uses centrifugation to increase emitter cell interactions with difficult-to-sediment particles and reduces the need to customize spin sequence. In this embodiment the particle-containing sample to be analyzed is placed in a tube where the maximum width of the sample chamber is approximately equal to the diameter of an emitter cell. Layering a concentrated emitter cell suspension over the sample followed by centrifuging drives a large number of closely packed emitter cells through the smaller particles while the constrained geometry increases the probability of emitter cell antibody interaction with particles. Binding of the cell-associated antibody to the particle captures the poorly sedimenting particle and will rapidly draw it to the bottom of the tube with the emitter cell where the resulting light can be observed by a photo multiplier device.

In another embodiment, the reaction chambers are wells in a two-dimensional array, e.g., a microtiter plate, or spots or wells along a tape, as shown in the figures. These arrangements allow multiplex detection of either multiple samples and/or multiple target particles. For automated delivery of candidate particles and/or emitter cells, either the reaction chambers or the specimen collector and emitter cell reservoir is addressable in at least two dimensions. The wells of arrays can also be treated with sticky and non-sticky coatings as described above for centrifuge tubes to facilitate contact between emitter cells and candidate particles.

Specimen Collectors

Different devices can be used to collect samples from, e.g., air. In general, an air sampling device has a collection chamber containing liquid through or beside which air or gas is passed through, or containing a porous filter that traps particulates (e.g., target particles) as air or gas passes through the filter. For collection chambers containing liquid, the collection liquid can be centrifuged or otherwise treated to separate particles from the liquid. The separated particles are then deposited in a reaction chamber. For collection chambers containing a filter (e.g., nitrocellulose), the filter or portions of the filter can act as the reaction chamber. Alternatively, particles can be washed from the filter, or the filter can be dissolved or otherwise removed from the particles. A filter collection chamber can also be adapted to collect particles from a liquid (e.g., water supply sample or cerebral spinal fluid) flowing through the filter. In addition, as discussed above, a liquid sample can be centrifuged to remove any particulate material present in the liquid. A variety of samplers are known and available for use with the present invention. See SKC, Inc., which sells the SKC BioSampler® and other sampling devices.

Other air samplers can be used. For example, an alternative device is the Air-O-Cell sampling cassette (SKC, Inc.). In this device, the airborne particles are accelerated and made to collide with a tacky slide which is directly suitable for various staining procedures and microscopic examination.

Aerosol particulates may be collected using inertial separation in a device known as an impactor. An airflow containing particles to be collected is drawn from the environment of interest into the impactor where it is directed towards a surface for impaction. With appropriate geometrical parameters and flow rates in the impactor, particles with sufficient inertia will not follow the flow streamlines, but will impact onto the surface. A significant proportion of the particles impacting the surface adhere through electrostatic and/or van der Waals interactions and are thereby collected and concentrated. In this way, aerosol particles containing proteins (including toxins), viruses, bacteria (vegetative and spore forms), parasites, pollen and other detectable substances can be collected for detection using a variety of available assay technologies including the devices and methods herein.

Dry sample collection for bioassays using an air impactor provides general advantages over traditional air-to-liquid sample collection by reducing or eliminating fluid consumables and transfer mechanisms which reduces assay cost and simplifies automation. Of particular benefit to the devices and methods herein, collection using dry impaction ensures that all of the collected sample is located on the surface prior to the addition of sensor cells of the devices and methods herein, regardless of the size of the individual analyte particles. This achieves localization of all analytes regardless of their sedimentation coefficient in fluid, thereby maximizing the sensitivity of the devices and methods herein and accelerating many implementations of the assay by eliminating a time-consuming step.

Any surface that retains a proportion of particles that impact onto it and that is compatible with subsequent bioassays is suitable as a collection surface. Suitable materials include biocompatible metals, plastics, glasses, crystals, aerogels, hydrogels, papers, etc. Particularly useful configurations of these materials include microcentrifuge tubes, multi-well plates used in high-throughput screening, continuous tapes, filters, conjugate release pads of lateral flow immunoassays, etc. The collection efficiency can be increased by modifications to the collection surface including: the addition of coatings promoting adhesion of biological particles (these coatings can be chemical or biochemical in nature, e.g. polylysine), increased surface roughness to increase the surface area available for collection, and customized surface geometries that promote deposition of particles in defined regions on the surface. Furthermore, additional improvements in collection efficiency can be achieved by manipulating the electrostatic charges on the collection surface and the incoming particles such that additional attractive forces are generated.

Additional improvements can be made to the dry impaction collector by using an air-to-air concentrator upstream of the collector to increase the number of particles in each unit of air sample impacted onto the collection surface. This can significantly reduce the amount of time needed to collect a sufficient number of aerosol particles to provide reliable results for the detector.

In one example of this collection concept, the impactor described in FIG. 23 has been configured to collect aerosol samples on the bottom of a commercially available plastic tube. A nozzle projects down into the tube and the exit is positioned at the radius of curvature of the tube's inner surface. This positioning increases the likelihood of particle impaction upon the tube bottom where the device sensor cells are most likely to contact them. Once collection is completed, a single droplet containing device sensor cells is added directly to the tube containing collected aerosol particles, spun for 5 seconds to accelerate cell delivery to the tube surface, and emitted light is measured using a photon detector (e.g., PMT, CCD, photodiode, etc.). Using this apparatus, dry bacterial spores can be collected from an aerosol and identified directly with optoelectronic device in less than one minute. This method can be implemented with a plurality of tubes used to collect samples and an automated system to conduct subsequent assays. An example of how a system capable of conducting at least 10 independent assays is shown in FIGS. 4, 6, 9, 12, and 15. By implementing an approach where assays are made capable of looking for multiple analytes in a single tube (multiplexed) the number of detectable substances for a single assay cycle can be made greater than the number of available tubes. This can be done by creating individual optoelectronic detection device cell lines expressing a plurality of receptors with affinity for different analytes or by combining multiple cell lines with different specificities in a single tube.

Figure 4:
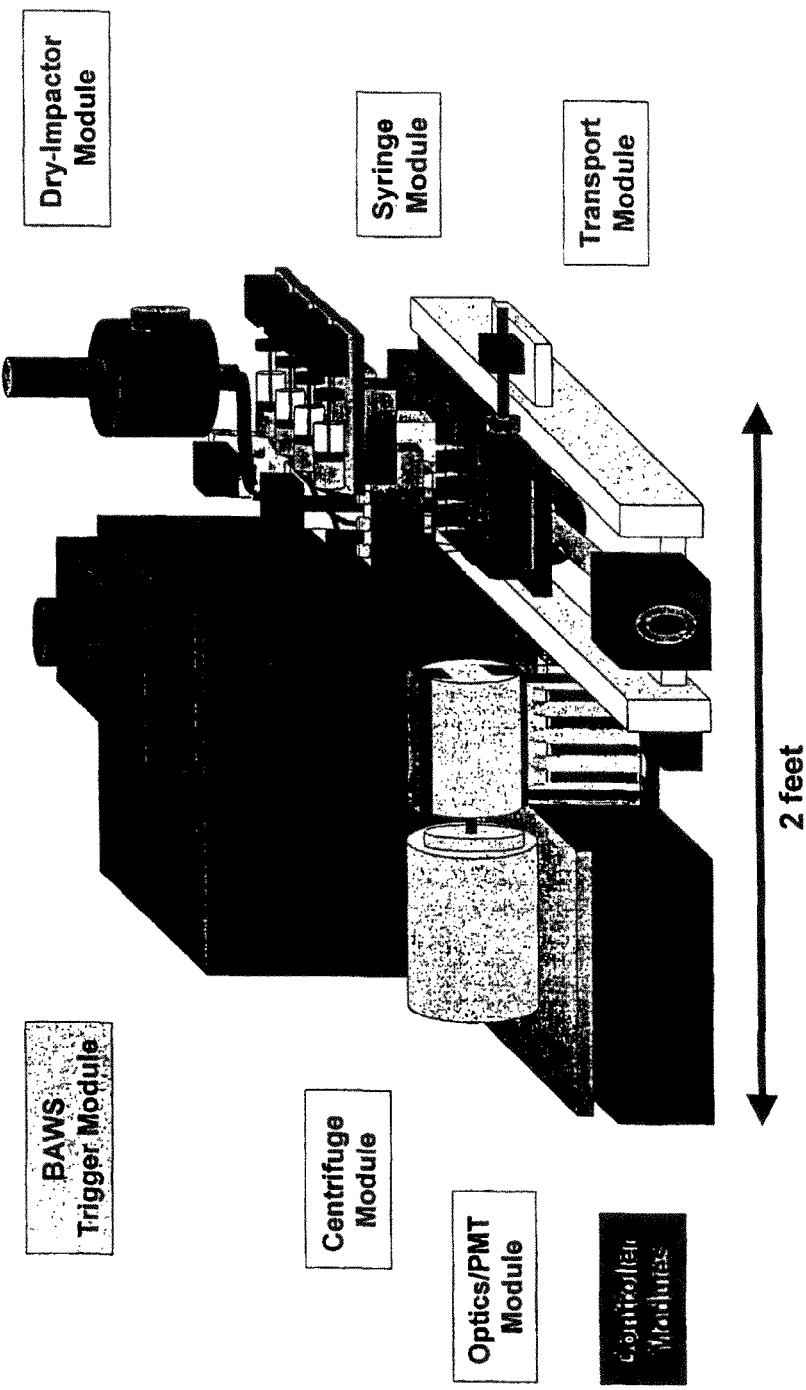
FIG. 4 is a schematic of an integrated biological aerosol warning sensor (BAWS)/optoelectronic sensor system.

FIG. 4 is a schematic of an integrated biological aerosol warning sensor (BAWS)/optoelectronic sensor system. The BAWS trigger module is used to preliminarily detect the presence of particles, e.g., those of a pre-determined size range. If particles meeting specifications are detected, BAWS triggers an air-to-air concentrator that allows particles of a particular size range to be collected and deposited in a well (e.g., reaction chamber, tube) via a dry-impactor module. The dry-impactor module allows for dry sample collection and is in communication with a syringe module for cell (e.g., emitting cells) delivery into a reaction chamber (e.g., tube). A transport module is used to transfer the reaction chamber assembly (having one or more chambers or tubes) to a centrifuge module for sedimentation or mixing of the particle sample and cells. The centrifuge module can be, but need not necessarily be, in communication with an optics/PMT module for detection of photon emission. A controller module is useful for control of operation of the system.

Figure 6:
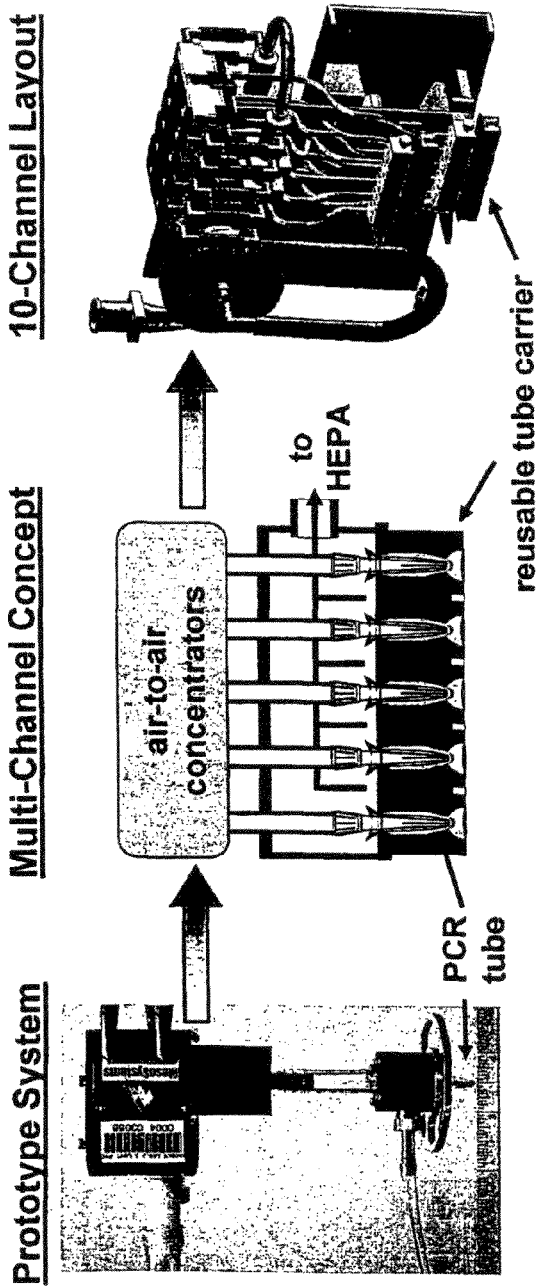
FIG. 6 illustrates a dry-impactor module for the optoelectronic sensor.

FIG. 6 shows an example of a dry-impactor module concept. In this example a single (e.g., prototype system) as well as a multi-channel device is illustrated, including individual sample tubes (e.g., PCR tubes) and tube carriers, in communication with air-to air concentrators from which the particle test sample is collected.

FIG. 9 shows an example of a cell-delivery that can be automated. The sensor cells (e.g., emitting cells) are introduced to the system by means of a syringe and syringe pump arrangement, which can include pipettors or other delivery equipment. This type of assembly allows for multiple and simultaneous introduction of sensor cells to the particle samples (e.g., samples in reaction chambers (e.g., tubes)).

Figure 12:
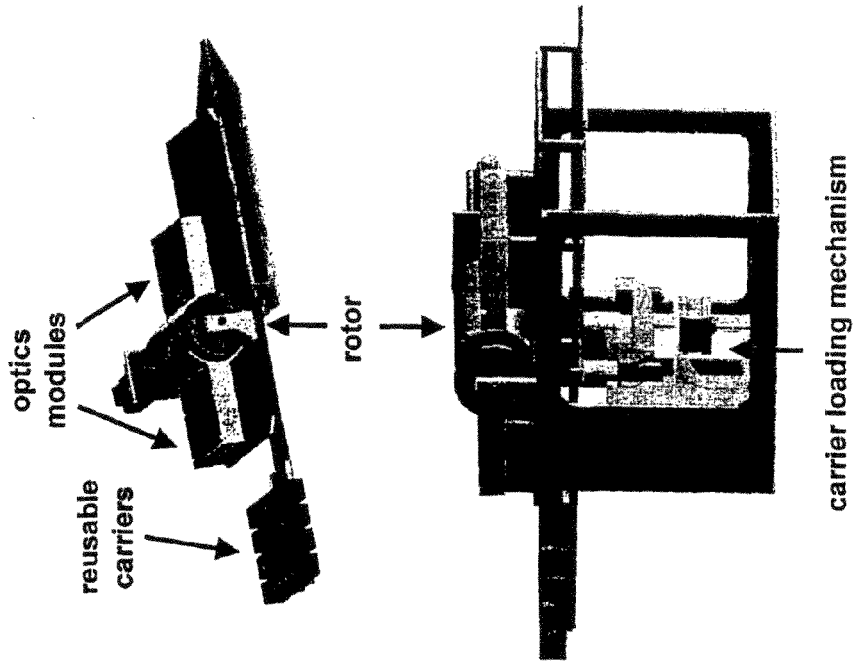

FIG. 12 shows an example of a centrifuge module concept used to spin the particle samples or cell samples. Carriers having the sample tubes are introduced via a loading mechanism into a rotor assembly that is suitable for receiving the carriers. The rotor spins the samples. The rotor assembly is in communication with optics modules for signal collection (e.g., photon emission), and an indexed motor can be used to allow for alignment of the samples chambers with the detector (e.g., optics modules).

Figure 15:
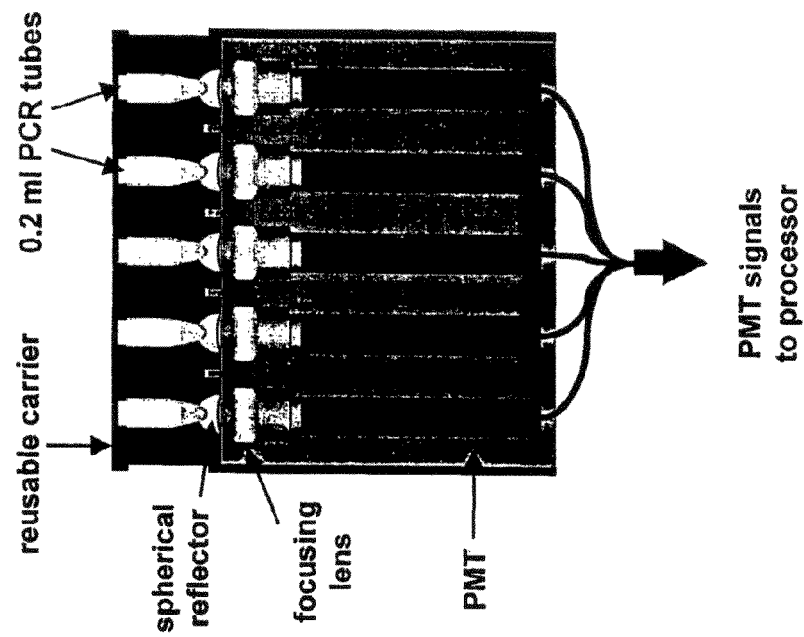
FIG. 15 illustrates an optics-photomultiplier (PMT) module for the optoelectronic sensor.

FIG. 15 shows an example of an optics module. Depending on the precise configuration, the module allows for a plurality of simultaneous testing of samples (e.g., in the reaction chambers, tubes). The carrier and tubes therein are introduced to the unit such that they are in communication with lens assemblies (e.g., integrated reflectors, lenses) if necessary, and ultimately a photodetector (e.g., a PMT). The PMT produces signals that are then sent to a processor for processing and display.

Figure 21:
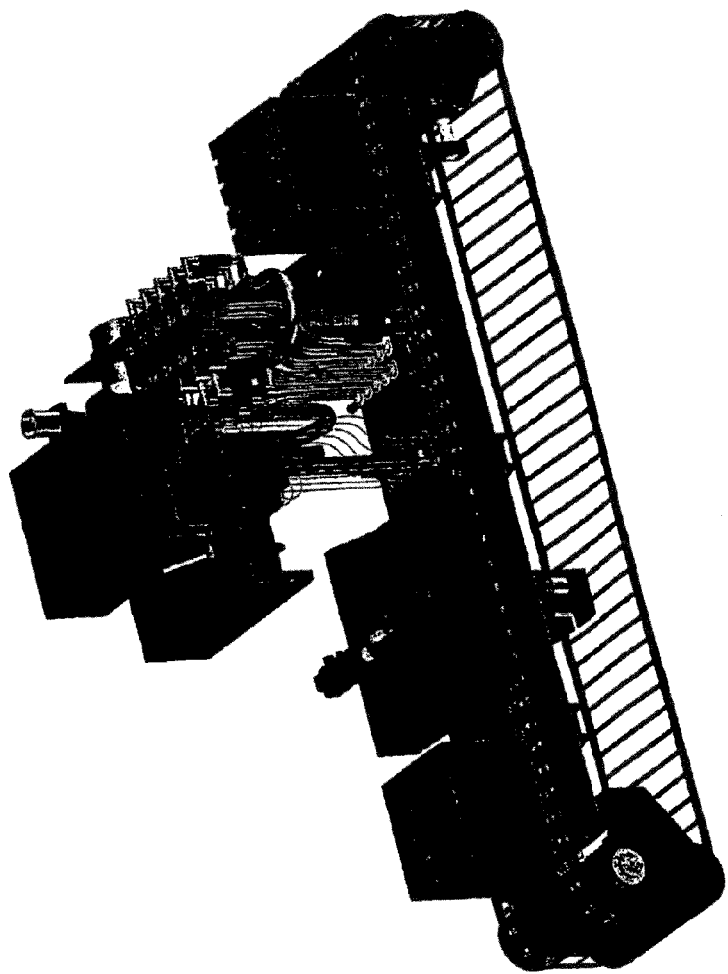
FIG. 21 illustrates an integrated dry-impactor/optoelectronic sensor.

FIG. 21 illustrates an integrated dry-impactor/optoelectronic sensor. In this sensor the modules described above are assembled in a linear arrangement with a cassette holding 30 carriers deliverable to a belt-driven carrier transport module. This transport module moves the assay tubes sequentially from the collector to the cell delivery module to the centrifuge module, and finally to the confirmatory sample storage module following completion of photon detection. The overall size of this integrated sensor is approximately 54 inches wide by 33 inches high by 22 inches deep.

Real-world samples may contain substances that either inhibit the assay (false negative) or cause a response in the absence of specific antigen (false positive). In many instances, these samples can be treated prior to the assay to remove these substances. For example, soluble substances such as detergents or serum factors can be removed by pre-centrifugation step, where the agent is concentrated in the bottom of the tube and the liquid is replaced with assay medium (Portal Shield samples). Insoluble, large particulate substances can be removed from the sample by filtration, using commercial filters of a pore size (3-5 µm) that allows the passage of the agent, but retains the contaminant (diesel or soot samples). Samples can be processed rapidly through syringe filters, adding only a few minutes to the total assay time.

Specimen Localization

As part of the specimen collector or reaction chamber, different mechanisms (other than centrifugation) can be implemented to facilitate contact between emitter cells and candidate particles. For example, the use of electrophoresis, isoelectric focusing, dielectrophoresis, magnetically tagged particles, and the like in bioelectronic devices can be integrated into a system of the invention. See, e.g., U.S. Pat. No. 6,017,696 and other patents assigned to Nanogen, Inc.; Goater et al., Parasitology 117:S177-189, 1998; and U.S. Pat. Nos. 5,512,439 and 4,910,148 and other patents assigned to Dynal AS.

Mixing a aqueous sample containing target particles (particles here can be anything recognized by the emitter cells-proteins/toxins, viruses, bacteria, parasites, nucleic acids, etc.) with an aliquot of media containing emitter cells results in particle-cell contact leading to transient increase in the rate of photon emission. The time between the start of the mixing process and the maximum emission rate depends on the characteristic response of the particular cells to stimulation as well as the time over which the mixing occurs (the mixing time) and the typical time for the particles and cells to come into contact after mixing (the diffusion time).

Because a background rate of detected photons will exist even in the absence of target particles (background cell emission and thermal noise in the photon detector and its electronics, for example), photons emitted from single target-cell interactions can be difficult to distinguish from this background. To be useful as a signal, there must be a significant increase in the rate of photons detected over that of the background. For a given sample, this rate is maximized when the mixing time and diffusion time are minimized. Other possible signals that target particle are present in a sample include: an increase in the total number of photons detected in a period of time above that of the background alone, a change in the statistics of detected photons, or a change in the spectral qualities of the detected photons.

The diffusion time can be minimized by reducing the average distance between particle and cell after mixing. This can be accomplished by localizing the particles and/or cells to within a small volume, often a layer, within the larger mixed volume. However, the time to localize the particles and/or cells may be longer than the characteristic response time of the cells. Mixing between particles and cells over this prolonged localization could produce a lower rate of photon emission, and therefore a lower signal, by increasing the average time between emissions. To avoid this, one or both should be localized separately, while minimizing contact between them. This localization can also lead to a reduced mixing time.

Generally, the means to move particles or cells include the following: sedimentation (by gravity or centrifuge); fluid flow (forced or convective); electric forces (electrophoresis and dielectrophoresis); magnetic forces (using magnetic beads); and acoustics/ultrasonics (standing or traveling waves).

Localization requires a means of moving particles and/or cells combined with a barrier where particles and/or cells can collect, such as the solid surface of a channel or container, the surface of a filter, or the potential energy barrier surrounding an electric-field minimum. Examples include: sedimentation (localizing cells on the lower surface of a chamber); air impaction (impacted particles stick to or settle onto a collection surface); filtering (particles or cells collect on to the surface or into the body of a filter); affinity capture particles or cells can be localized through specific or non-specific binding interactions); magnetic capture (magnetic beads held against a solid surface, a filter surface, or in the body of a filter by localized magnetic forces; beads may or may not have surface chemistry to promote attachment of particles or cells); electrophoresis (charged particles only; collection on to an electrode surface); and dielectrophoresis (positive: collection of particles or cells on to an electrode surface; negative: collection into a region of minimum field).

Localization and mixing of particles and cells can be achieved by combining the above methods, as well as others. In the table below, examples of various localization/detector combinations are provided. Certain of the representative examples illustrate methods to localize particles or cells 2-dimensionally, allowing improvement in sensitivity or discrimination between different particles if an array of photon detectors (including a CCD) is used as opposed to a single photon detector (such as a PMT).

| Example | Method of localizing cells | Method of localizing particles | Mixing: particles or cells/means | Detector |
|---|---|---|---|---|
| centrifuge | centrifuge (short) | centrifuge (long) | cells/sediment (cent.) | single |
| flow cell | sediment and attach to surface | shallow channel above cells | particles/sediment (grav.) | single |
| flow cell (multiple cell lines) | sediment and attach to surface | shallow channel above cells | particles/sediment (grav.) | imaging |
| flow cell/magnetic bead | sediment and attach to surface | localized magnetic bead capture | particles (on beads)/sediment (grav.) | imaging |
| flow cell/electric field | sediment and attach to surface | shallow channel above cells | particles/electrophoresis | single |
| tape/wick | flow (into wick) | air impact (tape) | cells/sediment (grav.) | single |
| air impact | centrifuge (short) | air impact (tape) | cells/sediment (cent.) | single |
| uniprep/magnetic bead | sediment to surface | magnetic beads on filter surface | particles (on beads)/sediment (grav.) | single |
| flow past cells | cells on filter surface | | flow past cells | single |
| counter flow | cells held on filter surface by centrifugation | retained on filter surface | particles/flow past cells counter to cent. Force | single |
| centrifuge tube dielectrophoretic trap | centrifuge onto filter surface | retained in flow by dielectrophorectic force | cells/sediment (cent.) | single |
| traveling-wave dielectrophoresis | sediment and attach to traveling-wave dielectrophoresis | traveling-wave dielectrophoresis | particles/sediment (grav.) | single |
| dissolvable-membrane tube | separate compartment | centrifuge (long) onto dissolvable membrane | cells or particles/traveling-wave dielectrophoresis dissolve membrane and sediment (cent.) | single |
| acoustic/ultrasonic | | | | |

Localization Examples

In each of the following examples, it is assumed, unless stated otherwise. The sample is an aliquot of aqueous solution compatible with short-term cell life and function, possibly containing target particles (though the descriptions below will assume the presence of particles). An aqueous sample can be obtained from environmental, clinical, air-to-liquid, washed-swab, or other samples. An air sample can be obtained from a driven air stream (air sampler or surface pickup), electrostatic capture, or settled airborne particles. References to cells should be understood to mean emitter cells in an aqueous media that is compatible with their life and function. A particle and cell brought into contact is assumed to result in emission of one or more photons. A single or array photon detector exists external to the chamber in which the sample and cells are mixed, and there may be additional optical elements to enhance capture and detection of emitted photons (such as mirrors, lenses, lightpipes, etc.) either external or internal to the chamber. The chambers are either assumed to be transparent in part or in whole or to have another means to allow emitted photons to reach the detector.

Centrifuge

A sample can be centrifuged in a chamber for a time sufficient to sediment the particles. Cells can be introduced to the chamber without disturbing the particles and briefly centrifuged to sediment them onto the particles. Photon detection can occur during or, more typically, after the spin.

Affinity Capture (Surface Capture)

A sample can be introduced into a microcentrifuge tube, multi-well plate, filter unit, or other suitable device where some portion of the surface in contact with the sample has been modified to be able to bind and retain particles that may be present in the sample through specific or non-specific binding interactions. Non-specific binding may be facilitated via electrostatic/ion-exchange interactions, hydrophobic interactions, hydrophilic interactions, etc. Specific binding may be facilitated by immobilizing components to the surface that bind to substrates on the particles (e.g. antibodies, receptors, glycoproteins, proteins, peptides, carbohydrates, oligonucleotides, etc.), or by immobilizing components that are bound by receptors on the surface of particles (small molecules, peptides, proteins, carbohydrates, etc.).

Affinity Capture (onto Mobile Substrate)

Similar to affinity capture on a surface, but particles are bound to mobile substrates (polymer beads, cells, charged molecules, magnetic beads, bacteria, etc.) that provide additional means of moving and/or localizing the particles or cells by various methods including those described herein.

Flow Cell

Emitter cells can be introduced to a shallow flow cell and allowed to attach to the bottom surface; non-adherent cells can be removed by additional flow. A sample is introduced, displacing much of the cell media, and particles can sediment out onto the attached cells. Photons are emitted as particles contact cells.

Flow Cell (Multiple Cell Lines)

Similar to the Flow Cell, with distinct regions of emitter cell sensitive to different target particles. Photon detection by imaging detector to allow identification of which cells are stimulated, and, therefore, which target particles are present in the sample.

Flow Cell (Magnetic Bead)

This is similar to the Flow Cell. Appropriate magnetic beads are mixed with the sample, allowing target particles to attach to the beads. These decorated beads can be introduced to the flow cell where a strong localized magnetic field (due to a permanent magnet or electromagnet) captures them on the surface above the attached cells. Mixing can be initiated by either removing the magnetic force and allow the beads to sediment onto the cells, or moving the magnetic force to attract the beads to the surface to which the cells are attached.

Flow Cell (Electric Field)

Similar to Flow Cell, with the surface to which the cells attach and the one parallel to it being separate electrodes (at least one of which might be transparent). A sample can be introduced, displacing much of the cell media. An appropriate DC voltage is applied between the electrodes and the particles are moved to the attached cells by electrophoresis.

Tape/Wick

An air sample, possibly containing target particles, can be impacted on a transparent surface, which can be rigid or flexible (e.g., a tape), porous or nonporous. An absorbing material, or wick, can be attached, surrounding the impact area or, in the case of a porous surface, on the opposite side of that surface. Cells can be placed on the impact area, and, due to the wick, excess media will be absorbed, reducing the volume and depth of the media bearing the cells and bringing them closer to the particles. Cells sediment out onto the impacted particles or are, additionally, drawn toward them by flow if the surface is porous with the wick material behind.

Air Impact

An air sample, possibly containing target particles, can be impacted into a (fixed and initially empty) chamber which is suitable for centrifugation. Cells can be introduced to the chamber without disturbing the particles and briefly centrifuged to sediment them onto the particles. Photon detection can occur without, during, or, more typically, after the spin.

Filter Device/Magnetic Bead

A modified syringeless filter device, consisting of a chamber and a plunger with a suitable filter (Whatman™, Mini-Uniprep™, or similar), can be loaded with cells which are allowed to attach to the bottom surface of the chamber; unattached cells can be washed away. A sample can be introduced to the chamber along with magnetic beads with a suitable surface affinity. A modified plunger with a suitable magnet inserted inside and fixed near the back-side of the filter can be inserted into the chamber until the entrapped air escapes through the filter. This assembly can be inverted and (possible after a time to allow the beads to sediment onto the filter's surface) the chamber pushed down onto the plunger. Magnetic beads and particles can accumulate on the filter surface by filtration, sedimentation, and magnetic attraction. Particles can attach to the magnetic beads or be caught among them. Upon re-inverting the assembly, the particles, are held off the cells by the magnetic beads which, in turn, are held by the magnet inside the plunger. Removing that magnet releases the beads, and the particles, which sediment across the short distance onto the cells.

Flow Past Cells

One or more layers of cells can be allowed to sediment onto the surface of a suitable filter or membrane at the bottom of a chamber. A sample can be introduced to the chamber above the cells and pressure applied (by plunger or external pump, for example). As the sample flows past the cells, which are in intimate contact, particles are brought within close range of the cells, allowing contact.

Counter Flow

One or more layers of cells can be allowed to sediment onto the surface of a suitable filter or membrane at the bottom of a 'cell' chamber. A sample can be placed in a separate 'sample' chamber which is connected by some flow channel to the cell chamber at a point below the filter. The chambers can be arranged relative to one another such that, in a centrifuge, the sample chamber is closer to the axis of rotation; the level of the fluid in the sample chamber being closer to the axis of rotation than the fluid in the cell chamber. By this means, during the rotation of the centrifuge, fluid will flow between the chambers seeking a common distance from the axis of rotation. This can force some of the sample up through the filter supporting the cells and past the cells which are being held against that flow by the outward centrifugal force. As the sample flows past the cells, which are in intimate contact, particles are brought within close range of the cells, allowing contact.

Centrifuge Tube Filter

A sample can be introduced to the filter basket of a centrifuge tube filter with a suitable size cutoff. Under appropriate centrifuge conditions, the sample will be forced through the filter, accumulating particles larger than the filter's cutoff size on the surface of the filter. Cells can be added to the filter basket and be given a brief centrifugation to bring them onto the filter surface and the particles.

Dielectrophoretic Trap

Similar to the Flow Cell, but with suitable electrodes on any of the surfaces or projecting into the flow cell. A sample can be introduced by continuous flow past the electrodes, which can be connected to and electrically driven by and external source. For a suitable combination of flow rate, frequency, waveform, and amplitude, particles can be guided to and captured in a region of minimum electric field intensity above the cells by negative dielectrophoresis. After stopping the flow and changing the electrical drive to the electrodes (possibly including a DC voltage on between some electrodes to create an electrophoretic force), the particle can sediment or be driven (by electrophoresis or positive dielectrophoresis) onto the attached cells.

Traveling-Wave Dielectrophoresis

In a shallow cylindrical chamber, suitable electrodes (perhaps transparent) can be fabricated on one or both of the parallel faces, including a central planar electrode to collect particles, an electrode around the periphery, and a set of spiral electrodes (either on the same surface as the central one or the opposite surface). A sample can be introduced to the chamber, and a DC potential applied between the peripheral and central electrodes to attract the particles to the central electrode by electrophoresis. By an exchange of fluids, cells can be introduced to the chamber. Energizing the spiral electrodes with the appropriate phase-shifted AC voltages can sweep the cells to the center by traveling-wave dielectrophoresis, where they can sediment onto the particles.

Dissolvable-Membrane Tube

Figure 20:
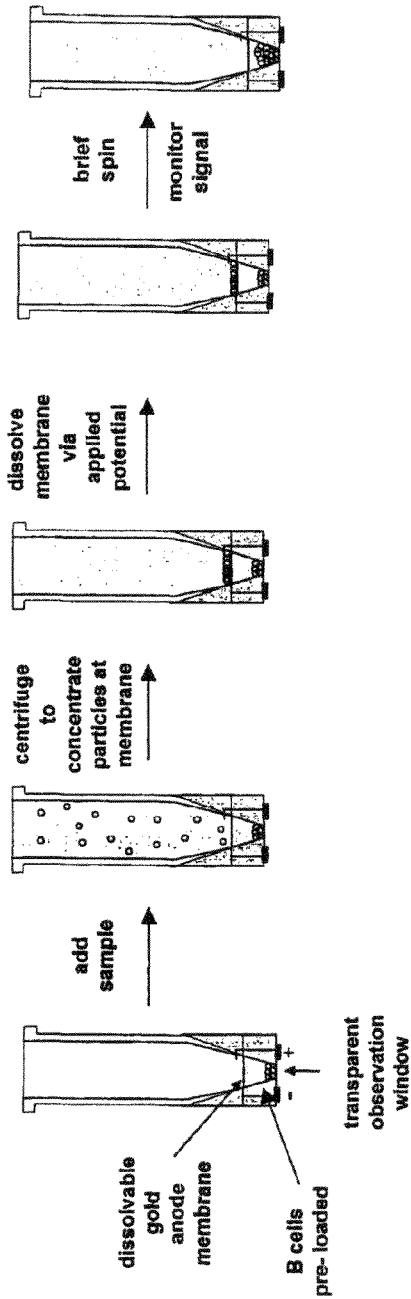
FIG. 20 is a schematic of a custom tube for the optoelectronic sensor.

Use can be made of a electrically-actuated dissolvable gold membrane to maintain isolation between target particles and emitter cells during the localization of the particles by centrifugal sedimentation. Either the particles can be sedimented onto a membrane over the cells (as shown in FIG. 20), or the cells can be held off from the bottom of the chamber by a membrane spanning the bottom of a separate chamber (perhaps an insert). In either case, after the membrane has be dissolved by electrical activation, the particles and cells are mixed by sedimentation, possibly centrifugal.

Acoustics/Ultrasonics

Concentration of particles may be accomplished using acoustic or ultrasonic signals. Particles can accumulate at nodes in a sanding wave pattern, or be move by a traveling-wave pattern. Cells can also be moved this way, or delivered by any of several means discussed above.

Toxin Detection

In order to detect monovalent antigens, it is necessary to induce crosslinking of surface antibodies using one of two general strategies. First, one can express two independent binding sites on the cell surface, such that two receptor molecules can bind to a single ligand. Alternatively, one binding site can be expressed on the cell surface if the ligand is presented to the cell in a manner in which it appears to be polyvalent. The following are specific examples using the model of antibody-antigen recognition.

First, two antibodies can be expressed on the surface of a single cell line, each specific for different epitopes of a individual molecule (epitopes 1 and 2). The binding of a single molecule to two antibodies (one antibody against epitope 1 and another antibody against epitope 2) would initiate crosslinking and light emission. More specifically, a single B cell line is engineered to express two independent antibodies, each recognizing a different epitope on a single molecule. The presence of monomeric antigen is now capable of crosslinking the surface antibodies, resulting in increased intracellular $Ca^{2+}$ and emission of light by aequorin. A cell line that expresses functional antibodies against both *Y. pestis* and *F. tularensis* (in addition to the endogenously expressed PC antibody) has been tested (see Examples). Each of these agents is recognized independently by this cell line, indicating that both antibodies are functional and demonstrating that emittor cells are capable of expressing two functional antibodies simultaneously.

Another potential issue is the sensitivity of the optoelectronic device and methods with an antigen that cannot be pelleted using centrifugal force. The *Yersinia pestis* F1 antigen exists as a low molecular weight polymer in solution, and is therefore not sedimentable in our assay. However, B cells expressing antibody against F1 are capable of detecting soluble F1 antigen at 5 ng/ml. This compares favorably with current immunoassay techniques and demonstrates that the optoelectronic device can be quite sensitive to soluble agents. A complementary experiment was carried out using phosphorylcholine antigen conjugated to ovalbumin. The ability of this small antigen to stimulate antibody crosslinking on the cell surface indicates that this low molecular weight antigen, containing multiple copies of PC epitopes, is able to effectively crosslink surface antibodies and generate calcium influx and photon emission.

A second strategy can improve the limit of detection for monovalent antigens shown above by taking advantage of the centrifugal format. This approach utilizes a scheme where one of the toxin antibodies is expressed on the surface of benign bacteria and the second antibody on the surface of B cells. The toxin can now be sedimented by centrifugation, and B cells expressing the second antibody added. Because multiple antigens are immobilized on the surface of the bacteria, the toxin will in essence appear polyvalent to the B cell, and will initiate a crosslinking event and photon emission. More specifically, Antibody against epitope 1 of a monomeric antigen (e.g. toxin) is expressed on the surface of bacteria. Soluble toxin binds to these antibodies, coating the bacteria with toxin antigen. These toxin-coated bacteria are sedimented by centrifugation prior to addition of B cells expressing antibody against epitope 2. Crosslinking of the B cell antibodies results in light emission by aequorin. Experimental results on this strategy demonstrate the feasibility of detection of bacterial surface antigens, and the increased sensitivity resulting from sedimenting those bacteria prior to the addition of B cells. Similar approaches can also be used for any poorly sedimenting agent to improve its presentation to B cells.

Crosslinking

Crosslinking of target particles can be achieved by any known means. For example, crosslinking can be achieved using one or more intermediate agents or molecules such as a peptide, an antibody, a chemical compound, an antibody, biotin, streptavidin, in addition, crosslinking can be via covalent or non-covalent bonding. Methods for crosslinking also include precipitation or attachment to a solid phase via ligands, antibodies or chemical functional groups, as are known in the art.

Multiplexing Assays

The following is a description of how B cell mixtures can be used to increase the number of detectable antigens without increasing the number of detection channels (tubes, etc). The simplest way to detect multiple analytes is to use a single emittor cell type per detection channel and to increase the number of cell assays by increasing the number of detection channels. This is acceptable for small numbers of assays but, as increasing numbers of analytes are added, the process becomes more complex and resource intensive. It is possible, however, to conduct up to 31 tests with concurrent negative controls in only a 5-channel system if different B cell lines are mixed together.

As an example, if one has a single channel, one can at most detect a single B cell assay. If, however, one has two channels, then one can detect 3 separate assays, where each channel contains an equal mixture of 2 of the 3 separate B cell lines:

For example, if one has 3 B cell lines: A,B,C

And one mixes them into two channels thusly—

2 Channel 1: A, B Channel 2: B, C

Then there are three positive readout possibilities:

| Channel 1 | Channel 2 | |
|---|---|---|
| Yes | No | implies only A is present |
| No | Yes | implies only C is present |
| Yes | Yes | implies only B is present (or that more than one agent is present, which we will consider unlikely for now) |

Similarly, if one has 3 channels, one can detect 7 independent assays, by mixing groups of four cell lines together—

(A convenient shorthand will hereafter be utilized where the cell lines for individual agents are labeled A through a letter corresponding to the number of cell lines, and the channel numbers will be written to indicate what channels are required to detect positively for each individual agent as follows—123: F—means channels 1, 2, and 3 must all register positive to ID agent F).

| Channel 1 | Channel 2 | Channel 3 |
|---|---|---|
| A, B, G, F | B, C, E, F | C, D, G, F |
| 1: A | 12: B | 123: F |
| 2: E | 13: G | |
| 3: D | 23: C | |

A formula embodying the relationship that simply describes the number of independent assays that can be accessed by a given number of channels, assuming all assays are mixed in equal proportion is:

Cell assays=$2^n-1$ where n is the number of channels and the number of cell assays that need to be mixed in each channel is given by $2^{(n-1)}$.

Thus, to mix 16 different B cell lines together, 5 channels are needed to interrogate 31 different assays. The design for a 10-channel system could, in fact, be used to provide ID for 31 separate agents with concurrent negative controls (5-channel positive ID, 5-channel negative control).

The channel mixtures and positive detection correlation for a 4-channel system (15 different assays) is shown below:

| Channel 1 | Channel 2 | Channel 3 | Channel 4 |
|---|---|---|---|
| A, B, G, F, | B, C, H, I | F, C, D, I | D, E, G, H |
| I, K, L, M | J, L, M, N | J, K, M, O | J, K, L, M |
| 1: A | 23: C | 123: I | 1234: M |
| 2: N | 24: H | 234: J | |
| 3: O | 34: D | 134: K | |
| 4: E | 12: B | 124: L | |
| | 13: F | | |
| | 14: G | | |

Without further elaboration, it is believed that one skilled in the art can, based on the above disclosure and the examples below, utilize the present invention to its fullest extent. The following examples are to be construed as merely illustrative of how one skilled in the art can practice the invention, and are not limitative of the remainder of the disclosure in any way.

EXAMPLES

Figure 1:
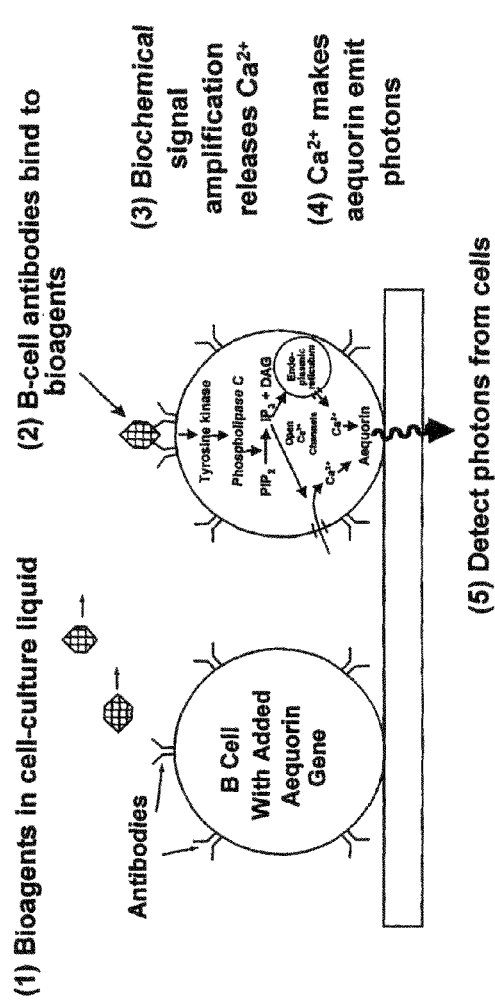
FIG. 1 is a schematic of the optoelectronic sensor cellular concept.

FIG. 1 is a schematic diagram showing the general cellular components of the invention. A cell (here a B cell) that contains an emitter molecule (here aequorin) has antibodies present on its surface. These antibodies are specific for an antigen on a target particle, such as a biological warfare agent. Binding of the target particle to antibodies on the B cell brings two or more antibodies close together on the cell surface, causing a signal transduction cascade that leads to release of calcium from intracellular stores into the cytoplasm. This increase in cytoplasmic calcium concentration causes aequorin to emit a photon. The photon is then captured and registered by a photo multiplier device, such as a CCD. Thus, a cellular biosensor can be implemented using cells having functional surface antibodies and containing a cytoplasmic emitter molecule that responds to increased calcium concentration.

Such a cell-based detection system provides rapid, sensitive, specific, accurate, and flexible detection of any antigen on any target particle. In regard to flexibility, the system can be modified to target any particle or groups of particles. In one example, a single emitter cell can contain a plurality of antibody types, each type being specific for non-overlapping groups of target particles. This single emitter cell can then be used to identify a genus of target particle species at once.

In a second example, a reaction chamber can contain two types of emitter cells. One type of emitter cell contains antibodies that are specific for a genus of target particles (e.g., bacteria) and emits a photon of a first wavelength in response to contact with any member of the genus. The second type of emitter cell contains antibodies that are specific for a particular species within the genus (e.g., *Yersinia pestis*) and emits a photon of a second wavelength different from the first wavelength in response to contact with the species. This arrangement offers extremely high accuracy by reducing or eliminating false positive signals. Only when photons of the first and second wavelength are detected, would a positive event be registered. This nesting of emitter cell specificities can be extended to more than two levels as necessary to reduce or eliminate false positive signals.

Figure 2:
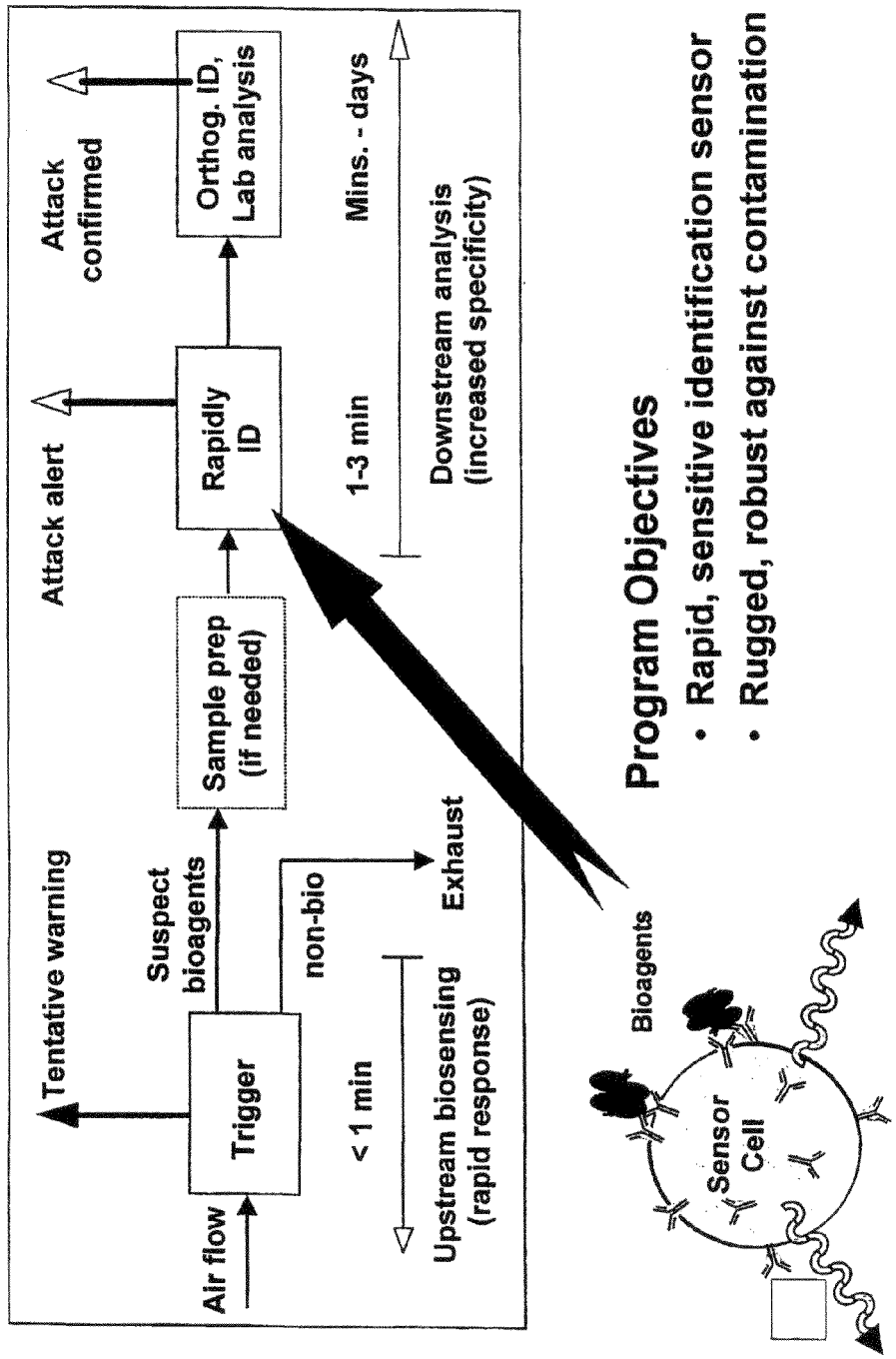
FIG. 2 is a schematic showing the general architecture of an optoelectronic sensor having a sampler (trigger) for preliminary sensing of suspect agents.

FIG. 2 is a schematic diagram of a general architecture and use environment for the invention.

Figure 3:
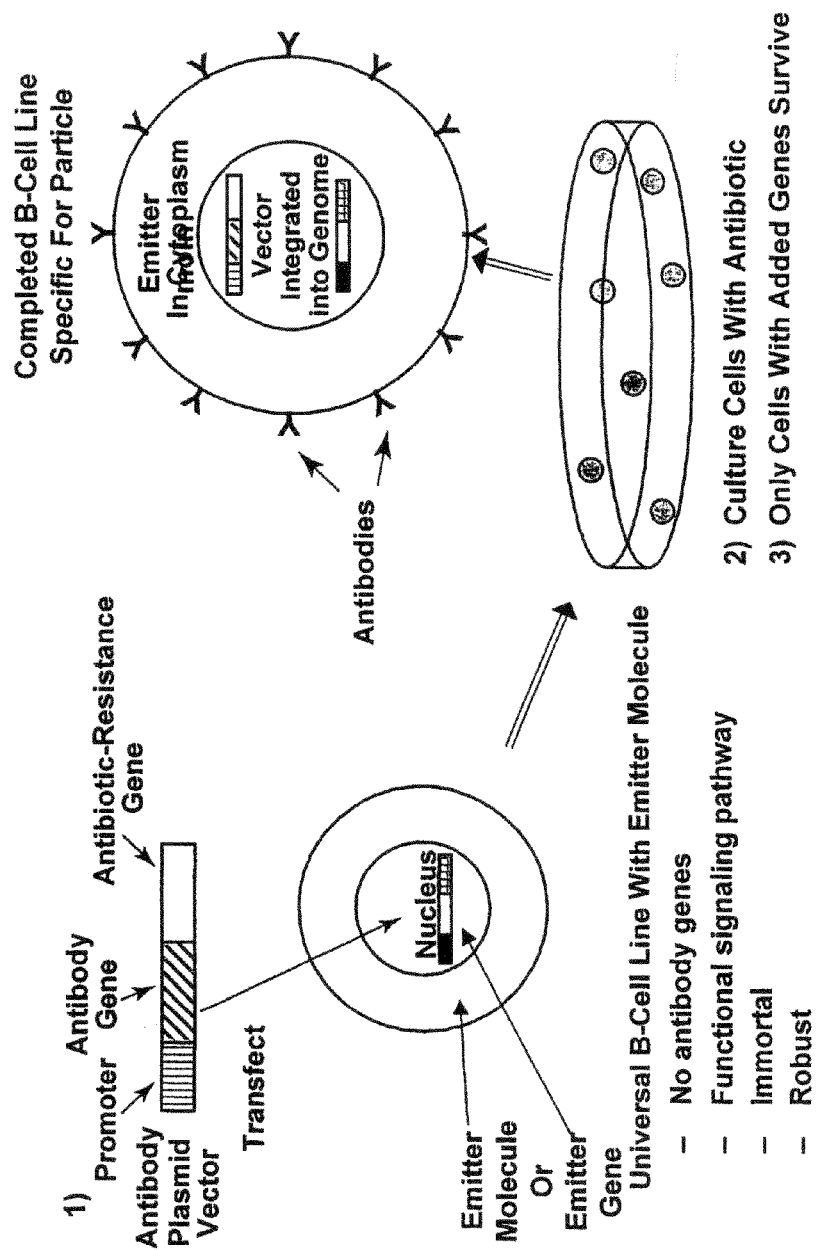
FIG. 3 is a schematic illustrating the creation of cell lines for use in the optoelectronic sensor.

FIG. 3 is a schematic diagram of the molecular biology employed in one embodiment of the invention. In this example, a universal B cell line that expresses an emitter molecule (e.g., aequorin) but does not express antibodies becomes the basis for generating B cells that can express any antibody specific for any antigen. An antibody expression vector is introduced into the universal B cell, selected for the presence of the expression vector, and expanded for use in a detection system of the invention. Using this strategy, in conjunction with pDisplay and VKExpress (described in "Antibodies" section above), target-specific emitter cells were generated for a variety of targets. Emitter cells specific for Foot and Mouth Disease virus (FMDV), Venezuelan Equine Encephalitis (VEE) virus, *Yersinia pestis, Francisella tularensis, Brucella* spp., the O1 and O139 strains of *Vibrio cholera*, and *orthopox* viruses have been produced. The cDNA and sequence for the FMDV antibody variable regions were obtained from the USDA. The cDNAs and sequences for the *Yersinia pestis, Francisella tularensis, Brucella* spp., the 01 and 0139 strains of *Vibrio cholera* antibody variable regions were obtained from investigators at NMRC. The variable regions of the VEE and *orthopox* antibodies were cloned from hybridomas obtained from the CDC and USAMRIID, respectively. Foot and Mouth Disease Virus (FMDV), *Yersinia pestis, Francisella tularensis*, and Venezuelan Equine Encephalitis Virus (VEEV) are responsible for Foot and Mouth Disease, the Plague, tularemia, and encephalitis, respectively. Cloning from the hybridomas was done with a combination of primers described in several published articles. Emitter cells specific for *Bacillus globigii* are being produced because this non-pathogenic bacterium is used by some military agencies as a test organism in field trials of biological warfare agent detection systems. FIG. 5 includes a line graph showing the photon emission response when several clones of FMDV-specific emitter cells were contacted with live FMDV targets. In each case, the emitter cells fired photons within about 20-30 seconds after contact between the target and the cells. Included in the graph is data showing a lack of emission when a mutant FMDV (having single amino acid mutation in the viral coat protein) that would not be expected to bind to the emitter cell was contacted with an emitter cell clone. The negative control supports the high specificity that is built into the detection system.

Various configurations of a centrifuge and photomultiplier tube (PMT) arrangement can be incorporated into a system of the invention. The arrangement includes a rotor (motor) that spins a sample microfuge tube from a swinging harness and includes a balance tube in a fixed position. The PMT is shown at the bottom, facing upwards toward the bottom end of sample tube at rest. In a typical experiment for a target particle that is smaller than the emitter cell, the particle-containing liquid sample is placed in the sample tube and centrifuged under conditions sufficient to sediment the majority of the particles to the bottom of the tube (e.g., 60 seconds at 5600×g for *Francisella tularensis*). A suspension of emitter cells is then layered onto the sample in the tube (so as not to disturb the sedimented particles) and spun briefly to pellet the cells into contact with the target particles. If target particles are present in the candidate particles, photons of a specific wavelength should be emitted from the cells and captured and registered by the PMT.

In specific embodiments, the PMT can be a Hamamatsu HC 125-08 PMT interfaced with a Stanford Research systems SR400 Two Channel Gated Photon Counter. The centrifuge can be a Sapphire 17 turn, 18.5 AWG, 5 amp motor having a swinging bucket configuration.

The centrifuge tube (reaction chamber) can be altered and upgraded as needed to aid contact between candidate particles and the emitter cells. In one embodiment shown in FIG.

20, the tube contains an enclosed compartment that holds pre-loaded emitter cells at the bottom of the tube. This compartment is separated from the rest of the tube by a dissolvable gold anode membrane. In operation, a same containing candidate particles is deposited into the tube and spun to concentrate candidate particles at the membrane. The membrane is then dissolved, and the tube briefly spun to contact the particles with the emitter cells. This dissolvable membrane system is described by Langer and colleagues in Angewantde Chimie International Edition 39:2396-2407, 2000; and Nature 397:335-338, 1999.

The steps in the centrifuge process can be automated or alternatively designed so that the user need not stop the centrifuge at all. For example, the introduction and removal of liquids and samples can be accomplished without the need to stop the rotor by adapting the mechanical features of preparative centrifuges (e.g., ultracentrifuges) available from Beckman Instruments. In addition, it may be desirable to detect photon emission while centripetal forces are still being applied (e.g., when the contact between emitter cells and target particles are unstable without centrifugation). To detect photons emitted from the sample tube while it is spinning, the PMT can be arranged in a radial position relative to the rotor axis. In most cases, the PMT in this arrangement need not be spinning along with the sample tube, but instead can be stationary and simply register emission of photons when the sample tube passes in front of the PMT. If the emission signal is very weak, then the detector (e.g., PMT, a CCD chip) can be coupled to the rotor and spun along with the sample tube. Alternatively, multiple PMrs can be arrayed around a circumference of a rotor for detecting emissions.

If multiple samples are spun on the same rotor, the positioning or signal processing of the PMT can be altered if necessary. In one embodiment, the rotor accommodates 4 sample tubes, each containing cells that emit at the same wavelength. To differentiate emissions originating from one sample over the emissions from another, a single radially aligned PMT can detect emissions continuously. The continuous emission data is then resolved using a timing trace from the rotor, which monitors the position of each sample over time, to allocate the emissions to each sample. Other variations are understood to be within the invention.

Figure 17:
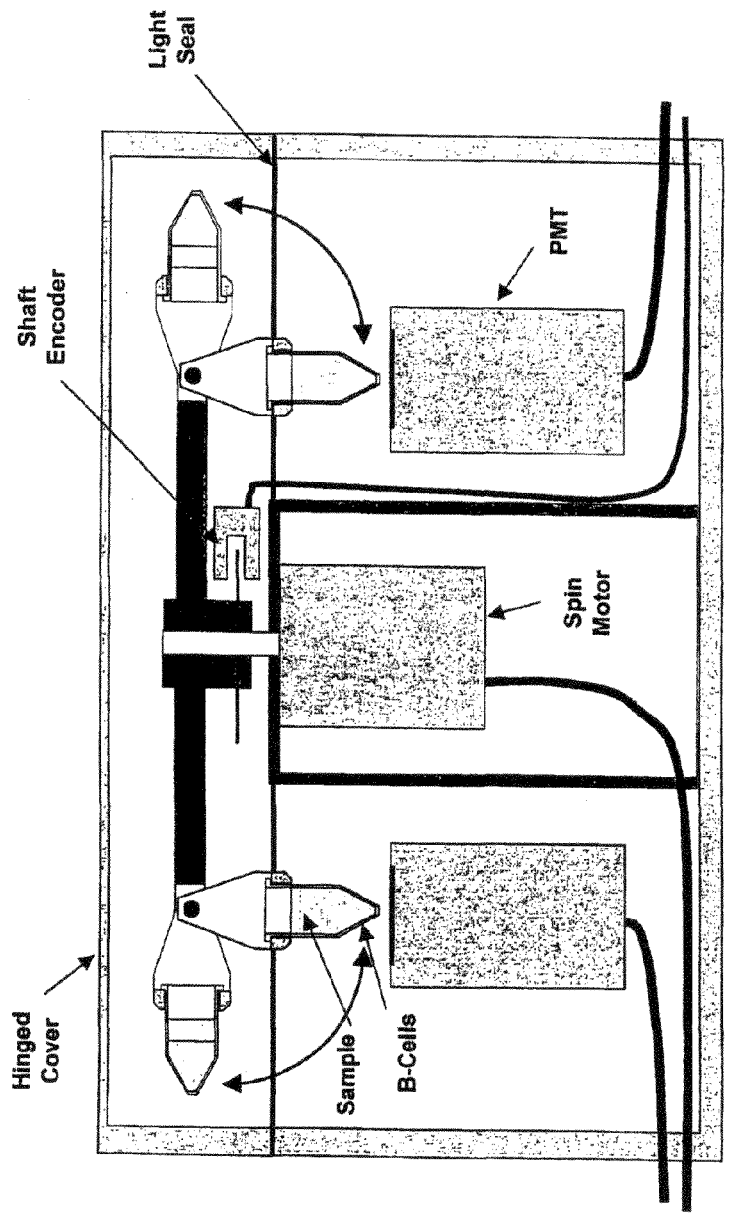
FIG. 17 is a schematic illustrating a multi-channel centrifuge in the optoelectronic sensor.
Figure 18:
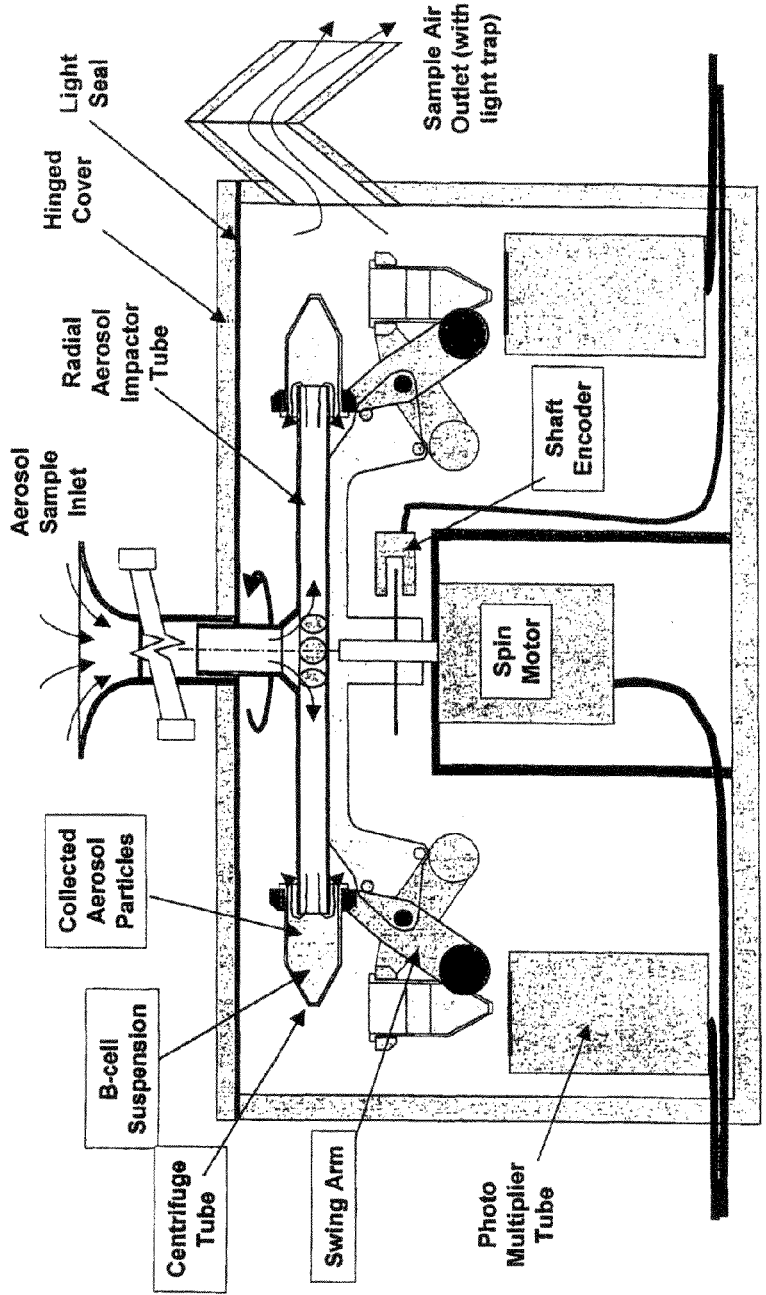
FIG. 18 is a schematic illustrating a wet centrifuge/impactor concept in the optoelectronic sensor.
Figure 19:
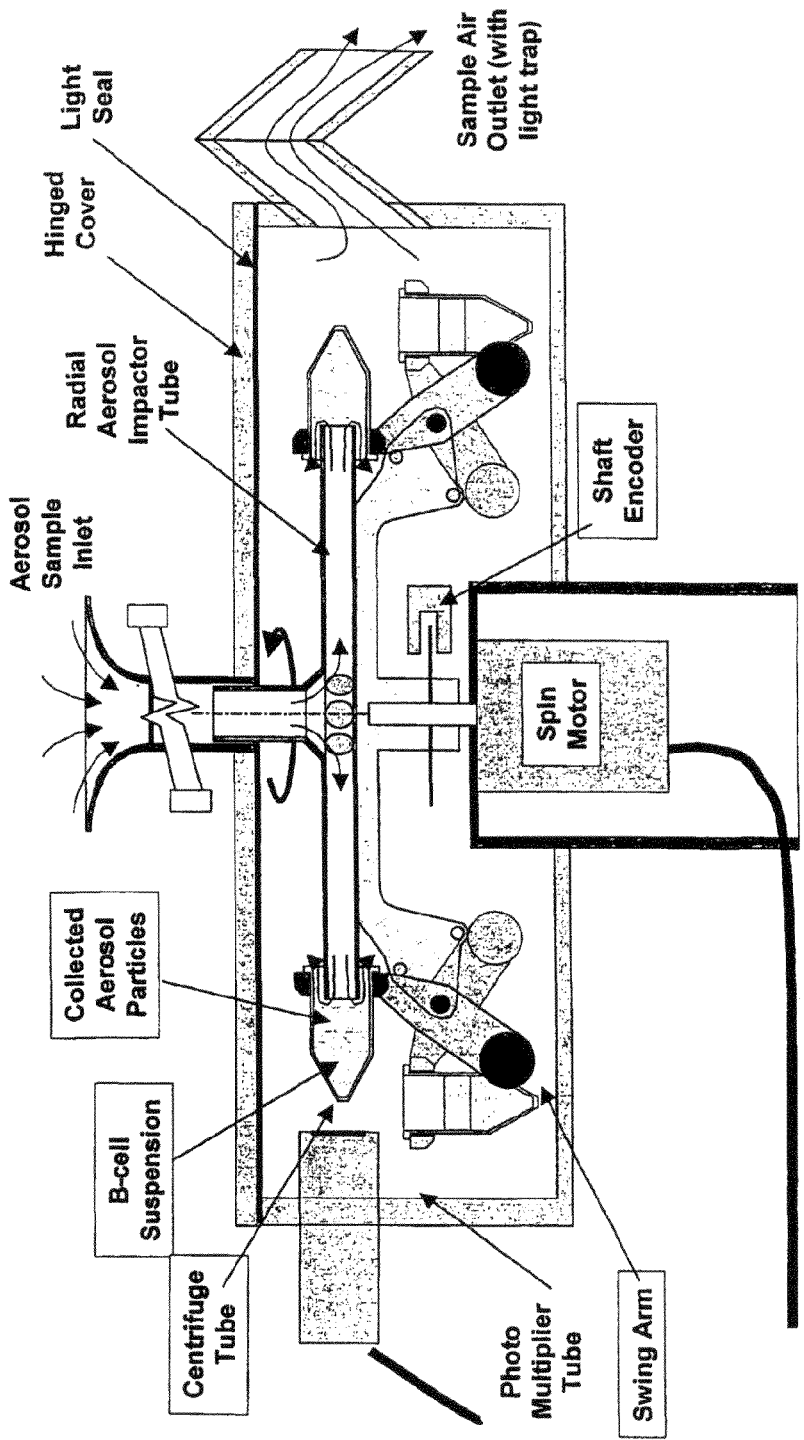
FIG. 19 is a schematic illustrating a wet centrifuge/impactor concept in the optoelectronic sensor.

For example, FIG. 17 is a schematic drawing of two reaction tubes coupled to a rotor, with two PMTs aligned below the tubes. At a resting position, the rotor positions each of the tubes below the corresponding PMT, using the rotor position encoder. In another example, the centrifuge system shown in FIG. 17 can be integrated with an air sample collector to achieve the system shown in FIG. 18. The radial aerosol impactor tube can include any type of particle monitor, such as described in U.S. Pat. No. 5,932,795 and references cited therein. In still another example, the system described in FIG. 18 can be altered so that only one PMT aligned radially in relation to the rotor axis is required, as shown in FIG. 19. As discussed above, emissions registered by the PMT are resolved for each sample tube using the shaft encoder.

Referring back to FIG. 17, fluid components including, but not limited to, suspensions of B cells engineered to recognize specific bioagents, buffer solutions, preservatives, cell culture medium, can be placed in each of several centrifuge tubes, mixed with a liquid suspension of the sample particles that has previously been collected from aerosol samples in a separate process particles may include but are not limited to, proteins, peptides, chemicals, viruses, bacteria in vegetative and spore forms, fungal spores, pollen grains, protozoa, blood or tissue derived cells, and fragments thereof either alone or in conjunction with carrier particles such as dust). When the spin motor is started, the centrifuge tubes swing out into a radial position, and the B cells and/or sample particles are driven to the bottom of the centrifuge tubes at rates depending upon the size and density of the particles. The exact sequence whereby cell and sample-containing fluids are added and centrifuged can be customized based on their relative sedimentation velocities to maximize signal. In general, it is expected that maximum photon output can be obtained from particles that sediment more slowly than B cells by spinning these samples (a pre-spin) for appropriate times before the addition of B cells and spinning to bring them into contact. For particles sedimenting at similar or faster rates than B cells, a single spin of the mixed sample and B cell components will initiate maximal photon output from the system. Data from particle size analyzers (including but not limited to BAWS units, and fluid particle analyzers) incorporated upstream of the centrifugation device can be used to automatically determine the optimal operation sequence and initiate appropriate computer-controlled automated sample handling.

When the "spin cycle" is terminated and the rotor comes to a controlled stop in a pre-determined position controlled by the spin motor and shaft encoder, the swing arms rotate under gravity forces so that the bottoms of the centrifuge tubes are presented to the sensitive surface of the photomultiplier tubes, and any light signals are then recorded. In a modified version of this implementation, a single photomultiplier tube can be positioned at the maximum radius of the rotor/tube configuration and used to collect photons from each tube as they pass by the sensitive surface of the photomultiplier tube in succession. The photon output measured from individual tubes can be assigned and combined based on the monitoring of the shaft encoding system.

Referring back to FIG. 18, the process of collection of the aerosol particles is integrated with the process of bringing the aerosol particles into contact with the B cells. Here, the centrifuge tubes are attached to swing arms that allow them to cover the ends of radial impactor tubes while spinning, and the aerosol sample is induced to flow into the sample inlet by the centrifugal forces acting on the air in the rotating radial impactor tubes (can be assisted as necessary by additional blower units). The high velocity of the flow causes aerosol particles to impact on the inner surface of the centrifuge tube or the surface of a liquid contained in the tubes and results in the capture of the particles on the surface of the tube or in the liquid, respectively. When a liquid is present, centrifugal pressures acting on the liquid will balance the force imparted by the high velocity air flow required for particle capture in the liquid and prevent it from being blown out by the impacting air. The aerosol particles are retained following impact with the tube surface or liquid and in the case of liquid collection, forced to flow radially outward thereby providing increased local particle concentrations at the maximum radius (the bottom of the centrifuge tube). Addition of B cells and spinning them into the locally concentrated particle zone following the collection phase will initiate photon output. Alternatively, the B cells can be present in the fluid during collection and light output monitored in real time while spinning with a single photomultiplier tube (FIG. 19). In a modified version of this implementation, the fluid components (including but not limited to particle samples collected via an alternative bioaerosol collector, and suspensions of engineered B cells) could be added to the inlet(s), and the centrifugal forces can be used to distribute them to the tubes.

When the "spin cycle" is terminated and the rotor comes to a controlled stop in a pre-determined position controlled by the spin motor and shaft encoder, the swing arms rotate under gravity forces so that the bottoms of the centrifuge tubes are presented to the sensitive surface of the photo-multiplier tubes, and any light signals are then recorded. In a modified version of this implementation, a single photomultiplier tube can be positioned at the maximum radius of the rotor/tube configuration and used to collect photons from each tube as they pass by the sensitive surface of the photomultiplier tube in succession. The photon output measured from individual tubes can be assigned and combined based on the monitoring of the shaft encoding system.

Figure 7:
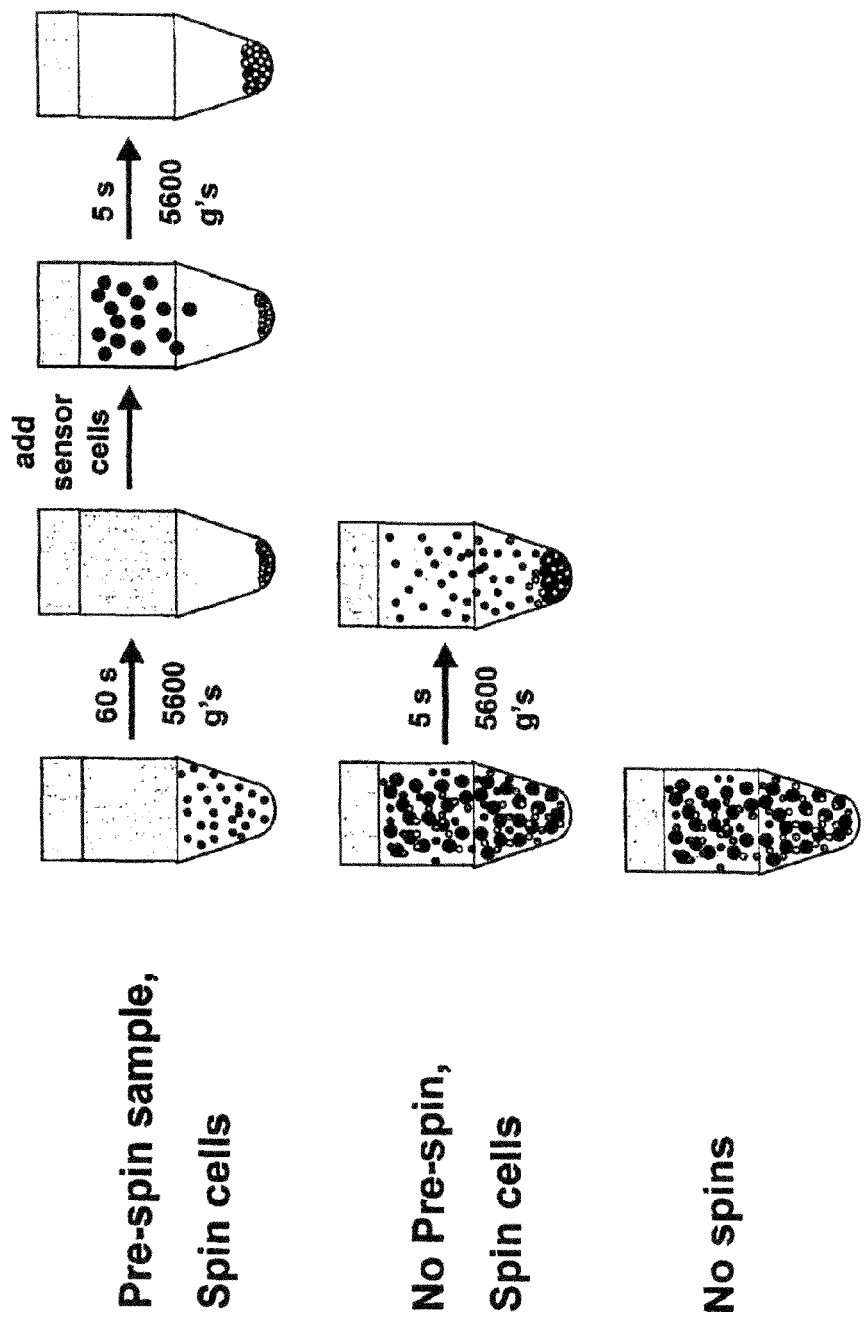
FIG. 7 is a schematic illustrating the effect of localization and mixing.

FIG. 7 is a schematic representation of the results of sequential centrifugations. For target particles smaller than emitter cells but having the same density of emitter cells, it is beneficial to first spin the candidate particles (e.g., at high speed) to pellet them. Thereafter the emitter cells can be added and spun under conditions which can be milder to prevent reduction of their responsiveness as needed (top series). In addition, this sequence of centrifugation forces almost all candidate particles and emitter cells into a relatively small volume at the bottom of a centrifuge tube. In contrast, mixing the candidate particles and the emitter cells together and spinning them at one time will lead to separation rather than contact between the particles and emitter cells (middle series). Of course, no spin at all dramatically reduces the effective concentration of particles and emitter cells in the reaction (bottom series).

Figure 8:
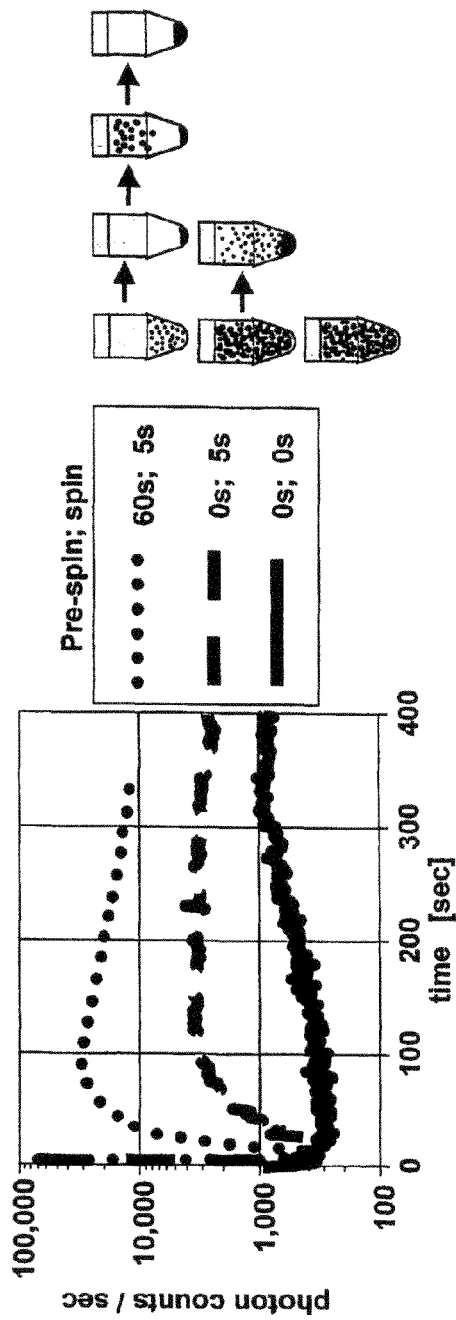
FIG. 8 illustrates the effect of localization using tularemia cells.

FIG. 8 includes a line graph showing in an actual experiment confirming the consequences proposed in FIG. 7. Emitter cells specific for Francisella tularensis were mixed with killed Francisella tularensis cells in the three methods shown in FIG. 7. As seen in the line graph, the sequential spin method resulted in fast and efficient emission after contact. In contrast, the emission profile of the single spin method was far less pronounced in both timing and magnitude. The no-spin method barely exhibited a reaction.

A similar emission profile was generated in a separate experiment, as summarized in the line graph shown in FIG. 8. Inspection of the emission traces suggested that the single spin method resulted in target-specific emissions a little quicker than the two-spin method. However, this result was found to be primarily an artifact of the longer spin required for the two-spin method and does not reflect an actual improvement in the response time of the B cells. In fact, the initial slope of the two-spin method was significantly greater than that for the single spin method, indicating that the two-spin method led to a robust emitter response.

Figure 10:
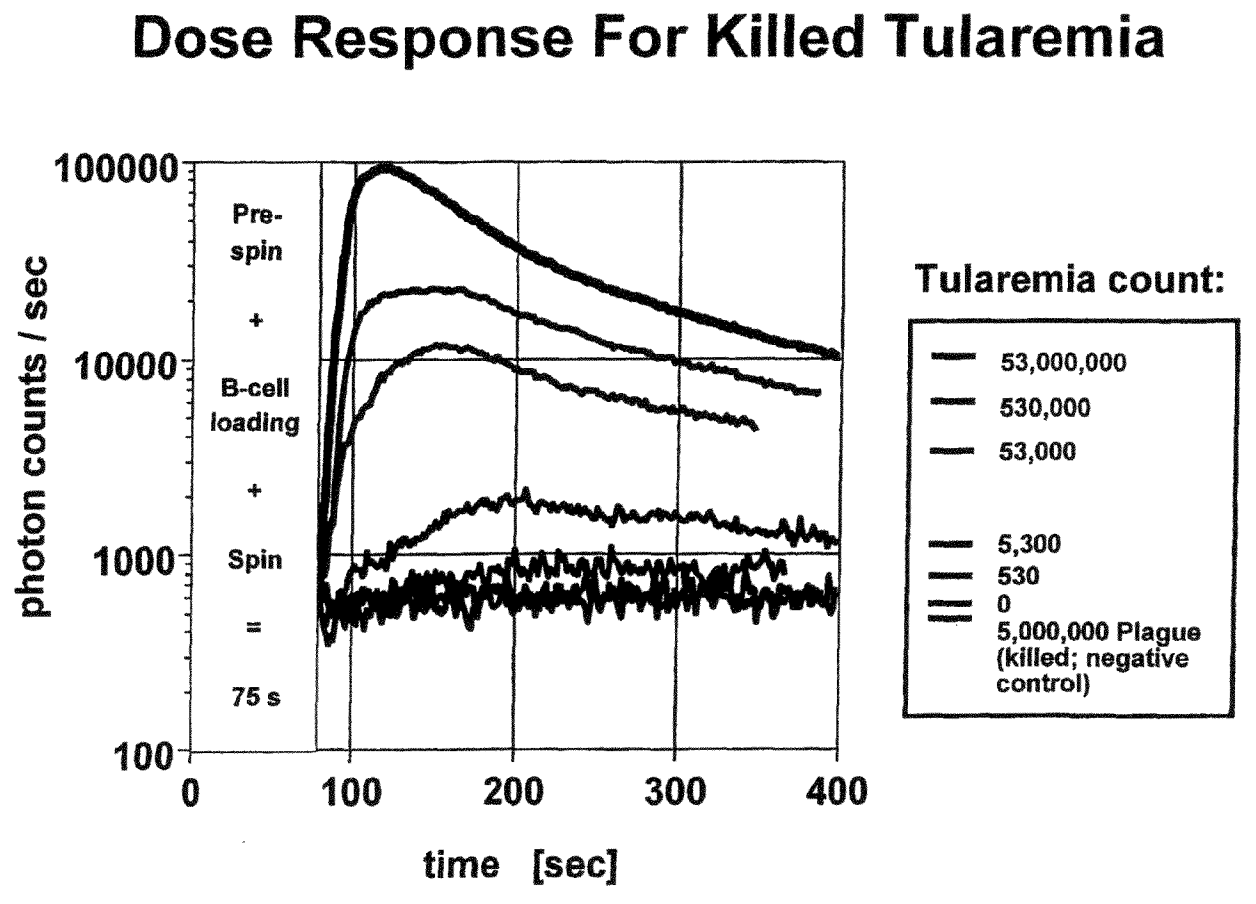

The sensitivity of the detection system shown in FIG. 8 was evaluated by titrating the number of tularemia cells deposited into the centrifuge tube. The results are summarized in the line graph shown in FIG. 10. It appears that 25,000 emitter cells were capable of emitting photons detectable above background in response to about 5,300 tularemia target particles. It is expected that further optimization of reaction conditions will increase sensitivity.

Figure 22:
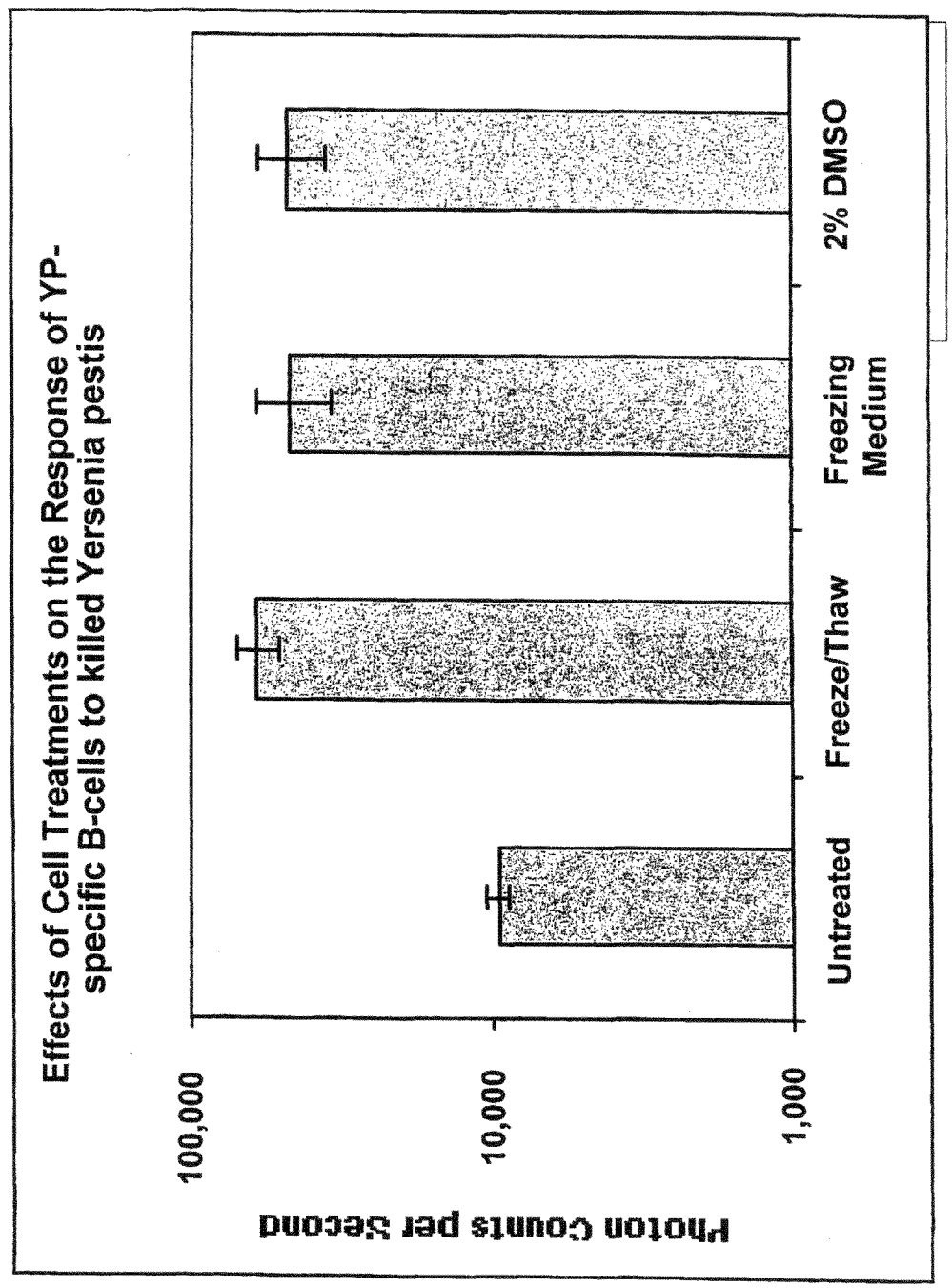
FIG. 22 illustrates the effect of cell treatments on the response of *Yersenia pestis* specific B cells.
Figure 24:
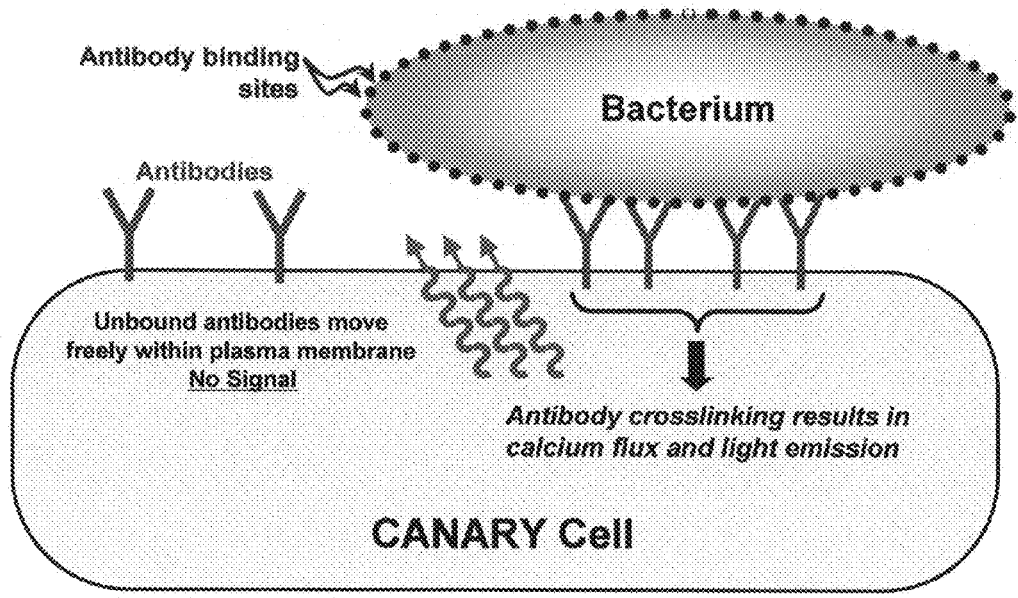
Figure 25:
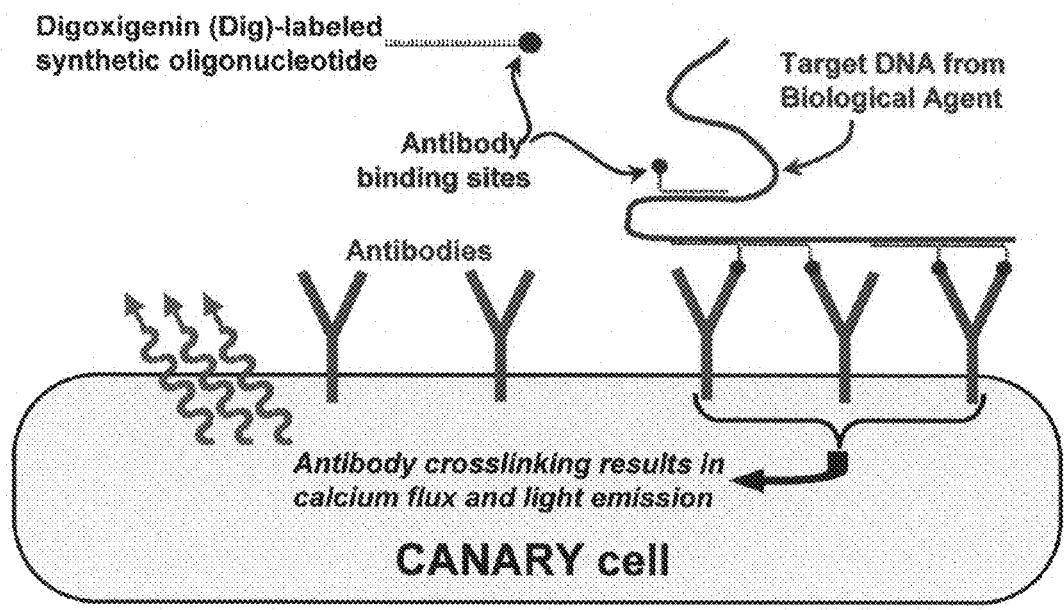

Cell responses are improved after a single freeze-thaw cycle (see FIG. 22). In this experiment, cells specific for Yersenia pestis (YP) were centrifuged, resuspended in freezing medium (RPMI with 10% DMSO and an additional 10% FBS), frozen at −80° C., and transferred to liquid nitrogen. Cells were thawed at 37° C. and 1 ml ($2 \times 10^6$) cells were diluted into to 4 mls of RPMI and incubated overnight at 37° C. The following day the cells were loaded with coelenterazine for 2 hours, washed into $CO_2$—Independent medium ($CO_2$—I) and recovered for 24 hours. 10,000 cells were challenged with $5 \times 10^5$ YP (50 ul of YP at $10^7$/ml). Untreated cells displayed a response of 9500 photons per second, while frozen thawed cells emitted approximately 6 fold more photons in response to YP. This stimulatory effect could be largely replicated by exposing the cells to freezing medium, without the actual freezing (5 fold stimulation). It appears that the stimulatory factor in the freezing medium is the DMSO. When cells were treated with 2% DMSO (the final concentration of DMSO when 1 ml of cells in freezing medium containing 10% DMSO is diluted into 4 mls of normal medium) a similar level of stimulation was detected. The DMSO effect may be due to a number of factors. DMSO is known to effect hematopoetic cell differentiation, and may be stimulating the cells through this pathway. Additionally, cells frozen in medium containing glycerol also show similar levels of stimulation. Thus, it appears that the effect can also in part be due to a stress response induced by the DMSO and it can be possible to replicate this stimulation using any of a number of conditions that stimulate a "heat shock" response.

The cells can be stored frozen in the coelenterazine-charged state. Cells were loaded with coelenterazine, allowed to recover for 24 hours, and then frozen. Upon thawing the cells were washed through 10 ml of $CO_2$—I medium and the cells were resuspended in $CO_2$I medium to a concentration of $5 \times 10^5$ cells/ml. These cells were capable of detecting YP (in this case about 1 hour after thawing, but shorter times are possible). These cells remained capable of detecting agent for several days when stored at RT. Pretreatment of these cells with DMSO, prior to loading with coelenterazine and freezing, can increase the sensitivity of the cells to agent after thawing.

In FIG. 22, cells were challenged with 50 ul of 10,000,000 YP/ml diluted in $CO_2$—I after various cell treatments. Untreated: Cells were grown in RPMI, loaded with coelenterazine, washed, recovered for 24 hours, and challenged with YP. Freeze/Thaw: Cells were grown in RPMI, transferred to freezing medium, and frozen. Thawed cells (1 ml) were placed into 4 mls of RPMI and incubated at 37° C. for 24 hours, loaded with coelenterazine, washed, recovered for 24 hours, and challenged. Freezing Medium: Cells were grown in RPMI, transferred to freezing medium and incubated at RT for 10 minutes. Cells (1 ml) were placed into 4 mls of RPMI and incubated at 37° C. for 24 hours, loaded with coelenterazine, washed, recovered for 24 hours, and challenged. 2% DMSO: Cells were grown in RPMI, transferred to RPMI containing 2% DMSO and incubated at 37° C. for 24 hours, loaded with coelenterazine, washed, recovered for 24 hours, and challenged.

Figure 11:
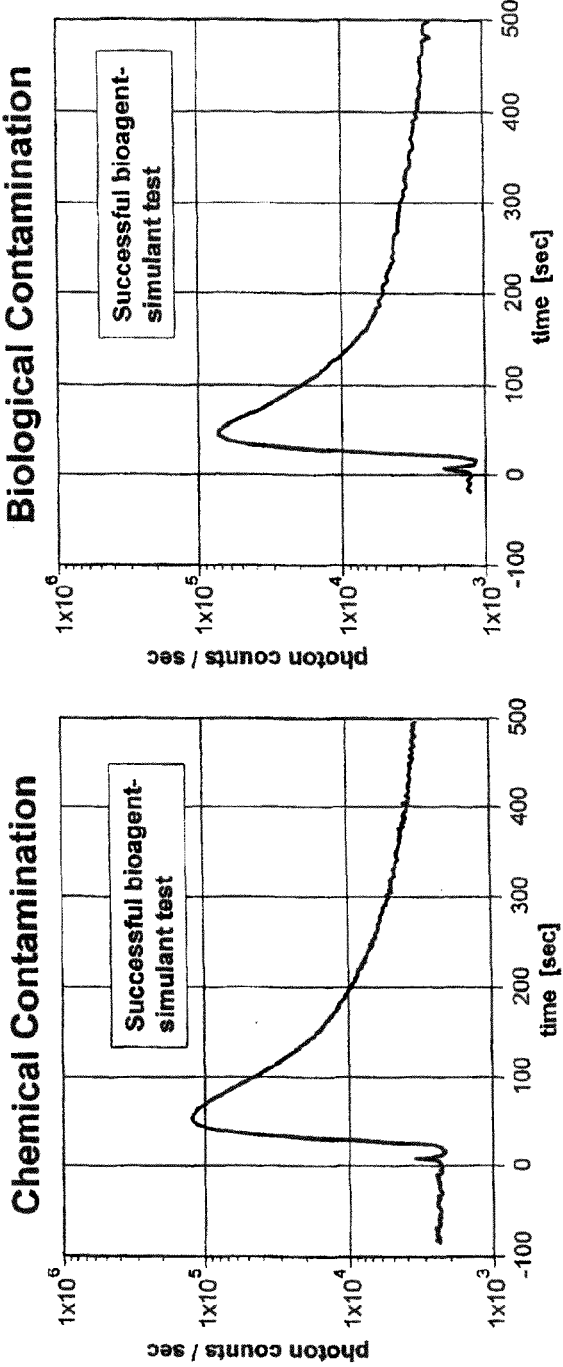
FIG. 11

A successful biological warfare detection system should be resistant to contamination by common environmental substances present on a battlefield. To evaluate whether emitter cells can operate under environmental stress or contamination, emitter cells were mixed with a target particle after exposure of the emitter cells to one hour of full strength diesel exhaust (left line graph in FIG. 11), or when the emitter cells were contaminated by $10^7$ E. coli (right line graph in FIG. 11), which was used as a surrogate contaminant for any field bacterium. As shown in FIG. 11, the particular chemical and biological contaminants tested did not affect the ability of emitter cells to fire photons in response to a target particle.

Figure 13:
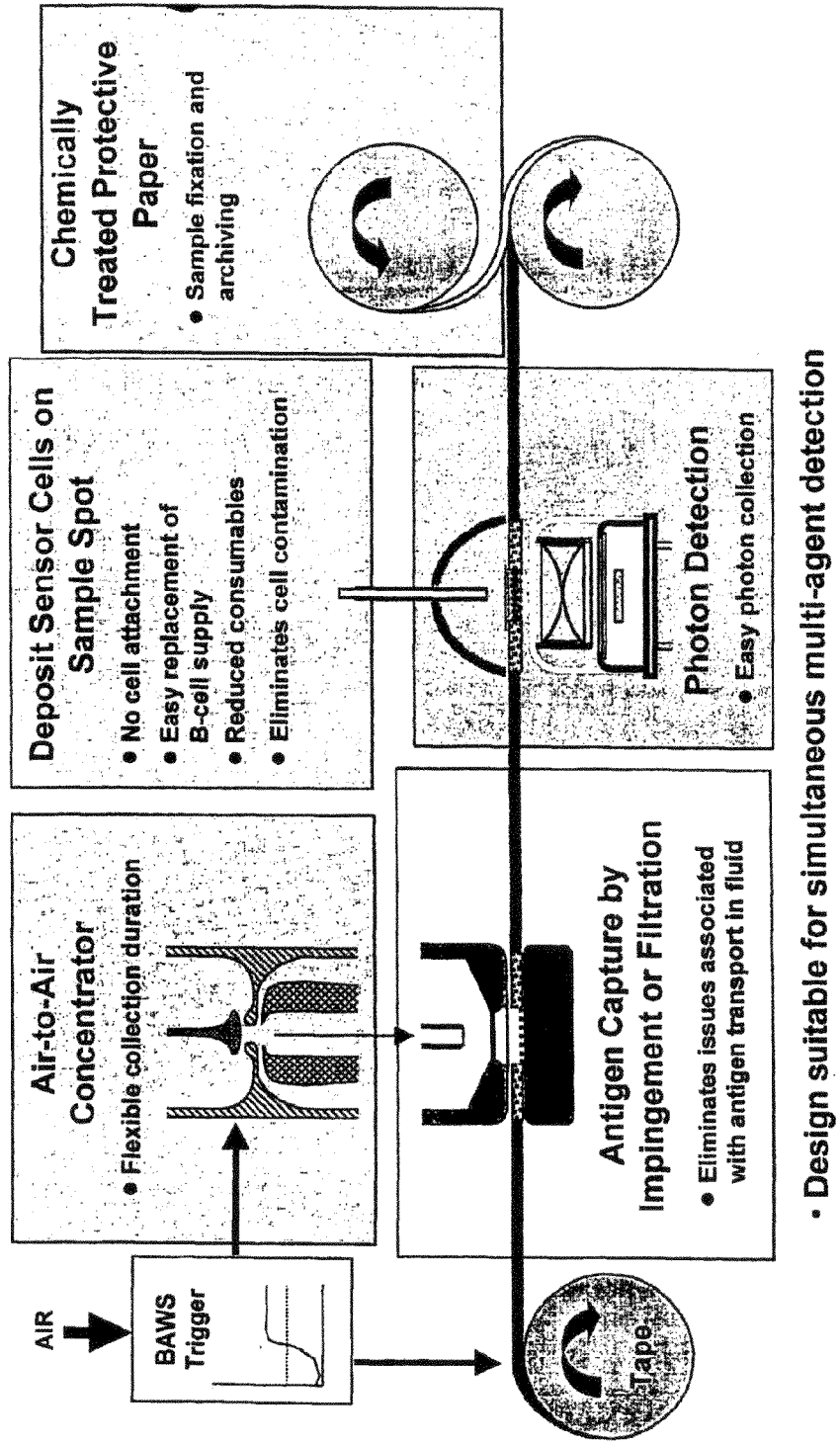
FIG. 13 is a schematic illustrating an air impactor/optoelectronic sensor.
Figure 14:
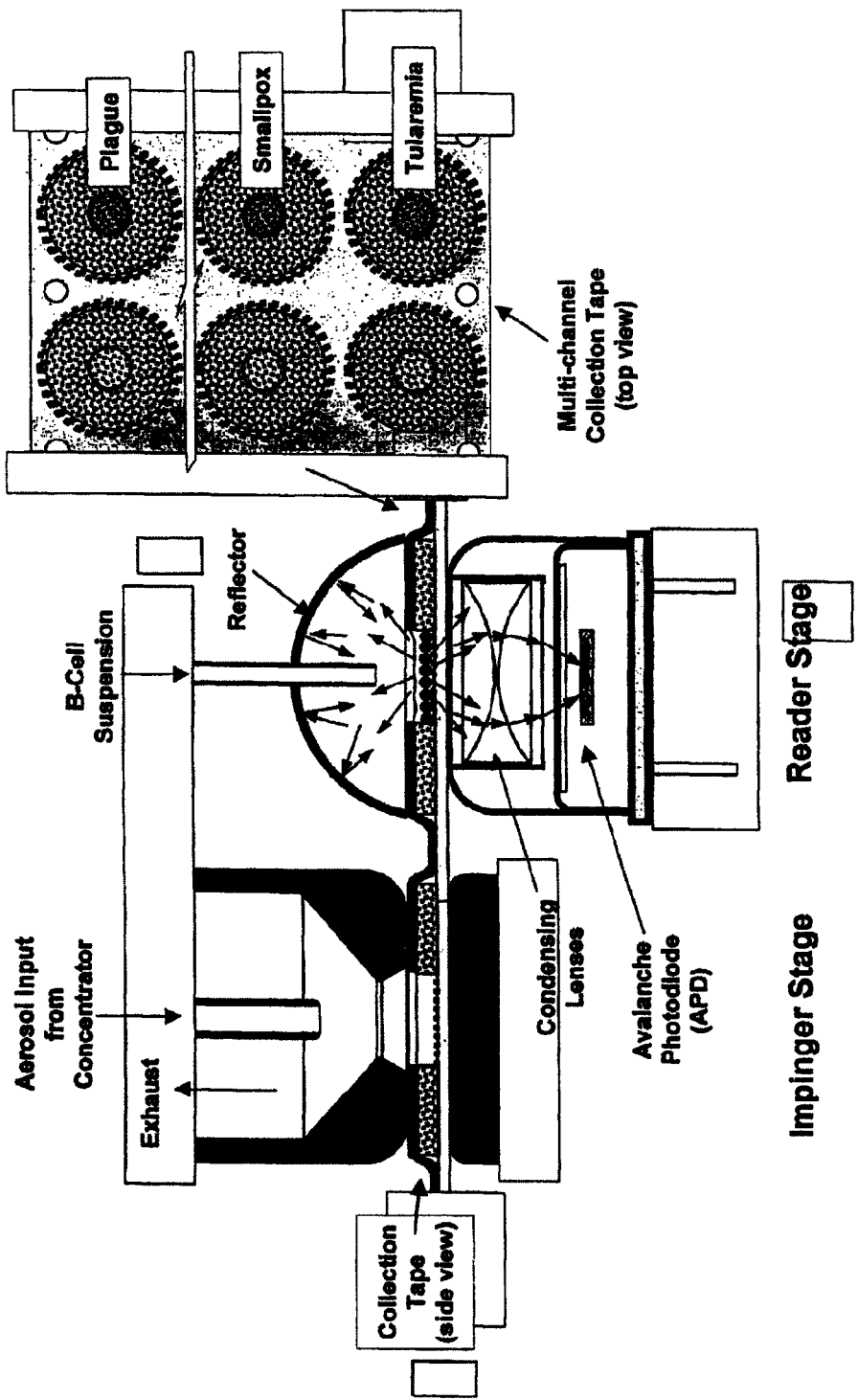
FIG. 14 is a schematic illustrating an optoelectronic sensor.

FIGS. 13-14 describe a different embodiment of the invention that does not require centrifugation. The schematic diagram of FIG. 13 shows the various components of this embodiment. A biological aerosol warning sensor (BAWS) detects the present of particles, e.g., within a pre-determined size range. An example of a BAWS is described in Primmerman, Lincoln Laboratory Journal 12:3-32, 2000. If particles meeting specifications are detected, BAWS triggers an air-to-air concentrator (specimen collector; as described in U.S. Pat. No. 5,932,795) that allows particles of a particular size range to be collected and deposited in a well (reaction chamber) on a portion of a specimen tape at a first station, which is shown in different views in FIG. 14. After candidate particles are deposited in the well, the tape advances to a second station under a reservoir of emitter cells and over a PMT. Emitter cells specific for a particular antigen on a target particles are deposited in the well, and the photon emission from the well monitored.

Figure 26A:
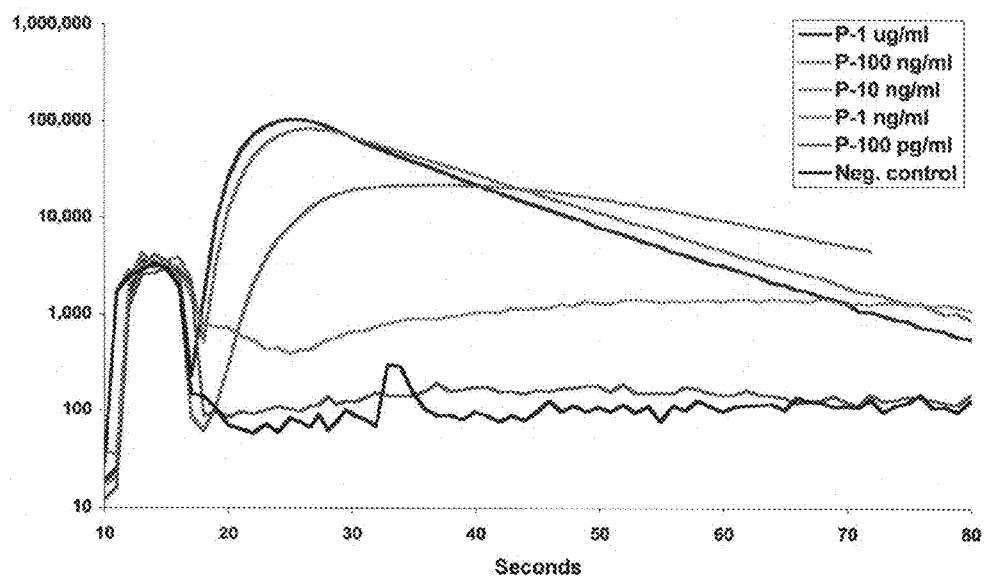
Figure 26B:
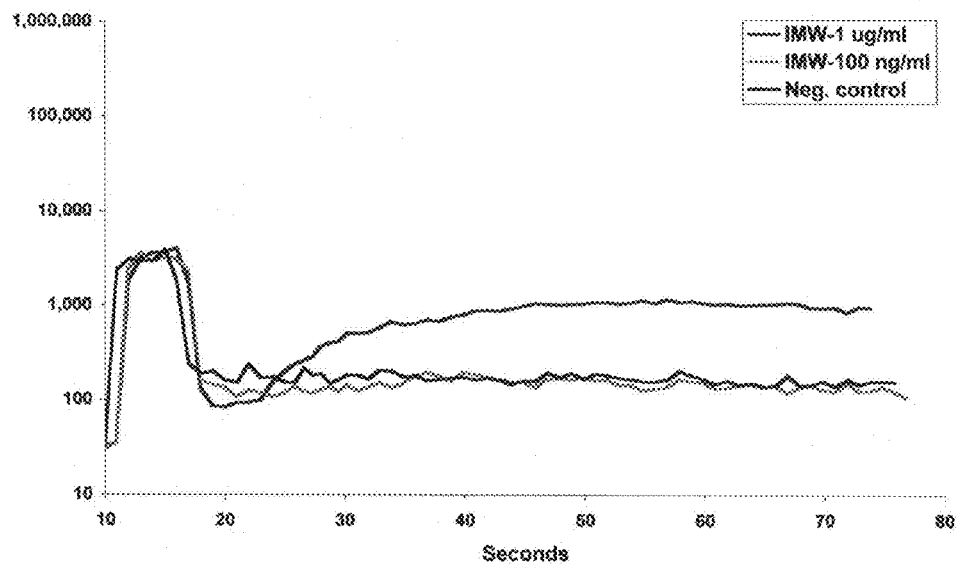
Figure 26C:
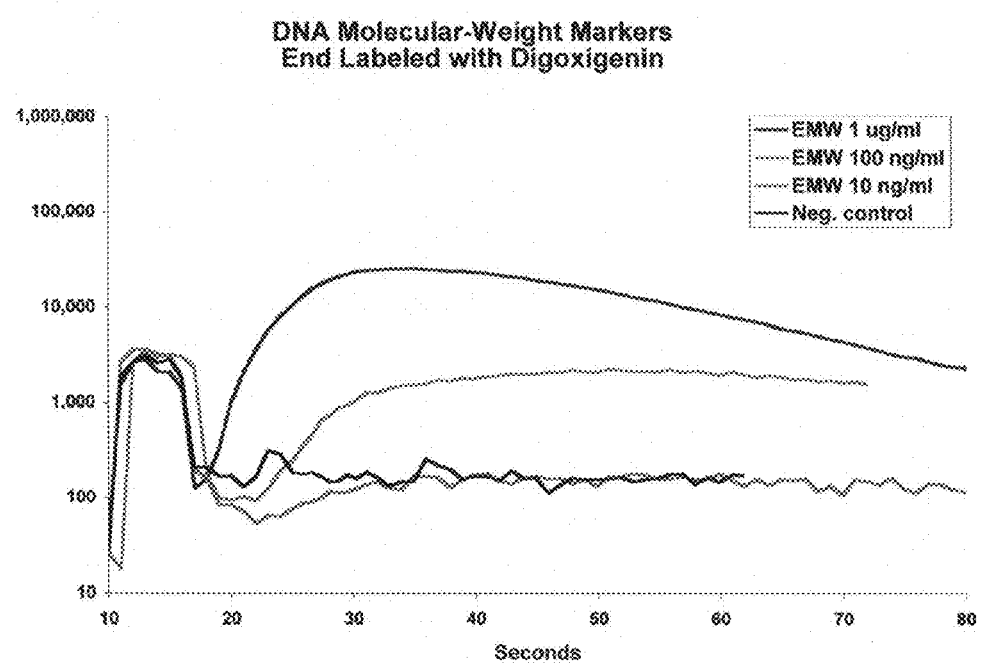

During the time that candidate particles are detected by BAWS, the candidate particles can be deposited on consecutive wells as the tape is advanced through the first station (FIG. 14). In the second station, a plurality of emitter cell reservoirs, each containing emitter cells having different target specificities, are mounted on a turret that rotates a particular reservoir into position to deposit different emitter cells into the well. In this manner, different targets within the candidate particles can be detected, as shown in the schematic top view of the wells in FIG. 14. Of course, if the different emitter cells emit at different wavelengths, it is possible to deposit the different emitter cells into a single well containing candidate particles, provided that the PMT below the second station can distinguish photons of different wavelengths.

FIG. 16 shows schematically yet another embodiment of a system of the invention. In this embodiment, air particles are deposited in each of six wells within a row of a two-dimensional array (e.g., a tape having 6 rows and hundreds of columns) at a first station. As the array is advanced by one row, positioning the row in a second station, different emitter cells are deposited into each well within the row, and emission from all six reactions is detected simultaneously by a row PMTs under the second station. To aid adhesion of particles to the wells on the tape, the wells can be coated with an adhesive or a liquid.

Cell Engineering and Assay Method Examples

A. Cell Engineering Methods:

M12g3R cells were maintained at 37° C. in a humidified atmosphere of 5% $CO_2$ in RPMI 1640 supplemented with 10% fetal bovine serum, 1 mM sodium pyruvate, 2 mM L-glutamine, 100 μM nonessential amino acids, 50 μM 2-mercaptoethanol, 50 μg/ml streptomycin, and 50 U/ml penicillin, 250 ng/ml amphotericin B (Life Technologies). Cells were transfected with pCMV.AEQ.IRES.NEO via electroporation (270 V, 950 μF) and selected in 1 mg/ml G418 for two weeks. G418-resistant clones were screened for response to anti-IgM. Those clones with the greatest increase in photon emission upon crosslinking of the surface IgM were used in subsequent transfections to generate B cell lines specific for particular pathogens. Surface expression of antibodies with engineered specificity is accomplished by co-transfection (via electroporation) with expression vectors for light and heavy chains, as well as with one that encodes a gene conferring resistance to puromycin. Puromycin-resistant pools and clones were selected on the basis of their response to antigen. The light chain expression vector, VKExpress, contains the constant region for the human kappa gene downstream of a multiple cloning site (MCS), under control of the human elongation factor-1α (EF-1α) promoter. The heavy chain vector was generated by modifying pDisplay (Invitrogen), retaining the cytomegalovirus (CMV) promoter and leader sequence, but replacing the platelet-derived growth factor (PDGF) receptor transmembrane domain with the gene for the membrane-bound constant region of murine IgM and removing both tags on either side of the MCS. The appropriate restriction sites are added to the antibody variable regions using PCR and the sequence of all PCR products is confirmed before cloning into the expression construct. The variable regions used to produce the recombinant antibody were cloned either from cDNA or from hybridomas using Reverse-Transcription (RT) with random oligonucleotide primers and PCR. RNA was extracted with Trizol reagent (Life Technologies), according to the manufacturers recommendations, and first strand synthesis performed using the Retroscript kit (Ambion). PCR was accomplished using sets of primers designed to anneal to the leader sequences of either light or heavy chains [S. T. Jones and M. M. Bendig, Bio/Technology 9, 88 (1991)] at the 5' end, and the constant regions of murine Kappa or IgG2 at the 3' end.

B. Bioluminescent B Cell Response to FMDV:

The M12g3R B cell line, stably transfected with the pCMV.AEQ.IRES.NEO plasmid and expression vectors for a recombinant antibody that recognizes the A12 strain of FMDV, was prepared for the luminesence assay as follows: Cells were thawed on Day 1. Preparation of the cells 24 hours post-thaw is critical for maximum activity and reliability. The freeze/thaw step increases the response of the B cells by as much as 100 fold. On Day 2, $10^6$ cells were incubated at room temperature for 2 hours in assay medium [$CO_2$—Independent medium, 10% FBS, 50-μg/ml streptomycin, and 50-U/mil penicillin, 250 ng/ml amphotericin B (Life Technologies)] with 50-μM coelenterazine (Molecular Probes, Eugene, Oreg.) covered with foil, washed twice, and resuspended in assay medium at a final concentration of $5\times10^5$ cells/ml. Cells were left rotating overnight at room temperature in 1.5 ml microcentrifuge tubes and assayed 15-20 hours later. For the assay, 25 μl of cells was mixed with antigen (5 μl of the wt A12pRMC35 strain at $1.4\times10^8$ pfu/ml, 10 μl of the A12 variant, B2PD.3, at $7.5.\times10^7$ pfu/ml) and the response measured in a luminometer (Lumat LB 9507, Perkin Elmer).

C. Bioluminescent Assay with Bacteria and Large Viruses:

The sensor device and methods can be used for the rapid detection of bacterial, as well as viral pathogens. Cell lines were engineered to respond to the bacterium, *Francisella tularensis*, the etiological agent of tularemia. However, when assayed using the same protocol as with the FMD and VEE viruses, the signal is slow and almost indistinguishable from background, indicative of low interaction rates between the B cells and antigen (0 s pre-spin/0 s spin). Previous experiments performed with antigen-bead simulants have indicated that sensitivity and speed could be augmented by concentration of antigen and B cells (data not shown), so the luminometer was re-configured to include a centrifuge positioned above the photomultiplier tube (PMT). When the agent and cells are mixed together, then concentrated by centrifugation for 5 seconds, the signal is improved and the response faster (0 s pre-spin/5 s spin). Optimal results are observed when the slower-sedimenting *F. tularensis* is centrifuged prior to the addition of the cells (60 s pre-spin/5 s spin). This format ensures that a large number of cells come into physical contact with antigen within a short time frame, thereby providing a major improvement in sensitivity and speed. After additional optimization of the assay protocol, we can now detect as little as 60 colony-forming units (cfu) of *F. tularensis* in less than 3 minutes, including the time it takes to pre-spin the agent, but see no response to inactivated *Yersinia pestis*, the bacterium that causes the plague. This limit of detection has been confirmed with two other sources of inactivated *F. tularensis*, and one different strain (data not shown). Furthermore, the sensor device exhibits a wide range of sensitivity, detecting concentrations ranging over 7 orders of magnitude.

B cells were prepared as described above. 50 μl containing the indicated amounts of *Y. pestis* or *F. tularensis* were centrifuged for 60 s at 6500×g, then 20 μl of cells were added and spun an additional 5 s in the centrifuge luminometer. Photons were detected with a Hamamatsu HC-125 photomultiplier tube and the signal monitored with a Stanford Research Systems SR400 Gated Photon Counter.

Nucleic Acid Detection Example
Characterization of Emittor Cells Expressing Digoxigenin Antibody Plasmids encoding an antibody (Daugherty et al. (1998) Protein Engineering 11 (9): 825-832) against digoxigenin were introduced into emittor cells, and these cells were screened using protein (BSA) chemically conjugated to digoxigenin (Dig-BSA). Twelve independent pools were selected resulting in 12-24 independent cell lines. The first experiment tested whether these cells could detect digoxigenin antigens crosslinked by DNA (Dig-DNA). Three types of commercial Dig-DNA have been tested for reactivity with Dig antibody expressing CANARY cells (FIGS. 26A-C): plasmid DNA with a digoxigenin attached every 20 base pairs (FIG. 26A); DNA molecular-weight markers with digoxigenin attached every 200 bases (FIG. 26B); and DNA molecular-weight markers with one digoxigenin attached to each end (FIG. 26C). Each of these standards stimulated the emittor cells to a varying degree, with the most sensitive response being to the Dig-labeled plasmid DNA. The fact that antigens spaced an average of 20 bases apart stimulate the cells 100 fold more (on a per digoxigenin basis, not on a per microgram of DNA basis) than antigens spaced 200 bases apart is an indication that 200 bases is too great of a distance to stimulate an ideal response. In order to stimulate an intracellular cascade resulting in calcium release and aequorin light production, adjacent antibodies must be immobilized near enough to each other to initiate the reaction inside the cell.

Figure 27A:
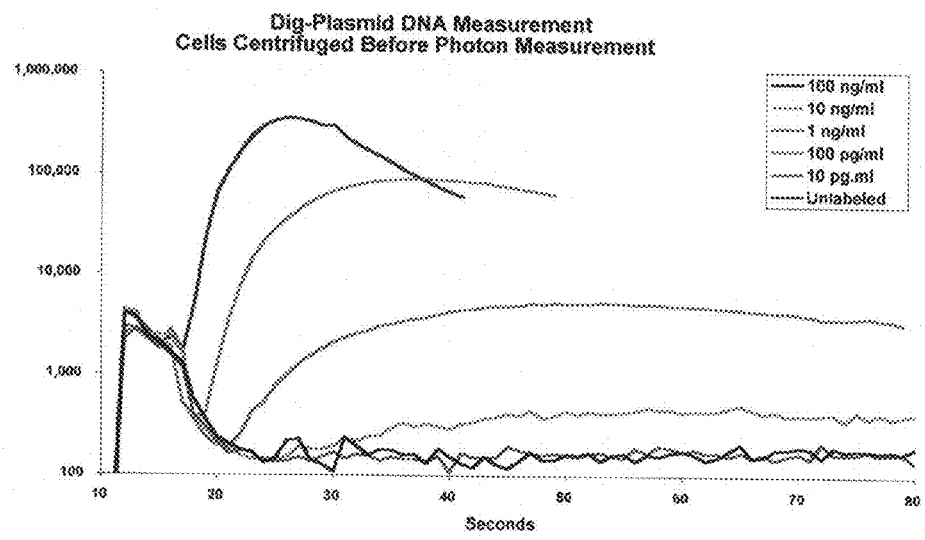
Figure 27B:
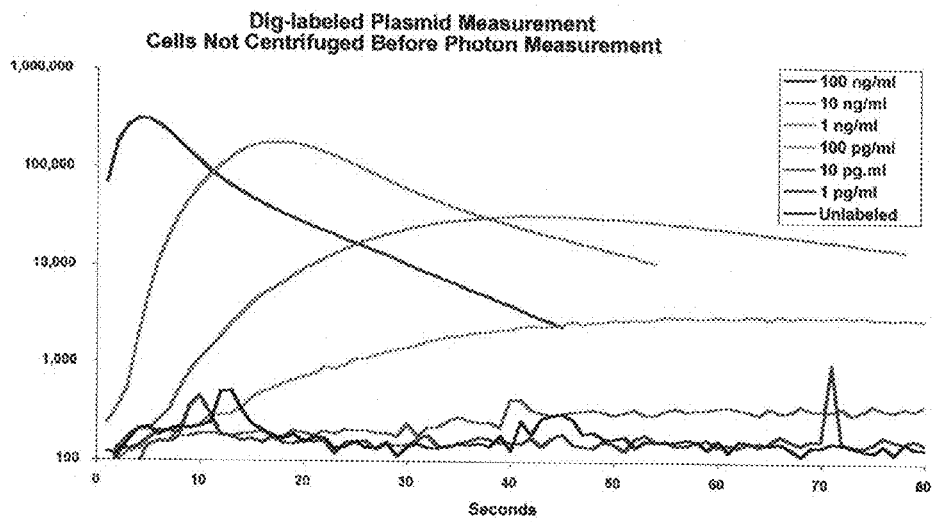

It was also noted that centrifugation just before measurement of light output, which is routine in the detection of both soluble and insoluble antigens using traditional CANARY, may actually decrease the sensitivity of CANARY against the soluble Dig-DNA antigen. In the experiment shown (FIGS. 27A and 27B), centrifuging the cells through the DNA solution appears to decrease the limit of detection by nearly a factor of 10. This result may reflect differences between detection of DNA and detection of other nonsedimentable antigens.

Detection of Hybridized Oligonucleotide Probes Using Emittor Cells

This assay was designed to detect hybridization of digoxigenin-labeled (Dig-labeled) probes to target DNA. The target DNA for these experiments was derived from the phagemid pBluescript II. This 3100 base pair-long circular phagemid can be induced to make double-stranded DNA (dsDNA) or either of the two single strands of DNA (ssDNA). These two ssDNA strands are termed the (+) strand or the (−) strand. Ten Dig-labeled oligonucleotide probes that bind specifically to the (+) strand were designed:

| Oligo number | DNA Sequence | | Phagemid base position | Tm |
|---|---|---|---|---|
| 1 | GCAACGTTGTTGCCATT | (SEQ ID NO: 1) | 2269-2285 | 56.0 |
| 2 | TACAGGCATCGTGGTGT | (SEQ ID NO: 2) | 2288-2304 | 53.3 |
| 3 | GCTCGTCGTTTGGTATGG | (SEQ ID NO: 3) | 2309-2326 | 57.3 |
| 4 | TCATTCAGCTCCGGTTC | (SEQ ID NO: 4) | 2328-2344 | 55.0 |
| 5 | ACGATCAAGGCGAGTTAC | (SEQ ID NO: 5) | 2348-2365 | 53.1 |
| 6 | GATCCCCATGTTGTGC | (SEQ ID NO: 6) | 2368-2384 | 57.7 |
| 7 | AAAGCGGTTAGCTCCTTC | (SEQ ID NO: 7) | 2388-2405 | 54.3 |
| 8 | TCCTCCGATCGTTGTCA | (SEQ ID NO: 8) | 2408-2424 | 56.5 |
| 9 | GTAAGTTGGCCGCAGTG | (SEQ ID NO: 9) | 2428-2444 | 55.7 |
| 10 | TCACTCATGGTTATGGCA | (SEQ ID NO: 10) | 2448-2465 | 53.5 |
| NEG3 | CCATACCAAACGACGAGC | (SEQ ID NO: 11) | 2326-2309 | 57.3 |

Oligonucleotides are numbered in the order of their location along the pBluescript phagemid DNA. Shown for each is the DNA sequence of the oligonucleotide, the position of that sequence on the phagemid, and the melting temperature (Tm) of that oligonucleotide (an approximation of the binding affinity). The small range in Tm's for these oligonucleotides indicate that they each have similar binding characteristics.

Each of these oligonucleotides has a digoxigenin (Dig) molecule attached to the first residue, and each have comparable target DNA binding characteristics as reflected by their similar calculated melting temperatures (Tm). Hybridization of this set of 10 digoxigenin-labeled oligonucleotides to the (+) strand of the target DNA yields a 200 base stretch of double-stranded DNA with one Dig molecule every 20 bases. The remaining 2900 bases of the plasmid remain single stranded. This collection of immobilized digoxigenin antigens crosslink digoxigenin antibodies on the surface of emittor cells and stimulate light production.

Figure 28:
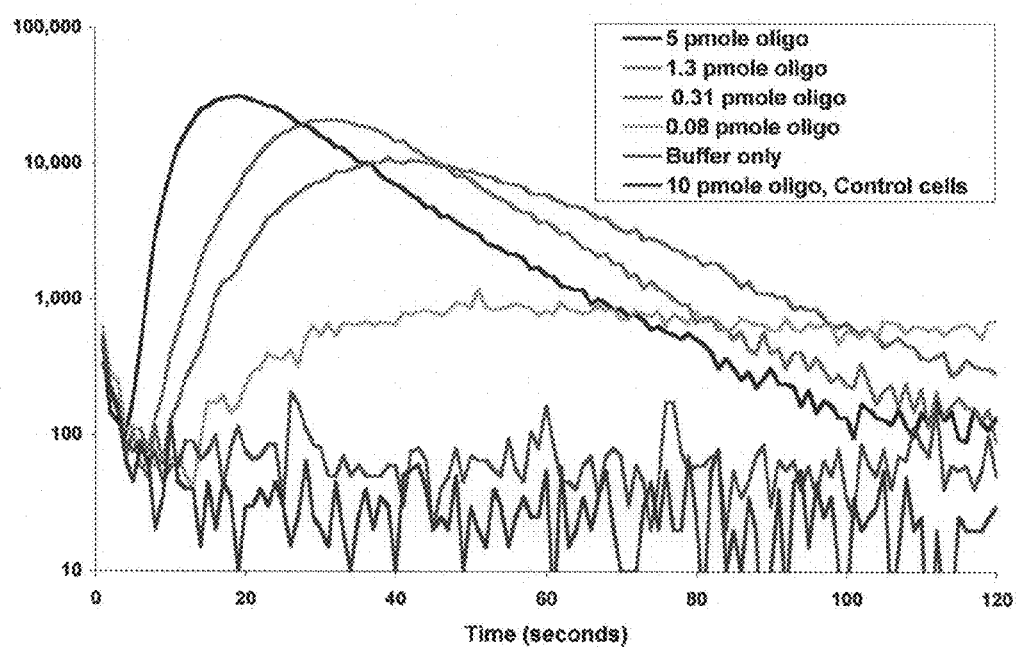

The 11th oligonucleotide (NEG 3) is a control. NEG 3 was designed to bind directly to oligonucleotide number 3, producing a short piece of dsDNA 20 nucleotides long with a single Dig on each end. Emittor cells expressing a digoxigenin antibody were capable of detecting 80 femptomoles of input oligonucleotide (FIG. 28). This control demonstrated that the hybridization conditions chosen were at least sufficient to support binding of two oligonucleotides within this Tm range. More importantly, this control demonstrated that the binding between 20 bases of complementary DNA is sufficiently strong to crosslink antibodies and elicit a signal from the emittor cell.

Figure 29:
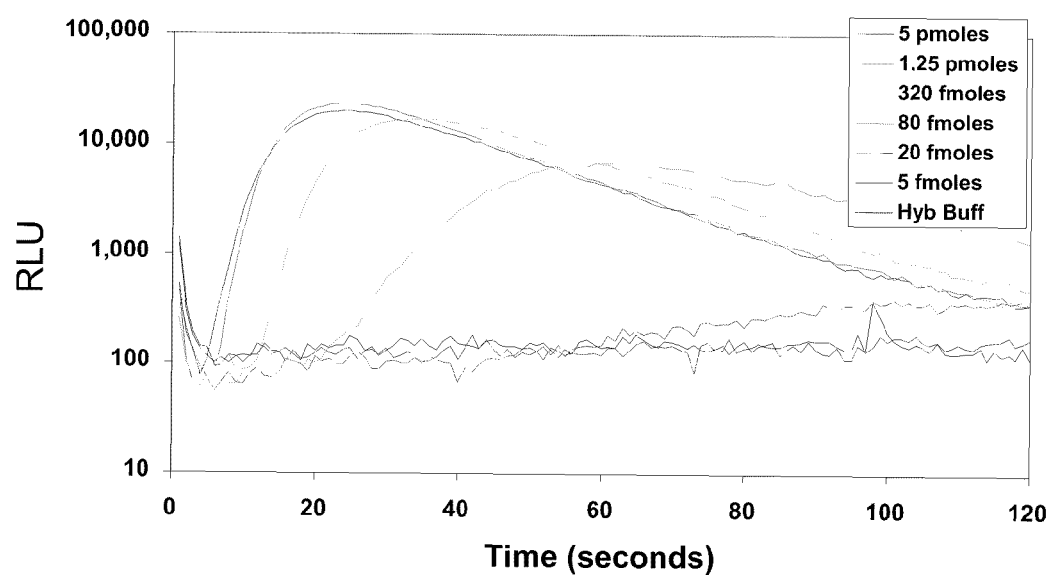

Oligonucleotide-oligonucleotide hybridization occurs extremely quickly (FIG. 29). Oligonucleotide NEG3 was added to hybridization solution, followed by Oligo3. The solution was immediately diluted in medium, the emittor cells added, and the reaction place in the luminometer (elapsed time from addition of oligo 3 was 15 seconds). This abbreviated hybridization protocol did not drastically affect the sensitivity of the assay (compare FIG. 29 to FIG. 28).

Figure 30:
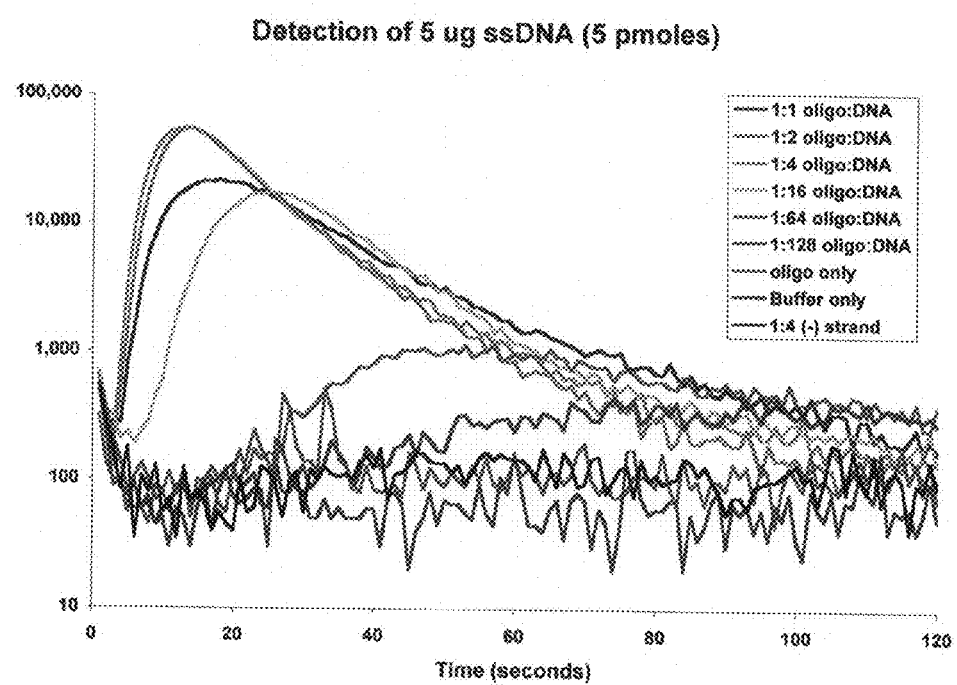
Figure 31:
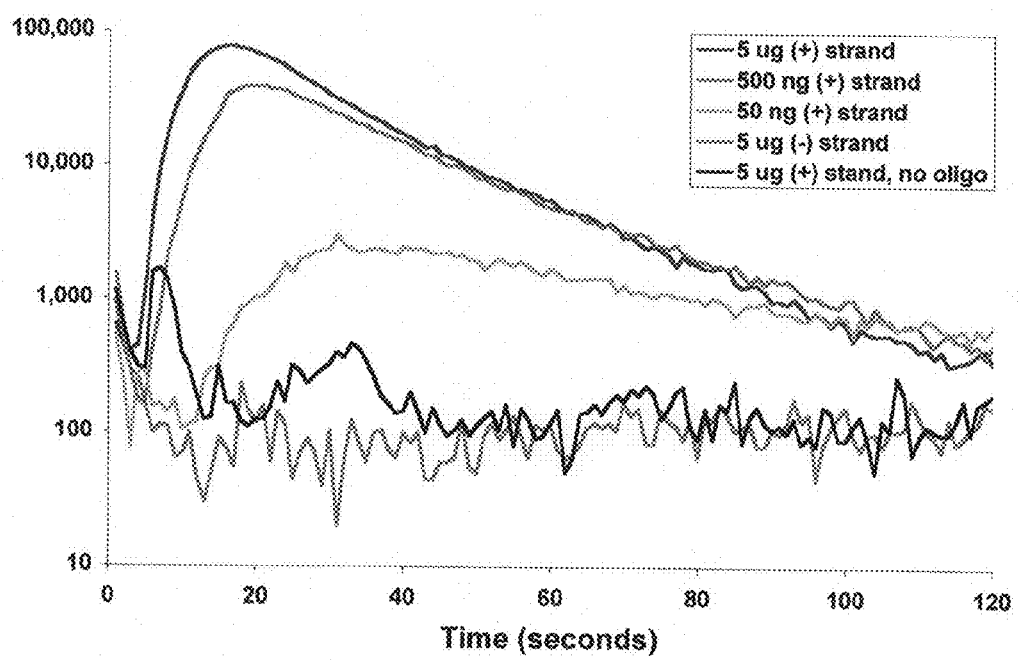

Next, multiple Dig-labeled oligonucleotides were hybridized to single-stranded DNA target. This complex was tested for its ability to stimulate emittor cells. FIG. 30 shows a series of hybridizations of different concentrations of the Dig-oligonucleotide probe set to a given amount of ssDNA. The ratio of ssDNA:oligonucleotide probe giving the best signal in this experiment was between 1:2 and 1:4. At higher concentrations of probe, the unbound Dig-labeled oligonucleotide appeared to inhibit signaling. In these experiments 0.63 pmoles of oligonucleotide worked well under many of the conditions tested. A dose-response curve gives a limit of detection for single stranded DNA of approximately 50 ng, or about 50 fmoles (FIG. 31). It is important to note that (−) strand DNA was not detected in either of these experiments, indicating hybridization of the Dig-labeled oligonucleotides and subsequent signaling from the emittor cells is dependent on the sequence of the target DNA.

Figure 32A:
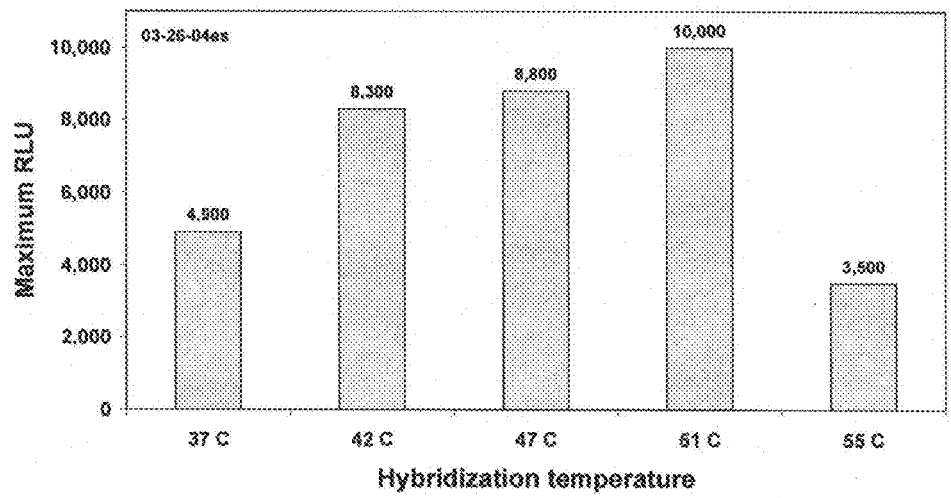
Figure 32B:
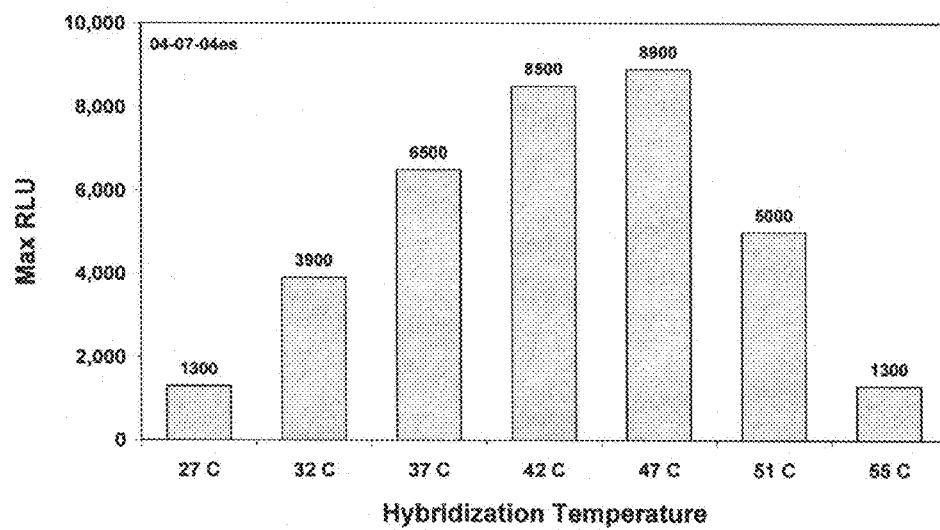

Temperature and buffer constituents affect hybridization of Dig-oligos to target NA. Hybridization at between 47° C. and 51° C. in either PBS (FIG. 32A) or TBS (FIG. 32B) gave the highest response. Hybridizations performed at higher or lower temperatures decreases the amplitude of the signal. Changes in the buffer constituents will obviously affect the ideal hybridization temperature.

Target DNA Capture

Figure 33:
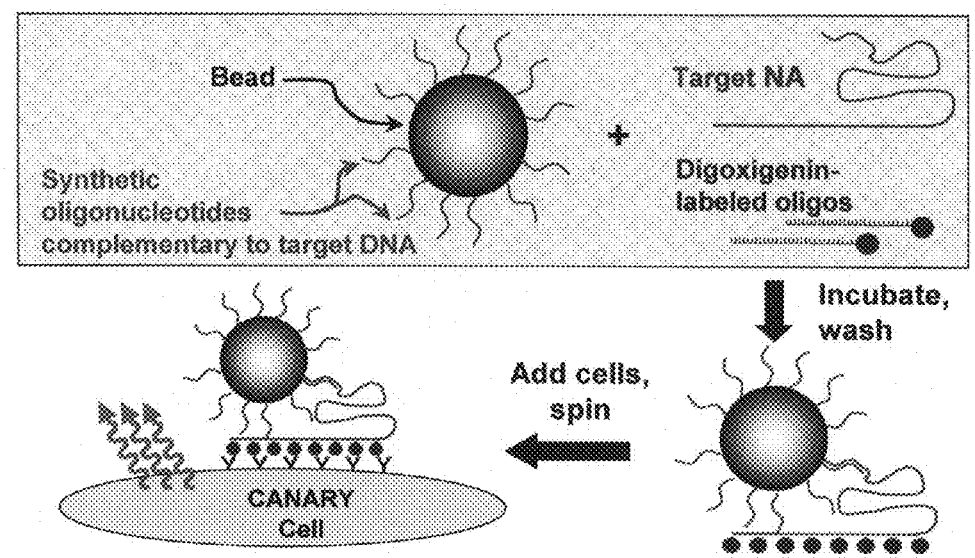
Figure 34:
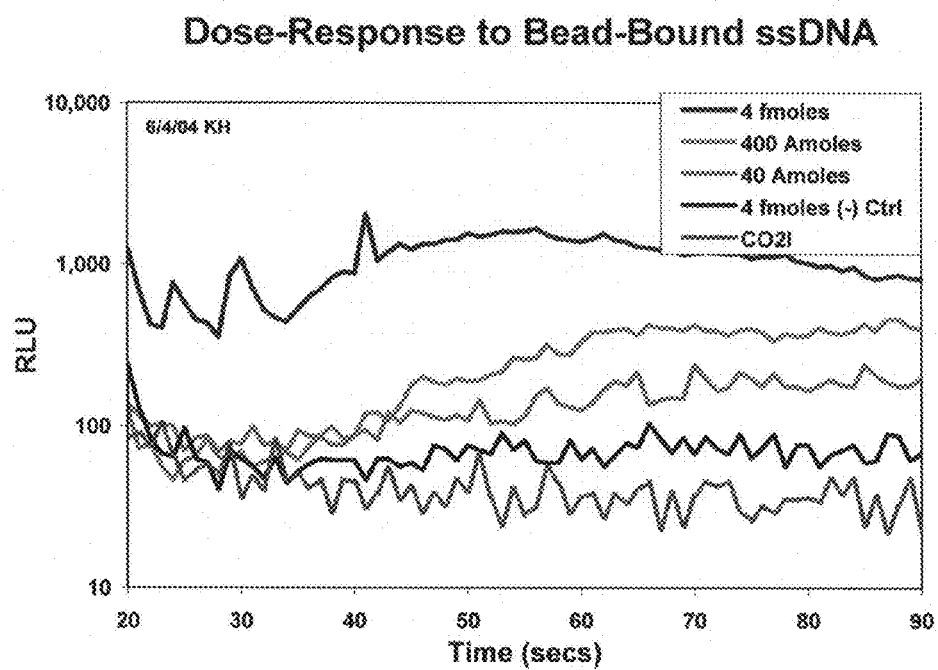
Figure 35:
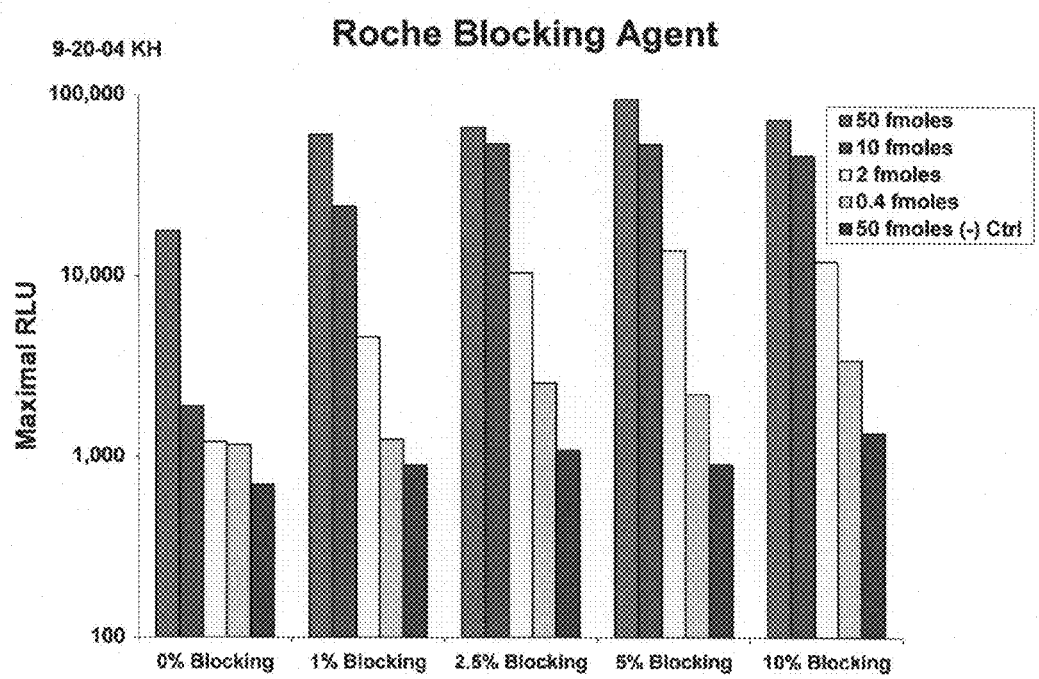
FIG. 35 is a bar chart. pBS phagemid ssDNA was incubated with biotin-labeled oligonucleotide bound to streptavidin-coated polystyrene beads and digoxigenin-labeled oligonucleotides for 20 minutes at 47° C. in the indicated concentrations of blocking reagent. The bead bound, digoxigenin labeled target was washed 3 times in TBS (50 mM Tris, 130 mM NaCl) at room temperature. Beads were resuspended in CO2I medium, emittor cells added, and the reaction spun and light output monitored in a luminometer.

Biotin-labeled oligonucleotides have been bound to the surface of streptavidin-coated magnetic and nonmagnetic beads. These "capture" oligos are designed to bind to the target DNA in a position well removed from the location of the Dig-labeled oligonucleotides. Binding the target NA to a sedimentable support will allow for more extensive washing of the DNA before addition of emittor cells, and improve the sensitivity of the assay. One strategy for sedimentation of target NA is shown in FIG. 33. In this scheme, a biotin-labeled capture oligonucleotide is attached either streptavidin-coated polystyrene or magnetic beads. Digoxigenin-labeled oligonucleotides are hybridized to the target, and the complex sedimented by centrifugation or application of a magnetic field. The emittor cells are then resuspended and sedimented with the beads, and the reaction tube placed in a luminometer. The effects of sedimentation on detection of target DNA is shown in FIG. 34. In this case, the LOD is improved to the high attomole range as compared to typical results in which the DNA is not sedimented. The addition of a commercial blocking reagent (Roche Applied Science Cat. # 1 096 176) improves signal further. FIG. 35 shows the result of addition of different concentrations of blocking agent during the hybridization/capture step. In this experiment, addition of between 1% and 10% blocking reagent improved the signal to background ratio at all concentrations of target tested.

Fc Receptor Emittor Cells

The Fc receptors are a family of membrane-expressed proteins that bind to antibodies or immune complexes. They are expressed on several hematopoietic cells including monocytes and macrophages. Several subclasses of Fc receptors exist including Fc gamma Receptor I (FcγRI), a high-affinity binder of soluble antibody. FcγRI binds to the constant region (Fc portion) of Immunoglobulin G (IgG) leaving the antigen-binding region of the antibody free. Crosslinking of the antibody-bound receptor by specific antigen initiates a signaling pathway that stimulates calcium release.

Figure 36:
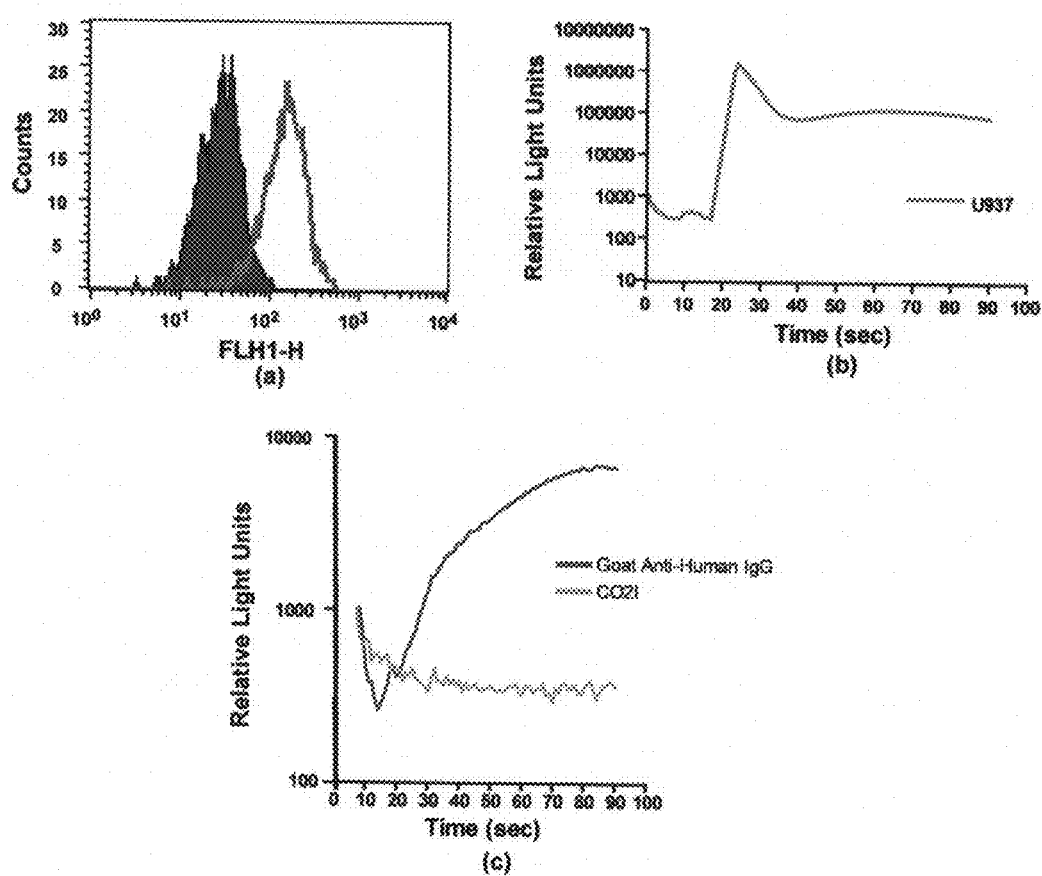
FIGS. 36A-C are graphs.

The human macrophage cell line, U937, contains endogenous FCγR1. Treatment of these cells with IFNγ increases the expression of the FcγRI, as seen in FIG. 36A. U937 cells transfected with the aequorin expression plasmid produce functional aequorin as demonstrated by treating these cells with the calcium ionophore ionomycin. This causes a rapid and transient rise in calcium that stimulates the aequorin to emit light, as seen in FIG. 36B. U937 cells were then tested to determine if the aequorin would be stimulated by the calcium rise initiated by crosslinking of the Fc receptors. U937 cells were incubated with human IgG for 15 min at room temperature. The cells were washed to remove unbound IgG and treated with goat anti-human IgG. A rapid rise in calcium was observed, as shown in FIG. 36C.

Figure 37:
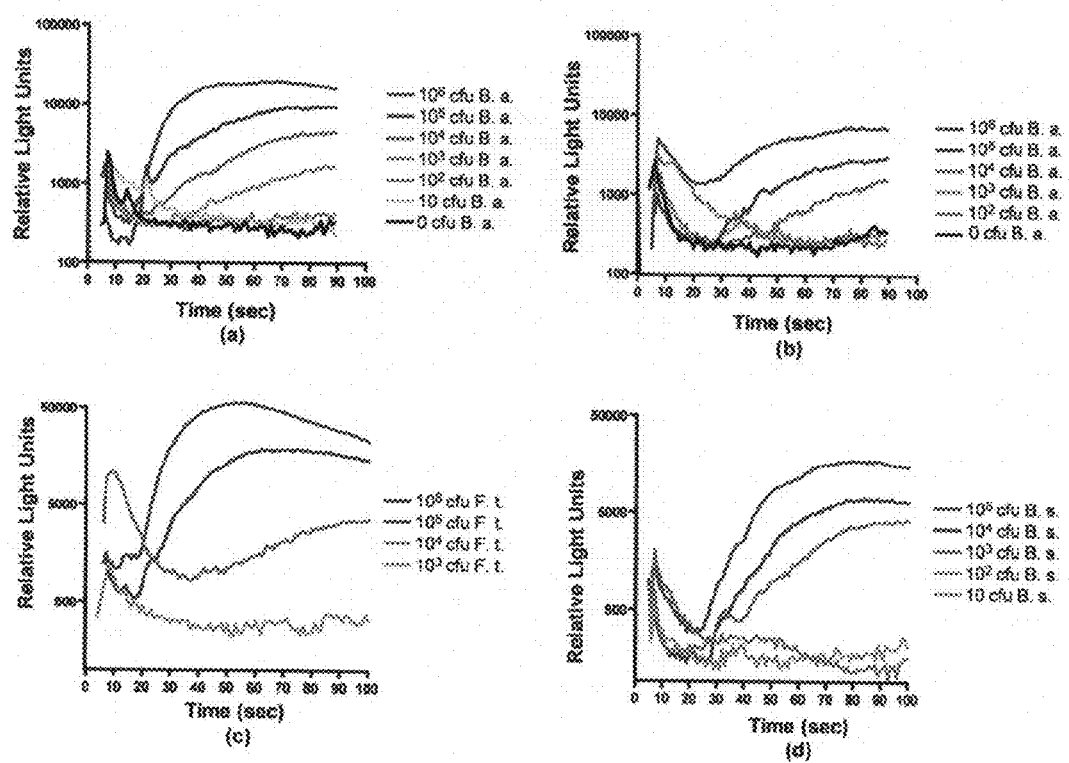
FIGS. 37A-D are graphs. U937 cells can be engineered rapidly to respond to several different pathogens or simulants. U937 cells were treated for 24 h with IFNγ (200 ng/ml) to increase expression of endogenous FcγRI, and prepared for the CANARY assay. The cells were then incubated with the following antibodies.

Experiments demonstrated that U937 cells can be "engineered" rapidly to respond to several different pathogens or simulants. U937 cells were treated for 24 h with IFN (200 ng/ml) to increase expression of endogenous FcγRI, and prepared for the emittor cell assay. The cells were incubated with the following antibodies: mouse anti-*B. anthracis* spore (FIG. 37A), rabbit polyclonal anti-*B. anthracis* spore (FIG. 37B), mouse anti-*F. tularensis* (FIG. 37C), or mouse anti-*B. subtilis* (FIG. 37D). Cells were then used in the standard assay where they detected as few as 1000 cfu *B. anthracis* spores with the monoclonal antibody and 10,000 cfu spores with the rabbit polyclonal, as well as 10,000 cfu *F. tularensis* and 1,000 cfu *B. subtilis* spores.

Figure 38:
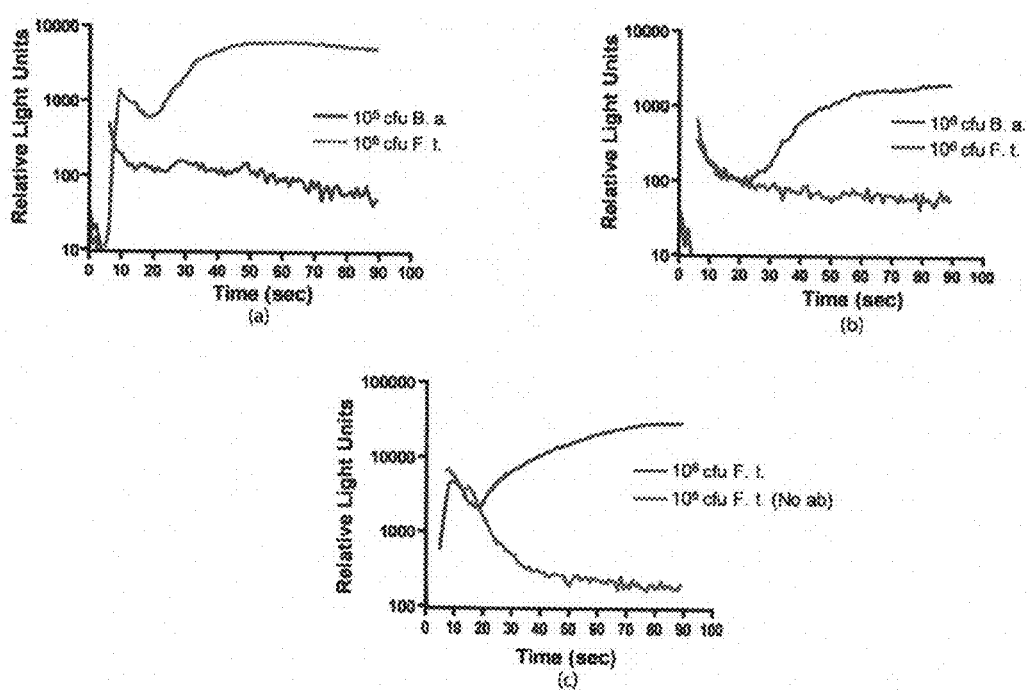
FIGS. 38A-C are graphs. The rapidly engineered U937 cells are specific, and the specificity is determined by the antibody.

The next set of experiments demonstrated that the specificity of the assay is determined by the antibody that is used. U937 cells were incubated with mouse anti-*F. tularensis* antibodies and were tested for their response to 105 cfu of *B. anthracis* spores. As shown in FIG. 38A, the cells did not respond to *B. anthracis* but did to 106 cfu of *F. tularensis*. Alternatively, cells loaded with mouse anti-*B. anthracis* spore antibodies did not respond to *F. tularensis* but did to 106 cfu of *B. anthracis* spores, as shown in FIG. 38B. Furthermore, the cells did not show any response to the 106 cfu of *F. tularensis* in the absence of anti-*F. tularensis* antibody, as seen in FIG. 38C.

16 Channel Sensor Example

A new approach that reduces the time to measure multiple samples (while keeping the hardware requirements minimal) has been successfully tested. An experimental sensor has been designed that allows the simultaneous measurement of 16 samples using a single light-gathering channel. The sensor consists of a rotor holding sixteen 1.5-ml tubes horizontally, equally distributed about its circumference, and driven by a variable speed motor about a vertical axis (FIG. 39). A single fixed photon-detecting element (in this case, a PMT) is positioned in the plane of the rotor just beyond the path of the tubes during rotation. In this way, each of the tubes is sequentially and repetitively brought into close proximity to the PMT, allowing its light output to be sampled on each pass. Finally, an optical switch consisting of an optical source (an infrared LED) and a detector (a phototransistor) is used to control the counting of detected photons and the reorganization of the data into 16 fields, each associated with a specific sample.

A single measurement consists of:
1. Preparing 16 samples (and/or controls) in individual 1.5-ml tubes;
2. Introducing an aliquot of emittor cells into each of the tubes;
3. Installing the tubes into the rotor situated in a dark box;
4. Localizing the emittor cells at the bottom of the tubes using a brief (5 sec) centrifugal spin at high RCF (~2000 g);
5. Reducing the rotor speed to 60 rpm for the duration of the measurement (1-2 min), each tube being sampled once every second; and 6. Generating a time series of photon counts for each sample for display and/or input to a computer algorithm for evaluation.

Figure 40:
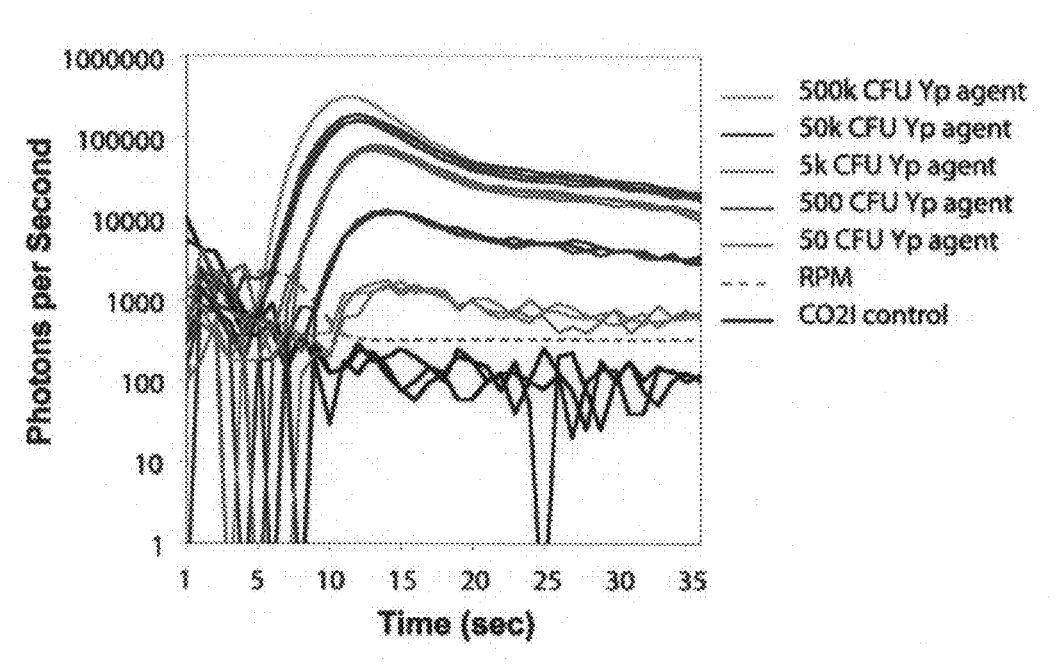
Figure 41:
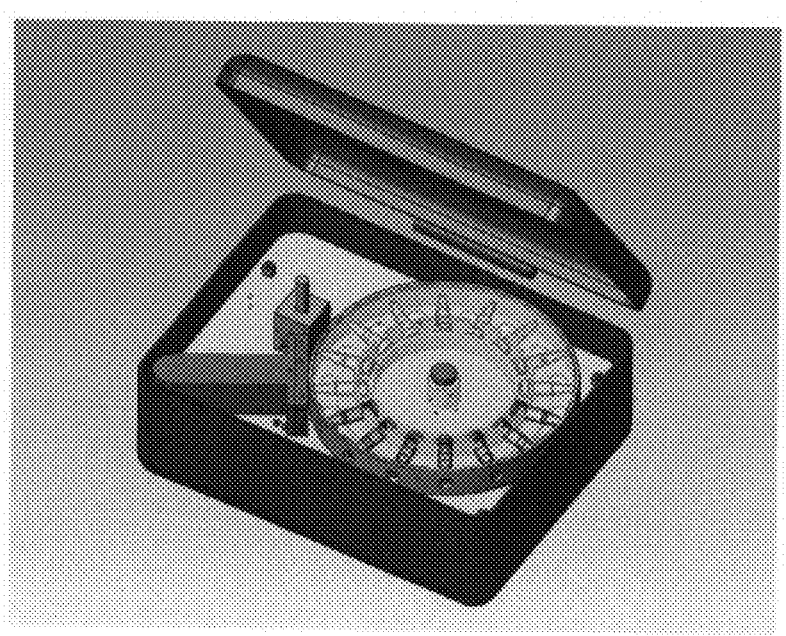

An example of the data from a 16-channel measurement, seen in FIG. 40, shows an LOD comparable to that of the single tube method. While this 16 channel sensor will measure 16 samples as designed, larger sample numbers are possible by increasing the number of channels, though physical size and the statistics of sampling will ultimately dictate practical limits. Similarly, smaller sample numbers are possible by decreasing either the number of samples loaded onto a sensor, or by reducing the number of channels on the sensor. A CAD drawing of the 16-channel portable sensor design is shown in FIG. 41.

A further implementation of this 16-channel design is referred to as a TCAN sensor. The TCAN (Triggered-CANARY) biosensor is an automated biosensor which combines both aerosol collection and B-cell liquid delivery into an integrated radial disc format. The TCAN CANARY disc (CD) (FIG. 42) interfaces with a manifold assembly which splits an air flow into separate channels. The aerosol collection assembly (FIG. 43) uses dry impaction techniques to then localize particles from the air flow into the bottom of clear plastic tubes.

Figure 44:
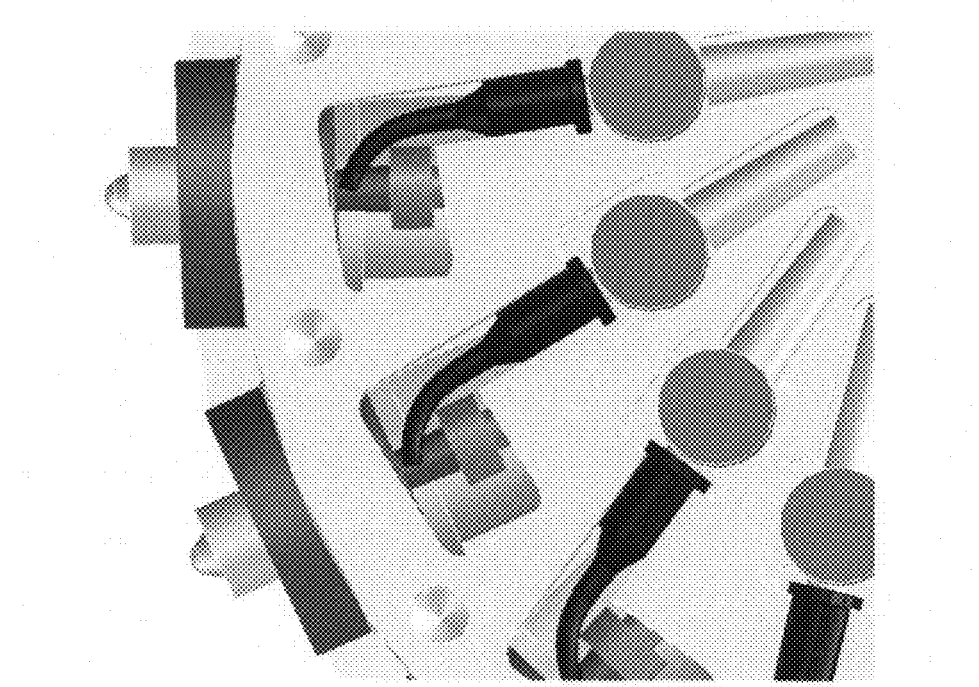

After impaction of aerosol particles, the CD interfaces with the manifold assembly to actuate valves located in the disc. The disc is rapidly spun, which in turn causes the emittor cell liquid to deliver to individual tubes using centrifugal force (FIG. 44). An optical detector is then used to identify potential bioagents based on the photon output emittor cells interacting with the aerosol particles. This process of aerosol collection and emittor cell delivery can be repeated several times in one disc. This feature allows multiple CANARY assays to be performed after several trigger events without changing the CD.

Toxin Detection Example

Figure 48:
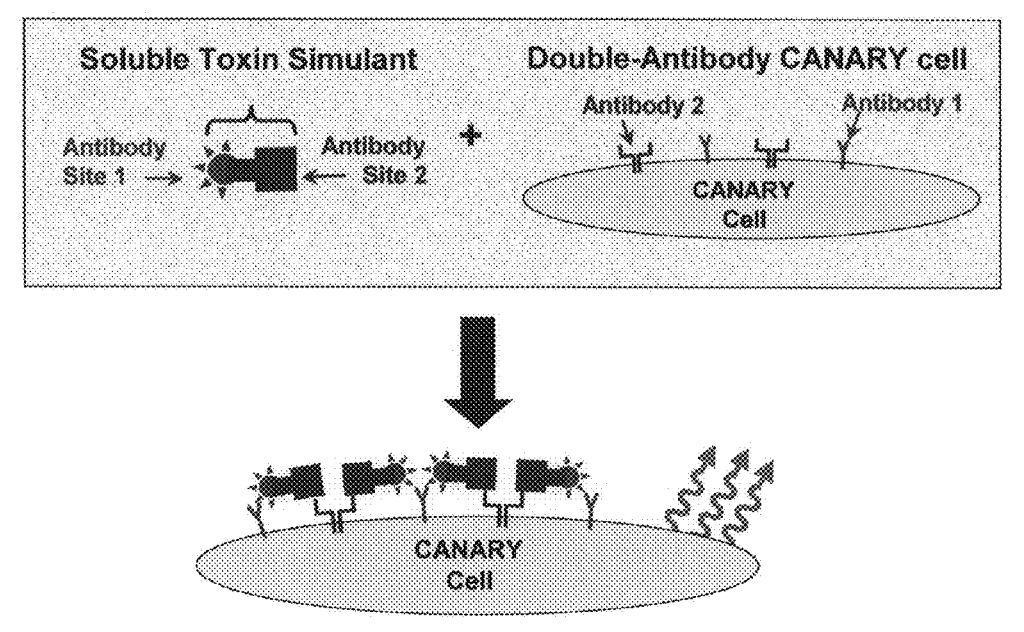

Detection of soluble proteins can be achieved using a variety of methods. For example, in one method, two antibodies can be expressed in the same emittor cell, wherein the two antibodies are each against a different epitope on the same molecule. The antibodies are then crosslinked by monomeric antigen (FIG. 48). It should be pointed out that the sorting of antibodies in the secretory pathway is idealized in the schematic of FIG. 48. In one example, the antibodies can be heterofunctional, i.e., one antibody can have two different functional antigen binding sites. In another example, each antibody has only one functional antigen binding site. This method depends on two factors: (1) multiple functional antibodies are expressed by the same emittor cell and (2) two, linked epitopes are sufficient to stimulate emittor cells (although more than one of these pairs may be required to stimulate a given cell).

Figure 49:
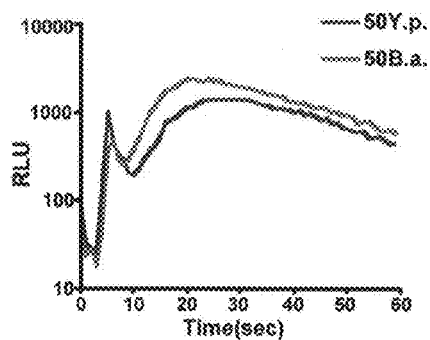

In one experiment, multiple, functional antibodies were expressed in the same emittor cell line (FIG. 49). A single cell line expressing antibodies against *Bacillus anthracis* and *Yersinia pestis* was generated. This clonal cell line reacts against both antigens with good sensitivity. It will be understood that two antibodies against two epitopes on the same soluble monomer can also be functionally expressed. Furthermore, two linked epitopes is sufficient to stimulate emittor cells.

Figure 50:
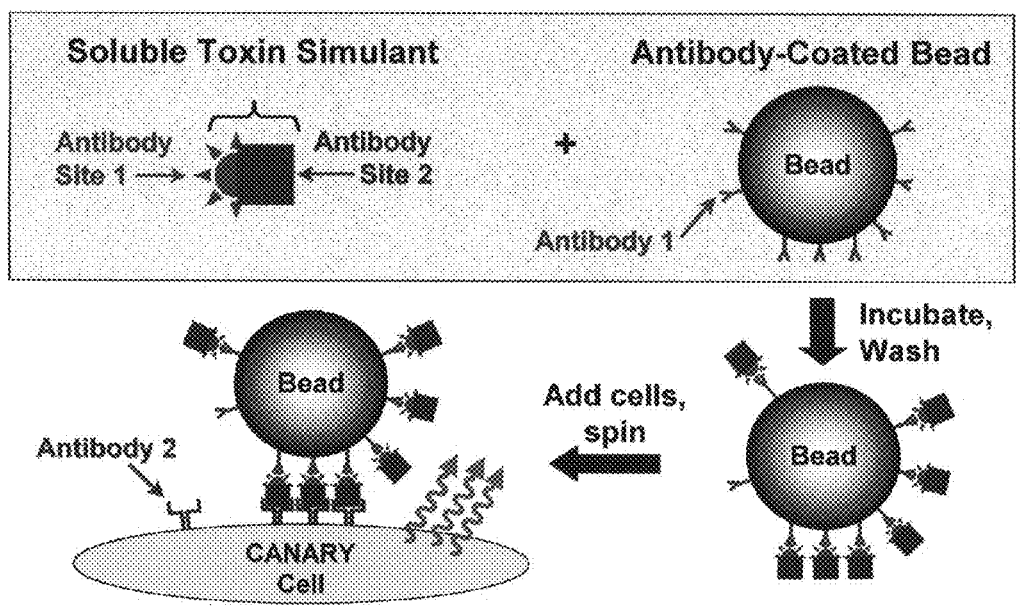

A second method for detecting soluble, monomeric antigens is to crosslink the soluble antigen to make it appear multivalent to the emittor cell (FIG. 50). This crosslinking can be done by attaching the protein to beads, either via tags, in the case of recombinant proteins, or via antibody, as has been demonstrated for botulinum toxin Hc fragment. There are a variety of other possible methods for effectively crosslinking the antigen, as will be understood by those of skill in the art, including precipitation of antigen with trichloroacetic acid (TCA), heat, or ethanol, and attachment of the antigen to a solid phase via ligands, antibodies, or chemical functional groups. This crosslinked monomer can then be detected using emittor cells expressing antibody that recognizes an epitope still available on the crosslinked antigen.

Figure 51:
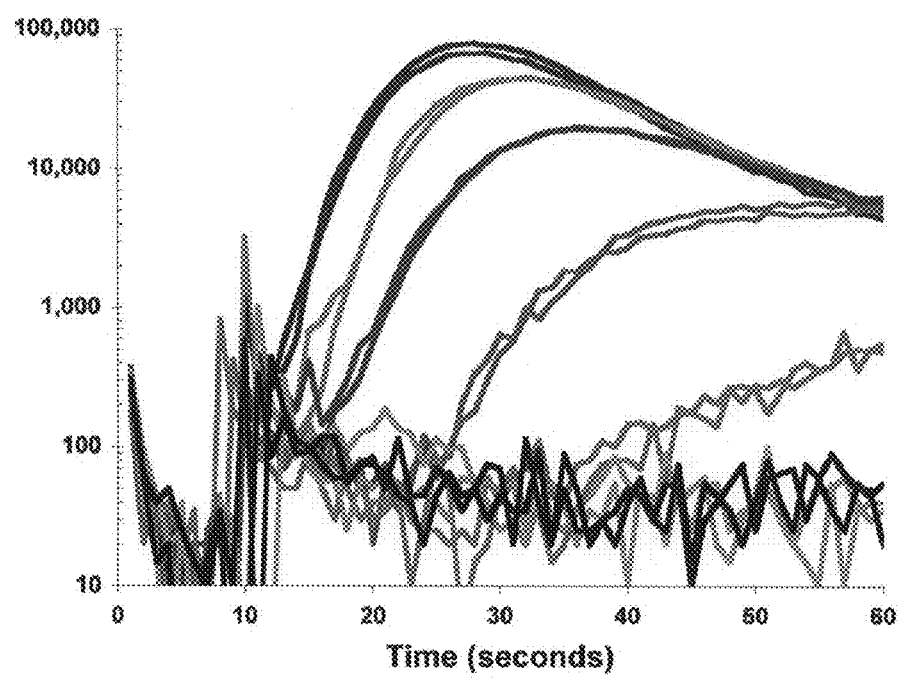

This second method has been demonstrated in practice, using the heavy chain of botulinum toxin type A (BoNT/A Hc) as the soluble, monomeric target protein (FIG. 51) and antibodies described in Pless et al., Infection and Immunity (2001) 570-574. Monoclonal antibody (6E10-10) against one epitope was crosslinked to protein G-coated beads. These beads were incubated with BoNT/A Hc for 3 hrs at 4° C., washed, and used to stimulate emittor cells expressing a second antibody (6B2-2) that recognizes a different BoNT/A Hc epitope. The BoNT/A Hc-decorated beads effectively stimulated the emittor cells, with an LOD of about 6 ng. Emittor cells expressing the same antibody as that used to bind the BoNT/A to the beads were not stimulated, indicating that the emittor reaction was not caused by aggregation of the target protein.

Chemical Detection Example

Chemical detection is of importance in both military and clinical settings. It is possible that some chemicals may have two epitopes to which antibodies can bind independently. In such cases the methods for chemical detection would be identical to that for toxins detection outlined above. In many cases, however, there will not be two independent epitopes on the chemical of interest. In such cases it will be necessary to modify the chemical such that it is capable of stimulating the emittor cell. Four of these modifications are outlined below.

1. Immobilize the chemical of interest on a solid support. Generate emittor cells expressing antibodies that recognize the portion of the chemical that remains available. When the density of the immobilized chemical on the solid support is high enough, antibodies on the emittor cell surface will be immobilized close enough to each other to stimulate the cell. This is analogous with the scheme for toxin detection shown in FIG. 50.

2. First, generate peptide(s) that bind specifically to the chemical. Next, generate antibodies that bind specifically to the chemical-peptide complex. If the chemical-peptide complex is composed of two or more epitopes, the complex can be detected by either of the two-antibody techniques outlined in the section on toxin detection. If the complex is only composed of one specific epitope, then an additional epitope, such as digoxigenin, can be added synthetically to the peptide (FIG. 52) The complex would then contain two antibody binding sites: (1) the epitope formed by the peptide-chemical complex and (2) the digoxigenin epitope. Only in the presence of chemical would both epitopes be present. These two epitopes can then be detected by either of the two-antibody techniques outlined in the section on toxin detection.

Figures 52, 53:
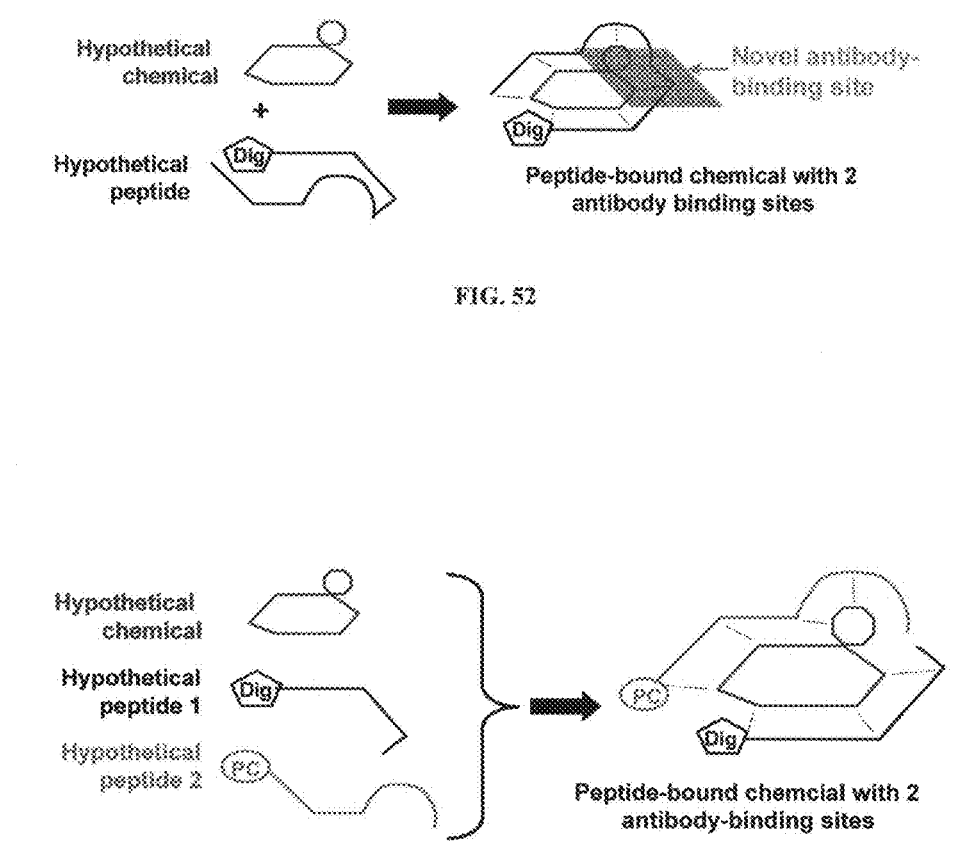

3. Generate two peptides that specifically bind to the chemical (or to each other in the presence of the chemical). Each of these peptides can be synthetically tagged, such that only in the presence of chemical would two epitopes be bound to each other, and therefore detectable by the emittor cell (FIG. 53). Alternatively, one or more antibodies can be made against the peptide-chemical complex, and the presence of chemical detected as above using a combination of antibodies against the complex, or one antibody against the complex and one antibody against a peptide tag.

4. As above, generate peptide(s) that bind specifically to the chemical, and generate antibodies that specifically bind to the peptide-chemical complex. Dimerize the chemical-binding peptide, so that if the dimer binds to two chemicals, it will contain two antibody binding sites. This complex can be detected by emittor cells expressing an antibody against the chemical-peptide complex.

Peptides that bind to small molecules have been isolated from combinatorial libraries. These molecules include porphyrin (Nakamura et al., Biosensors and Bioelectronics 2001, 16: 1095-1100) tryptophan (Sugimoto et al., 1999, 677-678) and cadmium (Mejare et al., 1998, Protein Engineering 11(6): 489-494). However, the use of proteins in the place of peptides may yield higher affinity binders. Libraries have been constructed in which the binding sites have been combinatorially defined, and these can be used to isolate those binding to small molecules. Such a library using lipocalin as the starting protein has been used to isolate binders to digoxigenin variants (Schlehuber and Skerra, 2002, Biophysical Chemistry 96: 213-228). This approach can be used starting with any number of other proteins, but particularly those that might be expected to already have some binding activity with the chemical target (for example, acetylcholinesterase, in the case of VX and Sarin).

While this invention has been particularly shown and described with references to preferred embodiments thereof, it will be understood by those skilled in the art that various changes in form and details may be made therein without departing from the scope of the invention encompassed by the appended claims.

The relevant teachings of all the references, patents and patent applications cited herein are incorporated herein by reference in their entirety.

What is claimed is:

1. A method of detecting a target particle in a sample comprising the steps of:
   a) combining the sample with:
      i) an antibody specific for the target particle; and
      ii) an emittor cell comprising an Fc receptor, wherein binding of the Fc receptor to the antibody results in an increase in intracellular calcium, and wherein said emittor cell further comprises an emittor molecule that emits a photon in response to the increase in intracellular calcium; and
   b) measuring photon emission from the emittor cell, thereby detecting a target particle in a sample.

2. The method of claim 1, wherein emittor cells are B-cells, macrophages or fibroblasts.

3. The method of claim 1, wherein emittor molecules are selected from aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA and cameleons.

4. A method of detecting a soluble antigen in a sample comprising the steps of:
   a) combining the sample with:
      i) one or more antibodies that bind to two different epitopes on the soluble antigen; and
      ii) an emittor cell comprising an Fc receptor, wherein binding of the Fc receptor to the one or more antibodies results in an increase in intracellular calcium, and wherein said emittor cell further comprises an emittor molecule that emits a photon in response to the increase in intracellular calcium; and
   b) measuring photon emission from the emittor cell, thereby detecting the soluble antigen in a sample.

5. The method of claim 4, wherein emittor cells are B-cells, macrophages or fibroblasts.

6. The method of claim 4, wherein emittor molecules are selected from aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA and cameleons.

7. A method of detecting a soluble antigen in a sample comprising the steps of:
   a) combining the sample with an emittor cell comprising one or more antibodies that bind to two different epitopes on the soluble antigen, wherein binding of the one or more antibodies to the soluble antigen results in an increase in intracellular calcium, and wherein said emittor cell further comprises an emittor molecule that emits a photon in response to the increase in intracellular calcium; and
   b) measuring photon emission from the emittor cell, thereby detecting a soluble antigen in a sample.

8. The method of claim 7, wherein the soluble antigen is a protein.

9. The method of claim 7, wherein the soluble antigen is a chemical.

10. The method of claim 7, wherein emittor cells are B-cells, macrophages or fibroblasts.

11. The method of claim 7, wherein emittor molecules are selected from aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA and cameleons.

12. A method of detecting a soluble antigen in a sample comprising the steps of:
   a) combining the sample with a solid substrate comprising a first antibody that binds a first epitope on the soluble antigen, thereby producing a crosslinked soluble antigen bound to a solid substrate;
   b) adding an emittor cell to the crosslinked soluble antigen bound to the solid substrate, wherein said emittor cell comprises a second antibody that binds a second epitope on the soluble antigen, wherein binding of the second antibody to the crosslinked soluble antigen bound to the solid support results in an increase in intracellular calcium, and wherein said emittor cell further comprises an emittor molecule that emits a photon in response to the increase in intracellular calcium; and
   c) measuring photon emission from the emittor cell, thereby detecting a soluble antigen in a sample.

13. The method of claim 12, wherein the soluble antigen is a protein.

14. The method of claim 12, wherein the soluble antigen is a chemical.

15. The method of claim 12, wherein emittor cells are B-cells, macrophages or fibroblasts.

16. The method of claim 12, wherein emittor molecules are are selected from aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA and cameleons.

17. A method of detecting a chemical in a sample comprising the steps of:
   a) combining the chemical with a peptide, thereby producing a chemical-peptide complex;
   b) adding an emittor cell comprising one or more antibodies that bind to two different epitopes on the chemical-peptide complex, wherein binding of the one or more antibodies to the chemical-peptide complex results in an increase in intracellular calcium, and wherein said emittor cell further comprises an emittor molecule that emits a photon in response to the increase in intracellular calcium; and
   c) measuring photon emission from the emittor cell, thereby detecting a chemical in a sample.

18. The method of claim 17, wherein emittor cells are B-cells, macrophages or fibroblasts.

19. The method of claim 17, wherein emittor molecules are are selected from aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA and cameleons.

20. A method of detecting a chemical in a sample comprising the steps of:
   a) combining the chemical with a peptide, thereby producing a chemical-peptide complex;
   b) crosslinking the chemical-peptide complex, thereby producing a crosslinked chemical-peptide complex;
   c) combining with the crosslinked chemical-peptide complex with an emittor cell comprising an antibody that binds to the crosslinked chemical-peptide complex, wherein binding of the antibody to the crosslinked chemical-peptide complex results in an increase in intracellular calcium, and wherein said emittor cell further comprises an emittor molecule that emits a photon in response to the increase in intracellular calcium; and
   d) measuring photon emission from the emittor cell, thereby detecting a chemical in a sample.

21. The method of claim 1, wherein emittor cells are B-cells, macrophages or fibroblasts.

22. The method of claim 20, wherein emittor molecules are selected from aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA and cameleons.

23. A method of detecting a chemical in a sample comprising the steps of:
  a) combining the chemical with an antigen-conjugated peptide, thereby producing a chemical-antigen-conjugated peptide complex;
  b) adding an emittor cell comprising one or more antibodies that bind to two different epitopes on the chemical-antigen-conjugated peptide complex, wherein binding of the one or more antibodies to the chemical-antigen-conjugated peptide complex results in an increase in intracellular calcium, and wherein said emittor cell further comprises an emittor molecule that emits a photon in response to the increase in intracellular calcium; and
  c) measuring photon emission from the emittor cell, thereby detecting a chemical in a sample.

24. A method of detecting a chemical in a sample comprising the steps of:
  a) combining the chemical with an antigen-conjugated peptide, thereby producing a chemical-antigen-conjugated peptide complex;
  b) crosslinking the chemical-antigen-conjugated peptide complex, thereby producing a crosslinked chemical-antigen-conjugated peptide complex;
  c) adding an emittor cell comprising an antibody that binds to the crosslinked chemical-antigen-conjugated peptide complex, wherein binding of the antibody to the chemical-antigen-conjugated peptide complex results in an increase in intracellular calcium, and wherein said emittor cell further comprises an emittor molecule that emits a photon in response to the increase in intracellular calcium; and
  d) measuring photon emission from the emittor cell, thereby detecting a chemical in a sample.

* * * * *

```
                         SEQUENCE LISTING

<160> NUMBER OF SEQ ID NOS: 11

<210> SEQ ID NO 1
<211> LENGTH: 17
<212> TYPE: DNA
<213> ORGANISM: Artificial Sequence
<220> FEATURE:
<223> OTHER INFORMATION: Oligonucleotide

<400> SEQUENCE: 1
gcaacgttgt tgccatt                                                    17

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide

<400> SEQUENCE: 2
tacaggcatc gtggtgt                                                    17

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide

<400> SEQUENCE: 3
gctcgtcgtt tggtatgg                                                   18

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide

<400> SEQUENCE: 4
tcattcagct ccggttc                                                    17

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide
```

```
<400> SEQUENCE: 5
acgatcaagg cgagttac                                                18

<210> SEQ ID NO 6
<211> LENGTH: 17
<212> TYPE: DNA
<213> ORGANISM: Artificial Sequence
<220> FEATURE:
<223> OTHER INFORMATION: Oligonucleotide

<400> SEQUENCE: 6
gatcccccat gttgtgc                                                 17

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7
aaagcggtta gctccttc                                                18

<210> SEQ ID NO 8
<211> LENGTH: 17
<212> TYPE: DNA
<213> ORGANISM: Artificial Sequence
<220> FEATURE:
<223> OTHER INFORMATION: Oligonucleotide

<400> SEQUENCE: 8
tcctccgatc gttgtca                                                 17

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide

<400> SEQUENCE: 9
gtaagttggc cgcagtg                                                 17

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide

<400> SEQUENCE: 10
tcactcatgg ttatggca                                                18

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide

<400> SEQUENCE: 11
ccataccaaa cgacgagc                                                18
```